United States Patent
Fares et al.

(10) Patent No.: US 12,029,780 B2
(45) Date of Patent: Jul. 9, 2024

(54) LONG-ACTING POLYPEPTIDES AND METHODS OF PRODUCING AND ADMINISTERING SAME

(71) Applicant: OPKO BIOLOGICS LTD., Kiryat Gat (IL)

(72) Inventors: Fuad Fares, Hourfish Village (IL); Udi Eyal Fima, Dvira (IL)

(73) Assignee: OPKO BIOLOGICS LTD., Kiryat Gat (IL)

( * ) Notice: Subject to any disclaimer, the term of this patent is extended or adjusted under 35 U.S.C. 154(b) by 0 days.

(21) Appl. No.: 17/549,017

(22) Filed: Dec. 13, 2021

(65) Prior Publication Data

US 2022/0241380 A1 Aug. 4, 2022

Related U.S. Application Data

(60) Division of application No. 15/200,813, filed on Jul. 1, 2016, now Pat. No. 11,197,915, which is a continuation of application No. 14/555,308, filed on Nov. 26, 2014, now abandoned, which is a continuation of application No. PCT/IL2014/050910, filed on Oct. 21, 2014, which is a continuation-in-part of application No. 14/059,134, filed on Oct. 21, 2013, now abandoned, and a continuation-in-part of application No. 14/309,496, filed on Jun. 19, 2014, now abandoned.

(51) Int. Cl.

| | | |
|---|---|---|
| *A61K 38/27* | (2006.01) | |
| *A61K 38/24* | (2006.01) | |
| *A61K 47/00* | (2006.01) | |
| *A61K 47/02* | (2006.01) | |
| *A61K 47/12* | (2006.01) | |
| *C07K 14/475* | (2006.01) | |
| *C07K 14/505* | (2006.01) | |
| *C07K 14/555* | (2006.01) | |
| *C07K 14/59* | (2006.01) | |
| *C07K 14/61* | (2006.01) | |
| *C07K 19/00* | (2006.01) | |
| *G01N 33/74* | (2006.01) | |

(52) U.S. Cl.
CPC ............ *A61K 38/27* (2013.01); *A61K 38/24* (2013.01); *A61K 47/02* (2013.01); *A61K 47/12* (2013.01); *C07K 14/505* (2013.01); *C07K 14/555* (2013.01); *C07K 14/59* (2013.01); *C07K 14/61* (2013.01); *G01N 33/74* (2013.01); *C07K 2319/00* (2013.01); *C07K 2319/31* (2013.01); *G01N 2333/65* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,911,691 A | 3/1990 | Anuik et al. |
| 5,011,771 A | 4/1991 | Bellet et al. |
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |

(Continued)

FOREIGN PATENT DOCUMENTS

| | | |
|---|---|---|
| CN | 1528787 | 9/2004 |
| CN | 1528894 | 3/2006 |

(Continued)

OTHER PUBLICATIONS

Takano et al. A Comparison of Subcutaneous and Intramuscular Administration of Human Growth Hormone (hGH) and Increased Growth Rate by Daily Injection of hGH in GH Deficient Children; Endocrinol. Japon. 1988, 35 (3), 477-484; (1988). (Year: 1988).*

(Continued)

*Primary Examiner* — Elizabeth C. Kemmerer
*Assistant Examiner* — Regina M DeBerry
(74) *Attorney, Agent, or Firm* — Arnold & Porter Kaye Scholer LLP

(57) ABSTRACT

CTP-modified human growth hormone polypeptides and pharmaceutical formulations and pharmaceutical compositions comprising the same and methods of producing, and using the same are disclosed.

13 Claims, 35 Drawing Sheets

Specification includes a Sequence Listing.

(56) References Cited

U.S. PATENT DOCUMENTS

| | | |
|---|---|---|
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,824,642 A | 10/1998 | Attie |
| 5,919,455 A | 7/1999 | Greenwald et al. |
| 5,929,028 A | 7/1999 | Skrabanja et al. |
| 5,932,447 A | 8/1999 | Siegal |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Ohannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,585,837 B2 | 9/2009 | Shechter et al. |
| 7,649,084 B2 | 1/2010 | Ferguson et al. |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,304,386 B2 | 11/2012 | Fares et al. |
| 8,426,166 B2 | 1/2013 | Fares et al. |
| 8,450,269 B2 | 5/2013 | Fares et al. |
| 8,465,958 B2 | 6/2013 | Lopez De Leon et al. |
| 8,476,234 B2 | 7/2013 | Fima et al. |
| 8,759,292 B2 | 6/2014 | Fima et al. |
| 8,946,155 B2 | 2/2015 | Fares et al. |
| 9,249,407 B2 | 2/2016 | Fima et al. |
| 9,808,534 B2 | 11/2017 | Hershkovitz et al. |
| 9,821,070 B2 | 11/2017 | Fima et al. |
| 9,828,417 B2 | 11/2017 | Fima et al. |
| 9,884,901 B2 | 2/2018 | Fares et al. |
| 10,119,132 B2 | 11/2018 | Fima et al. |
| 10,351,615 B2 * | 7/2019 | Fares .................. C07K 14/59 |
| 2001/0007757 A1 | 7/2001 | Boime et al. |
| 2001/0028895 A1 | 10/2001 | Bisgaier et al. |
| 2002/0127652 A1 | 9/2002 | Schambye et al. |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2004/0138227 A1 | 7/2004 | Nishiyama et al. |
| 2004/0209804 A1 | 10/2004 | Govardhan |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkiels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1 | 8/2008 | Minev et al. |
| 2009/0053185 A1 | 2/2009 | Schulte et al. |
| 2009/0087411 A1 | 4/2009 | Fares et al. |
| 2009/0130060 A1 | 5/2009 | Wiemer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 * | 12/2009 | Fares .................. C07K 14/505 |
| | | 435/360 |
| 2010/0006156 A1 | 1/2010 | Schlip et al. |
| 2010/0081614 A1 * | 4/2010 | Fares .................. C07K 14/505 |
| | | 530/345 |
| 2010/0144617 A1 | 6/2010 | Sinha Roy et al. |
| 2010/0190611 A1 | 7/2010 | Machida |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152181 A1 | 6/2011 | Alsina-Fernandez et al. |
| 2011/0152182 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0048878 A1 | 3/2012 | Burger et al. |
| 2012/0114651 A1 | 5/2012 | De W-ldt et al. |
| 2012/0208759 A1 | 8/2012 | Fima et al. |
| 2012/0231999 A1 | 9/2012 | Alagarsamy et al. |
| 2013/0183052 A1 | 7/2013 | Tsukada |
| 2013/0184207 A1 | 7/2013 | Fares et al. |
| 2013/0243747 A1 | 9/2013 | Fima et al. |
| 2013/0295072 A1 | 11/2013 | Fima et al. |
| 2014/0113860 A1 | 4/2014 | Fima et al. |
| 2014/0170728 A1 | 6/2014 | DeFrees et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0072924 A1 | 3/2015 | Fima et al. |
| 2015/0079063 A1 | 3/2015 | Fima et al. |
| 2015/0158926 A1 | 6/2015 | Fares et al. |
| 2015/0203558 A1 | 7/2015 | Fares et al. |
| 2015/0258208 A1 | 9/2015 | Fima et al. |
| 2015/0368630 A9 | 12/2015 | Fima et al. |
| 2016/0168588 A1 | 6/2016 | Hershkovitz et al. |

FOREIGN PATENT DOCUMENTS

| | | |
|---|---|---|
| CN | 102639144 | 8/2012 |
| EP | 0167825 | 1/1986 |
| EP | 0264166 | 4/1988 |
| EP | 0374257 | 6/1990 |
| EP | 01319712 | 6/2003 |
| EP | 2532674 | 12/2012 |
| EP | 2420251 | 3/2013 |

(56) References Cited

FOREIGN PATENT DOCUMENTS

| | | |
|---|---|---|
| JP | 2002226365 | 8/2002 |
| JP | 2002255857 | 9/2002 |
| JP | 2004269516 | 9/2004 |
| JP | 2015-163650 | 9/2015 |
| KR | 20030037598 | 5/2003 |
| WO | 1989/010756 | 11/1989 |
| WO | 1993/006844 | 4/1993 |
| WO | 1994/024148 | 10/1994 |
| WO | 1999/025849 | 5/1999 |
| WO | 2000/023472 | 4/2000 |
| WO | 2002/036169 | 5/2002 |
| WO | 2002/048194 | 6/2002 |
| WO | 2002/085311 | 10/2002 |
| WO | 2003/038100 | 5/2003 |
| WO | 2003/046013 | 6/2003 |
| WO | 2003/048210 | 6/2003 |
| WO | 2004/006756 | 1/2004 |
| WO | 2004/089280 | 10/2004 |
| WO | 2005/035761 | 4/2005 |
| WO | 2005/080544 | 9/2005 |
| WO | 2006/018204 | 2/2006 |
| WO | 2006/051288 | 5/2006 |
| WO | 2006/134340 | 12/2006 |
| WO | 2007/094985 | 8/2007 |
| WO | 2007/149406 | 12/2007 |
| WO | 2008/074032 | 6/2008 |
| WO | 2010/007622 | 1/2010 |
| WO | 2010/097077 | 9/2010 |
| WO | 2010/099746 | 9/2010 |
| WO | 2011/004361 | 1/2011 |
| WO | 2011/087672 | 7/2011 |
| WO | 2012/011752 | 5/2012 |
| WO | 2012/167251 | 12/2012 |
| WO | 2012/173422 | 12/2012 |
| WO | 2013/018098 | 2/2013 |
| WO | 2013/086167 | 6/2013 |
| WO | 2013/096386 | 6/2013 |
| WO | 2013/121416 | 8/2013 |
| WO | 2013/157002 | 10/2013 |
| WO | 2013/183052 | 12/2013 |
| WO | 2014/080401 | 5/2014 |
| WO | 2016/092549 | 6/2016 |
| WO | 2016/092550 | 6/2016 |
| WO | 2016/193969 | 12/2016 |
| WO | 2016/203482 | 12/2016 |

OTHER PUBLICATIONS

Riddick et al. A Stepwise Increase in Recombinant Human Growth Hormone Dosing During Puberty Achieves Improved Pubertal Growth: A National Cooperative Growth Study Report, Journal of Pediatric Endocrinology & Metabolism, 22, 623-628; (2009) (Year: 2009).*
Peter et al. Three-Year Efficacy and Safety of LB03002, a Once-Weekly Sustained-Release Growth Hormone (GH) Preparation, in Prepubertal Children with GH Deficiency (GHD). J Clin Endocrinol. Metab. vol. 97(2):400-407 (Feb. 2012). (Year: 2012).*
Alberts et al., eds., *Molecular Biology of the Cell*, 5th ed. (Garland Science), p. 367 (2006).
Ameredes et al., "Growth Hormone Improves Body Mass Recovery with Refeeding after Chronic Undernutrition-Induced Muscle Atrophy in Aging Male Rats," *Journal of Nutrition*, 12:2264-2270 (1999).
Amirizahdeh et al., "Expression of Biologically Active Recombinant B-Domain-Deleted Human VIII in Mammalian Cells," *Journal of Science*, 16(2): 103-112 (2005)
Anonymous, "Prolor Biotech Announces Positive Results of its Obesity/Diabetes Drug Candidate in Preclinical Weight Loss Study," Apr. 17, 2012, pp. 1-2; Retrieved from the Internet at web[dot]archive[dot]org/web/20120526154526/http://www[dot]prolor-biotech[dot]com/_Uploads/dbsAttachedFiles/NewsPROLOR AnnouncesObesity DiabetesStudyResults[dot]pdf.
Anonymous, "Prolor Biotech Receives New U.S. Patent Allowance Covering Broad Applications of its CTP Platform for Long Acting Therapeutic Proteins," Jul. 11, 2011, pp. 1-2; retrieved from the Internet at web[dot]archive[dot]org/web/20110725053527/ http://www[dot]prolor-biotech[dot]com/ _Uploads/dbsAttachedFiles/NewsPROLORAnnouncesAllowanceOfNewCTP-PlatformPatentByUSPatentOffice[dot]pdf.
Anonymous, "Corporate Presentation—Lazard Capital Markets Healthcare Conference," Nov. 15, 2011, pp. 1-19; Retrieved from the Internet at web[dot]archive[dot]org/web/20110628023057/ http://www[dot]prolor-biotech[dot]com/_Uploads/dbsAttachedFiles/prolorInvestorsNov2011[dot]pdf.
Anonymous, "Corporate Presentation," Jun. 1, 2011, pp. 1-35; Retrieved from the Internet at web[dot]archive[dot]org/web/20110628023057/ http://www[dot]prolor-biotech [dot]com/_Uploads/dbsAttachedFiles/prolorPresentationJune2011Investors[dot]pdf.
Anonymous, "Prolor and Yeda Enter Definitive License Agreement for Reversible PEGylation Technology," Jan. 18, 2011, pp. 1-3; Retrieved from the Internet at web[dot]archive[dot]org/web/20110123063420/ http://www[dot]news-medical[dot]net/news/20110118/PROLOR-and-Yeda-enter-definitive-license-agreement-for-Reversible-PEGYlation-technology[dot]aspx.
Anson et al., "The Gene Structure of Human Anti-Haemophilic Factor IX," *The EMBO Journal*, 3(5):1053-1060 (1984).
Askoy et al., "A Study of the Intracellular and Secreted Forms of the MUC2 Mucin from the PC/AA Intestinal Cell Line," *Glycobiology*, 9.7:739-746 (1999).
Banerji et al., "A Lymphocyte-Specific Cellular Enhancer is Located Downstream of the Joining Region in Immunoglobulin Heavy Chain Genes," *Cell*, 33:729-740 (1983).
Barker et al., "An Immunomagnetic-Base Method for the Purification of Ovarian Cancer Cells from Patient-Derived Ascites," *Gynecologic Oncology*, 82:57-63 (2001).
Beeley, *Glycoprotein and Proteoglycan Techniques*, Elsevier, pp. 69-72 (1985).
Bengtsson et al., "Treatment of Adults with Growth Hormone (GH) Deficiency with Recombinant Human GH," *J. Clin. Endocrinol. Metab.*, 76(2):309-317 (1993).
Berntorp et al., "The Pharmacokinetics of Clotting Factor Therapy," *Haemophilia*, 9:353-359 (2003).
Biller et al., "Effects of Once-Weekly Sustained-Release Growth Hormone: A Double-Blind, Placebo-Controlled Study in Adult Growth Hormone Deficiency," *The Journal of Clinical Endocrinology & Metabolism*, 96(6):1718-1726 (2002).
Bitter et al., "Expression and Secretion Vectors for Yeast," *Methods in Enzymol.*, 153:516-544 (1987).
Bjorkman et al., Pharmacokinetics of Coagulation Factors Clinical Relevance for Patients for Haemophilia, *Clin. Pharmacokinet.*, 40(11):815-832 (2001).
Bohl et al., "Improvement of Erythropoiesis in b-thalassemic Mice by Continuous Erythropoietin Delivery from Muscle," *Blood*, 95:2793-2798 (2000).
Boissel et al., "Erythropoietin Structure-Function Relationships," *The Journal of Biological Chemistry*, 268(21):15983-15993 (1993).
Booth et al., "The Use of a 'Universal' Yeast Expression Vector to Produce an Antigenic Protein of Mycobacterium leprae," *Immunol. Lett.*, 19:65-70 (1988).
Bouloux eta l., "First Human Exposure to FSH-CTP in Hypogonadotrophic Hypogonadal Males," *Human Reproduction*, 16(8):1592-1597 (2001).
Brisson et al., "Expression of a Bacterial Gene in Plants by Using a Viral Vector," *Nature*, 310:511-514 (1984).
Broglie et al., "Light-Regulated Expression of a Pea Ribulose-1,5-Bisphosphat Carboxylase Small Subunit Gene in Transformed Plant Cells," *Science*, 224:838-843 (1984).
Brunetti-Pierri et al., "Bioengineered Factor IX Molecules with Increased Catalytic Activity Improve the Therapeutic Index of Gene Therapy Vectors for Hemophilia B," *Human Gene Therapy*, 20.5:479-485 (2009).
Buchwald et al., "Long-Term, Continuous Intravenous Heparin Administration by an Implantable Infusion Pump in Ambulatory Patients with Recurrent Venous Thrombosis," *Surgery*, 88:507-516 (1980).

(56) References Cited

OTHER PUBLICATIONS

Butler et al., "The Beta-Subunit of Human Chorionic Gonadotrophin Exists as a Homodimer," *Journal of Molecular Endocrinology*, 22.2:185-192 (1999).
Byrne et al., "Multiplex Gene Regulation: A Two-Tiered Approach to Transgene Regulation in Transgenic Mice," *Proc. Natl. Acad. Sci. USA*, 86:5473-5477 (1989).
Calame et al., "Transcriptional Controlling Elements in the Immunoglobulin and T Cell Receptor Loci," *Adv. Immunol.*, 43:235-275 (1988).
Calo et al., "Enhancing the Longevity and in vivo Potency of Therapeutic Proteins: The Power of CTP," *Precision Medicine*, 1:1-8 (2015).
Carles-Bonnet et al., "H-Lys-Arg-Asn-Lys-Asn-Asn-OH is the Minimal Active Structure of Oxyntomodulin," *Peptides*, 17(3):557-561 (1996).
Cawley et al., "Developing Long-Acting Growth Hormone Formulations," *Clinical Endocrinology*, 79:305-309 (2013).
Chan et al., "Plasma Insulin-Like Growth Factor-I and Prostate Cancer Risk: A Prospective Study," *Science*, 279:563-566 (1998).
Chen et al., "Recombinant Carbohydrate Variant of Human Choriogonadotropin Beta-Subunit (hCG beta) Descarboxyl Terminus (115-145). Expression and Characterization of Carboxyl-Terminal Deletion Mutant of hCG Beta in the Baculovirus System," *Journal of Biological Chemistry*, 10:6246-6251 (1991).
Chen et al., "Modulating Antibody Pharmacokinetics Using Hydrophilic Polymers," *Expert Opinion on Drug Delivery*, 8.9:1221-1236 (2011).
Chen et al., "Glycoengineering Approach to Half-Life Extension of Recombinant Biotherapeutics," *Bioconjugate Chemistry*, 23.8:1524-1533 (2012).
Chihara, "Clinical Aspect of Growth Hormone Deficiency in Adults," Nihon Naika Gakkai zasshi. *The Journal of the Japanese Society of Internal Medicine*, 89(9):2010 (2000) with English Abstract.
Claxton et al., "A Systematic Review of the Associations Between Dose Regimens and Medication Compliance," *Clinical Therapeutics*, 23.8:1296-1310 (2001).
Cohen et al., "Oxyntomodulin Suppresses Appetite and Reduces Food Intake in Humans," *J. Clin. Endocrinol. Metab.*, 88(10):4696-4701 (2003).
Coleman et al., "Dosing Frequency and Medication Adherence in Chronic Disease," *Journal of Managed Care Pharmacy*, 18.,7:527-539 (2012).
Coruzzi et al., "Tissue-Specific and Light-Regulated Expression of a Pea Nuclear Gene Encoding the Small Subunit of Ribulose-1,5-Bisphosphate Carboxylase," *The EMBO Journal*, 3:1671-1680 (1984).
Cutfield et al., "Non-Compliance with Growth Hormone Treatment in Children is Common and Impairs Linear Growth," *PLoS One*, 6.1:e16223 (2011).
Dacambra et al., Structural Determinants for Activity of Glucagon-Like Peptide-2, *Biochemistry*, 39(30):8888-8894 (2000).
Dalton et al., "Over-Expression of Secreted Proteins from Mammalian Cell Lines," *Protein Science*, 23(5):517-525 (2014).
Database Geneseq [Online] Apr. 7, 2005, "Human Interferon Beta (without Signal Peptide)," XP002664024 retrieved from EBI Accession No. GSP:ADW02285, Database Accession No. ADW02285.
Davis et al., "Deletion of Clustered O-Linked Carbohydrates Does Not Impair Function of Low Density Lipoprotein Receptor in Transfected Fibroblasts," *J. Biol. Chem.*, 261(6):2828-2838 (1986).
Diao et al., "The molecular design and drug development of recombinant long-acting follicle stimulating hormone," *Acta Pharmaceutica Sinica* (abstract obtained online), 47(4):421-426 (2012) (Abstract only in English).
Diederichs et al., "Liposome in Kosmetika und Arzneimitteln," *Pharmazeutische Industrie*, 56.3:267-275 (1994).
Diness et al., "Effect of Recombinant Human FVIIA on Warfarin-Induced Bleeding in Rats," *Thrombosis Research*, 59.6:921-929 (1990).
Dong et al., "The Prolonged Half-Lives of New Erythropoietin Derivatives via Peptide Addition," *Biochemical Research Communications*, 339(1):380-385 (2006).
Drake et al., "Optimizing GH Therapy in Adults and Children," *Endocr.Rev.*, 22(4):425-450 (2001).
Dyson et al. (eds.), "Chapter 1. Introduction. The Mechanism of Action of Drug Substances," in *The Chemistry of Synthetic Drugs*, Publishing House MIR, Moscow, pp. 12-19 (1964).
Edlund et al., "Cell-Specific Expression of the Rat Insulin Gene: Evidence for Role of Two Distinct 5' Flanking Elements," *Science*, 230:912-916 (1985).
Edmunds et al., "Plasma Erythropoietin Levels and Acquired Cystic Disease of the Kidney in Patients Receiving Regular Haemodialysis Treatment," *Br. J. Haematol.*, 78(2):275-277 (1991).
Eldem et al., "Optimization of Spray-Dried and -Congealed Lipid Micropellets and Characterization of the Surface Morphology," *Pharm. Res.*, 8:47-54 (1991).
Eschbach et al., "Correction of the Anemia of End-Stage Rental Disease with Recombinant Human Erythropoietin," *The New England Journal of Medicine*, 316(2):73-78 (1987).
European Search Report for European Appln. No. 12179805.2 dated Nov. 9, 2011.
European Search Report for European Appln. No. 12150722.2 dated Jun. 4, 2012.
European Search Report for European Appln. No. 12179821.9 dated Nov. 12, 2012.
European Search Report for European Appln. No. 14196333.0 dated Mar. 2, 2015.
European Search Report for European Appln. No. 14197286.9 dated Mar. 2, 2015.
European Search Report for European Appln. No. 16187710.5 dated Oct. 14, 2016.
European Search Report for European Appln. No. 17161199.9 dated Aug. 7, 2017.
European Search Report for European Appln. No. 18150731.0 dated Feb. 27, 2018.
European Search Report for European Appln. 18198355.2 dated Mar. 13, 2019.
European Search Report for European Appln. No. 19205364 dated May 6, 2020.
European Search Report for European Appln. No. 20172836 dated Dec. 10, 2020.
European Search Report for European Appln. No. 20204439 dated Feb. 10, 2021.
European Search Report for European Appln. No. 21151437 dated Jun. 8, 2021.
Extended European Search Report for European Appln. No. 16811146.6 dated Jan. 8, 2019.
Fares et al., "Design of a Long-Acting Follitropin Agonist by Fusing the C-Terminal Sequence of the Chorionic Gonadotropin Beta Subunit to the Follitropin Beta Subunit," *Proc. Natl. Acad. Sci. USA*, 89(10):4304-4308 (1992).
Fares et al., "Growth Hormone (GH) Retardation of Muscle Damage Due to Immobilization in Old Rats. Possible Intervention with a New Long-Acting Recombinant GH," *Ann. NY Acad. Sci.*, 786:430-443 (1996).
Fares, "Yhe Role of O-Linked and N-Linked Oligosaccharides on the Structure-Function of Glycoprotein Hormones: Development of Agonists and Antagonists," *Biochimica et Biophysica Acta*, 1760. 4:560-567 (2006).
Fares et al., "Development of a Long-Acting Erythropoietin by Fusing the Carboxyl-Terminal Peptide of Human Chorionic Gonadotropin β-Subunit to the Coding Sequence of Human Erythropoietin," *Endocrinology*, 148.10:5081-5087 (2007).
Fares et al., "Designing a Long-Acting Human Growth Hormone (hGH) by Fusing the Carboxy-Terminal Peptide of Human Chorionic Gonadotropin B-Subunit to the Coding Sequence of hGH," *Endocrinology*, 151(9):4410-4417 (2010).
Fares et al., "Designing a Long Acting Erythropoietin by Fusing Three Carboxyl-Terminal Peptides of Human Chorionic Gonadotropin [beta] Subunit to the N-Terminal and C-Terminal Coding Sequence," *Int'l J. Cell Biol.*, 9(11):2021-2027 (2011).
Fayad et al., "Update of the M.D. Anderson Cancer Center Experience with Hyper-CVAD and Rituximab for the Treatment of Mantle Cell and Burkitt-Type Lymphomas," *Clin. Lymphoma Myeloma*, 8(Suppl. 2):S57-S62 (2007).

(56) References Cited

OTHER PUBLICATIONS

Fingl et al., "General Principles," *The Pharmacological Basis of Therapeutics*, Goodman et al.,, eds., pp. 1-46 (1975).
Fogarty, "Biological Rationale for New Drugs in the Bleeding Disorders Pipeline," ASH Education Program Book 2011.1:397-404 (2011).
Freshney, "Culture of Animal Cells: A Manual of Basic Technique," *Culture of Animal Cells, A Manual of Basic Technique*, Alan R. Liss, Inc. (New York), p. 4 (1983).
Fuentes-Prior et al., "Structural Basis for the Anticoagulant Activity of the Thrombin-Thrombomodulin Complex," *Nature*, 404(6777):518-525 (2000).
Furuhashi et al., "Fusing the Carboxy-Terminal Peptide of the Chorionic Gonadotropin (CG)-Subunit to the Common Alpha-Submit: Retention of O-Linked Glycosylation and Enhanced in vivo Bioactivity of Chimeric Human CG," *Molecular Endocrinology*, 9(1):54-63 (1995).
Furuhashi et al., "Processing of O-Linked Glycosylation in the Chimera Consisting of Alpha-Subunit and Carboxyl-Terminal Peptide of the Human Chorionic Gonadotropin Beta-Subunit is Affected by Dimer Formation with Follicle-Stimulating Hormone Beta-Subunit," *Endocrine Journal*, 51(1):53-59 (2004).
Gao et al., Erythropoietin Gene Therapy Leads to Autoimmune Anemia in Macaques, *Blood*, 103(9):3300-3302 (2004).
Garcia-Campayo et al., "Unmasking a New Recognition Signal for <i> O</i>-Linked Glycosylation in the Chorionic Gonadotropin β Subunit," *Molecular and Cellular Endocrinology*, 194.1:63-70 (2002).
Gardella et al., "Expression of Human Parathyroid Hormone-(I-84) in *Escherichia coli* as a Factor X-Cleavable Fusion Protein," *J. Biol. Chem.*, 265:15854-15859 (1990).
Gellerfors et al., "Characterisation of a Secreted Form of Recombinant Derived Human Growth Hormone, Expressed in *Escherichia coli* Colls," *J. Pharm. Biomed. Anal.*, 7(2):173-183 (1989).
Genbank Accession No. NP 002045 (version 1), Sep. 6, 2014.
Ghosh et al., "Activity and Regulation of Factor VIIa Analogs with Increased Potency at the Endothelial Cell Surface," *Journal of Thrombosis and Haemostasis*, 5.2:336-346 (2007).
Gilboa et al., "Transfer and Expression of Cloned Genes Using Retroviral Vectors," *Biotechniques*, 4:504-512 (1986).
Goodson, in "Medical Applications of Controlled Release," 2:115-138 (1984).
Guitton et al., "Influence of in vitro Non-Enzymatic Glycosylation on the Physicochemical Parameters of Type I Collagen," *Collagen and Related Research*, 4.4:253-264 (1984).
Gurley et al., "Upstream Sequences Required for Efficient Expression of a Soybean Heat Shock Gene," *Mol. Cell Biol.*, 6:559-565 (1986).
Hacke et al., "Intravenous Thrombolysis with Recombinant Tissue Plasminogen Activator for Acute Hemispheric Stroke. The European Cooperative Acute Stroke Study (ECASS)," *JAMA*, 274(13):1017-1025 (1995).
Hammerling et al., "In vitro Bioassay for Human Erythropoietin Based on Proliferative Stimulation of an Erythroid Cell Line and Analysis of Carbohydrate-Dependent Microheterogeneity," *Journal of Pharm. Biomed. Analysis*, 14(11):1455-1469 (1996).
Havron et al., "OR2, 8 Phase I PK&PD Profile of Long-Acting Bio-Better CTP Modified hGH (MOD-4023) in Healthy Volunteers," *Growth Hormone & IGF Research*, 20:S4-S5 (2010).
Heffernan et al., "Effects of Oral Administration of a Synthetic Fragment of Human Growth Hormone on Lipid Metabolism," *American Journal of Physiology-Endocrinology and Metabolism*, 279.3:E501-E507 (2000).
Hershkovitz et al., "In vitro and in vivo Characterization of MOD-4023, a Long-Acting Carboxy-Terminal Peptide (CTP)-Modified Human Growth Hormone," *Molecular Pharmaceuticals*, 13(2):631-639 (2016).
Houdebine, "The Methods to Generate Transgenic Animals and to Control Transgene Expression," *Journal of Biotechnology*, 98:145-160 (2002).

Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883 (1988).
International Search Report for Appln. No. PCT/US2007/002767 dated Feb. 15, 2008.
International Search Report for Appln. No. PCT/US2007/003014 dated Sep. 22, 2008.
International Search Report for Appln. No. PCT/IL2009/000700 dated Sep. 22, 2008.
International Search Report for Appln. No. PCT/IL2010/000532 dated Apr. 11, 2011.
International Search Report for Appln. No. PCT/IL2012/050288 dated Jan. 28, 2013.
International Search Report for Appln. No. PCT/IL2013/050107 dated Jul. 10, 2013.
International Search Report for Appln. No. PCT/IL2014/050910 dated Jan. 25, 2015.
International Search Report for Appln. No. PCT/IL2016/050645 dated Jan. 19, 2017.
International Search Report for Appln. No. PCT/IL2017/050645 dated Sep. 21, 2017.
International Search Report for Application No. PCT/IL2017/050784 dated Sep. 22, 2017.
International Preliminary Report on Patentability for PCT/IL2017/050645 dated Dec. 11, 2018.
International Preliminary Report on Patentability for PCT/IL2017/050784 dated Jan. 24, 2019.
International Search Report for Application No. PCT/IL2020/050769 dated Sep. 22, 2020.
Isgaard et al., "Effects of Local Administration of GH and IGF-1 on Longitudinal Bone Growth in Rats," *Am. J. Physiol.*, 250(4 Pt 1):E367-E372 (1986).
Jarrousse et al., "Oxyntomodulin (Glucagon-37) and its C-Terminal Octapeptide Inhibit Gastric Acid Secretion," *FEBS Lett.*, 188(1):81-84 (1985).
Joshi et al., "Recombinant Thyrotropic Containing a Beta-Subunit Chimera with the Human Chorionic Gonadotropin-Beta Carboxy-Terminus is Biologically Active, with a Prolonged Plasma Half-Life: Role of Carbohydrate in Bioactivity and Metabolic Clearance," *Endocrinology*, 136(9):3839-3848 (1995).
Kanda et al., "Genetic Fusion of an a-subunit Gene to the Follicle-Stimulating Hormone and Chorionic Gonadotropin-b Subunit Genes: Production of a Bifunctional Protein," *Molecular Endocrinology*, 13(11):1873-1881 (1999).
Kaseb et al., "Development and validation of an IGF-1-modified Child-Pugh score to risk-stratify hepatocellular carcinoma patients," *Egypt. J. Obes. Diabetes Endocrinol.* [serial online], 1:14-20 (2015).
Kelly et al., "Outcomes of Patients with Burkitt Lymphoma Older than Age 40 Treated with Intensive Chemotherapeutic Regimens," *Clin. Lymphoma Myeloma*, 9(4):307-310 (2009).
Kessler et al., "Structures of N-Glycosidic Carbohydrate Units of Human Chorionic Gonadotropin," *J. Biol. Chem.*, 254(16):7901-7908 (1979).
Kessler et al., "Structure and Location of the O-Glycosidic Carbohydrate Units of Human Chorionic Gonadotropin," *J. Biol. Chem.*, 254(16):7909-7908 (1979).
Kicman et al., "Human Chorionic Gonadotrophin and Sport," *British Journal of Sports Medicine*, 25.2:73-80 (1991).
Kieffer et a l., "Distribution of Glucagon Receptors on Hormone-Specific Endocrine Cells of Rat Pancreatic Islets," *Endocrinology*, 137(11):5119-5125 (1996).
Knudsen et al., "Small-Molecule Agonists for the Glucagon-Like Peptide 1 Receptor," *PNAS*, 104(3):937-942 (2007).
Kondratieva (ed.), "Chapter 1, Basic Concepts and Methodology of the Subject," in *Technology of Dosage Forms*, vol. 1, Pharmaceutical Institute, Moscow, pp. 5, 6, 74 (1991).
Kontermann, "Strategies for Extended Serum Half-Life of Protein Therapeutics," *Curr. Opin. Biotech.*, 22.6:868-876 (2011).
Kontermann, "Half-Life Modulating Strategies—An Introduction," *Therapeutic Proteins: Strategies to Modulate Their Plasma Half-Lives*, pp. 1-21 (2012).

(56) References Cited

OTHER PUBLICATIONS

Kotler et al., "Effects of Growth Hormone on Abnormal Visceral Adipose Tissue Accumulation and Dyslipidemia in HIV-Infected Patients," *Journal of Acquired Immune Deficiency Syndromes*, 35.3:239-252 (2004).

Krantz et al., "Specific Binding of Erythropoietin to Spleen Cells Infected with the Anemia Strain of Friend Virus," *Proc. Natl. Acad. Sci. USA*, 81(23):7574-7578 (1984).

Langer, "New Methods of Drug Delivery," *Science*, 249:1527-1533 (1990).

Larsen et al.,"Accumulation of Magnetic Iron Oxide Nanoparticles Coated with Variably Sized Polyethylene Glycol in Murine Tumors," *Nanoscale* 4.7:2352-2361 (2012).

Le et al., "Improved Vancomycin Dosing in Children Using Area Under the Curve Exposure," *Pediatr. Infect. Dis. J.*, 32:e155-e163 (2013).

Lee et al., "The Prolonged Half-Lives of New Erythropoietin Derivatives via Peptide Addition," *Biochem. Biophys. Res. Commun.*, 339(1):380-385 (2006).

Lentz et al., "Posttranslational Modification of the Carboxy-Terminal Region of the β Subunit of Human Chorionic Gonadotropin," *Biochemistry*, 23.22:5330-5337 (1984).

Li et al., "Bioassay of hGH .I. Weight Gain of Hypophysectomized Rats," *Yaowu Fenxi Zazhi*, 15(2):3-7 (1995) (Abstract only in English).

Lippin et al., "Human Erythropoietin Gene Therapy for Patients with Chronic Renal Failure," *Blood*, 106(7):2280-2286 (2005).

Littlewood, "Erythropoietin for the Treatment of Anemia Associated with Hematological Malignancy," *Hematol. Oncol.*, 19(1):19-30 (2001).

Lo et al., "The Effects of Recombinant Human Growth Hormone on Body Composition and Glucose Metabolism in HIV-Infected Patients with Fat Accumulation," *J. Clin. Endocrinol. Metab.*, 86(8):3480-3487 (2001).

Lopez-Berestein et al., "Treatment of Systemic Fungal Infections with Liposomal Amphotericin B," *Liposomes in the Therapy of Infectious Diseases and Cancer*, pp. 310-327 (1989).

Lopez-Berestein et al., "Treatment of Systemic Fungal Infections with Liposomal amphotericin B," *Arch. Intern. Med.*, 149(110):2533-2536 (1989).

Maheshwari et al., "Manipulation of Electrostatic and Saccharide Linker Interactions in the Design of Efficient Glycopolypeptide-Based Cholera Toxin Inhibitors," *Macromolecular Bioscience*, 10.1:68-81 (2010).

Maston et al., "Chorionic Gonadotropin Beta Subunit [*Homo sapiens*]," NCBI Accession No. AAL69705.1 (Apr. 3, 2002).

Matsumoto et al., "The Measurement of Low Levels of Factor VIII or Factor IX in Hemophilia A and Hemophilia B Plasma by Clot Waveform Analysis and Thrombin Generation Assay," *Journal of Thrombosis and Haemostasis*, 4:377-384 (2006).

Matsuo et al., "Thrombolysis by Human Tissue Plasminogen Activator and Urokinase in Rabbits with Experimental Pulmonary Embolus," *Nature*, 291(5816):590-591 (1981).

Maun et al., "Disulfide Locked Variants of Factor VIIa with a Restricted β-Strand Conformation Have Enhanced Enzymatic Activity," *Protein Science*, 14.5:1171-1180 (2005).

McAlister et al., "NMR Analysis of the N-Terminal SRCR Domain of Human CD5: Engineering of a Glycoprotein for Superior Characteristics in NMR Experiments," *Protein Engineering*, 11.10:847-853 (1998).

McNeil, "No Rest for Fatigue Researchers," *J. Natl Cancer Inst.*, 100(16):1129 (2008).

Meulien et al., "Increased Biological Activity of a Recombinant Factor IX Variant Carrying Alanine at Position+ 1," *Protein Engineering*, 3.7:629-633 (1990).

Milton et al., "The Delineation of a Decapeptide Gonadotropin-Releasing Sequence in the Carboxyl-Terminal Extension of the Human Gonadotropin-Releasing Hormone Precursor," *J. Biol. Chem.*, 261(36):16990-16997 (1986).

Morel, "Mouse Models of Human Autoimmune Diseases: Essential Tools that Require the Proper Controls," *PLoS Biology*, 2(8):e241 (2004).

Morgan et al., "The Amino Acid Sequence of Human Chorionic Gonadotropin. The Alpha Subunit and Beta Subunit," *J. Biol. Chem.*, 250(13):5247-5258 (1975).

Muleo et al., "Small Doses of Recombinant Factor VIIa in Acquired Deficiencies of Vitamin K Dependent Factors," *Blood, Coagulation & Fibrinolysis*, 10(8):521-522 (1999) (Abstract only in English).

Murray et al., "Dose Titration and Patient Selection Increases the Efficacy of GH Replacement in Severely GH Deficient Adults," *Clinical Endocrinology*, 50:749-757 (1999).

Musto, "The Roel of Recombinant Erythropoietin for the Treatment of Anemia in Multiple Myeloma," *Leuk. Lymphoma*, 29(3-4):283-291 (1998).

Mutter et al., "A New Base-Labile Anchoring Group for Polymer-Supported Peptide Synthesis," *Helvetica chimica acta*, 67.7:2009-2016 (1984).

Mutter et al., "Evolution versus Design: Template-Directed Self-Assembly of Peptides to Artificial Proteins (TASP)," *Chimia International Journal of Chemistry*, 54.10:552-557 (2000).

NCBI GenBank Accession No. AAL69702 (Apr. 3, 2002).

Nezu et al., "Treatment of Idiopathic Pituitary Dwarfism with Human Growth Hormone," *Journal of Nara Medical Association*, 40.1:16-22 (1989) (Abstract in English).

Ngo et al., "Computational Complexity, Protein Structure Protein Prediction and the Levinthal Paradox," in *Birkhauser The Protein Folding Problem and Tertiary Structure Prediction*, pp. 433-440 and 492-495 (1994).

Nguyen et al., "Stability and Characterization of Recombinant Human Relaxin," in *Formulation, Characterization, and Stability of Protein Drugs: Case Histories*, Pearlman et al., eds., Plenum Press, New York, pp. 247-274 (1996).

Office Action for Japanese Appln. No. 2014-523441 dated May 24, 2016.

Ogle et al., "Renal Effects of Growth Hormone. I. Renal Function and Kidney Growth," *Pediatr. Nephrol.*, 6:394-398 (1992).

Oosterhof et al., "Regulation of Whole Body Energy Homeostasis with Growth Hormone Replacement Therapy and Endurance Exercise," *Physiol. Genomics*, 43(12):739-748 (2011).

Pedrosa et al., "Selective Neoglycosylation Increases the Structural Stability of Vicilin, the 7S Storage Globulin from Pea Seeds," *Archives of Biochemistry and Biophysics*, 382.2:203-210 (2000).

Persson et al., "Rational Design of Coagulation Factor VIIa Variants with Substantially Increased Intrinsic Activity," *Proc. Natl. Acad. Sci. USA*, 98.24:13583-13588 (2001).

Persson et al., "Recombinant Coagulation Factor VIIa—from Molecular to Clinical Aspects for a Versatile Haemostatic Agent," *Thrombosis Research*, 125:483-489 (2010).

Peter et al., "Pharmacokinetic and pharmacodynamic Profile of a new sustained-release GH Formulation, LB03002, in children with GH deficiency," *European Journal of Endocrinology* (obtained online), 160:349-355 (2009).

Philips, "The Challenge of Gene Therapy and DNA Delivery," *J. Pharm. Pharmacology*, 53:1169-1174 (2001).

Pierce et al., "Glycoprotein Hormones: Structure and Function," *Annual Review of Biochemistry*, 50.1:465-495 (1981).

Pinkert et al., "An Albumin Enhancer Located 10 kb Upstream Functions Along with its Promoter to Direct Liver-Specific Expression in Transgenic Mice," *Genes Dev.*, 1:268-277 (1987).

Pocai et al., "Glucagon-Like Peptide 1/Glucagon Receptor Dual Agonism Reverses Obesity in Mice," *Diabetes*, 58:2258-2266 (2009).

Pokrovsky (ed.), "Medicinal Products," in *Popular Medical Encyclopedia*, 4th ed., p. 317 (1997).

Polizzotti et al., "Effects of Saccharide Spacing and Chain Extension on Toxin Inhibition by Glycopolypeptides of Well-Defined Architecture," *Macromolecules*, 40.20:7103-7110 (2007).

Poreddy et al., "Exogenous Fluorescent Tracer Agents Based on Pegylated Pyrazine Dyes for Real-Time Point-of-Care Measurement of Glomerular Filtration Rate," *Bioorganic & Medicinal Chemistry*, 20.8:2490-2497 (2012).

(56) References Cited

OTHER PUBLICATIONS

Puett et al., "Structure-Function Relationships of the Luteinizing Hormone Receptor," *Annals of the NY Academy of Sciences*, 1061(1):41-54 (2005).
Rebois et al., "Hydrodynamic Properties of the Gonadotropin Receptor from a Murine Leydig Tumor Cell Line are Altered by Desensitization," *Biochemistry*, 26.20:6422-6428 (1987).
Reichel, "Sarcosyl-Page: A New Electrophoretic Method for the Separation and Immunological Detection of PEGylated Proteins," *Protein Electrophoresis*, Humana Press, 65-79 (2012).
Reiter et al., "A Multicenter Study of the Efficacy and Safety of Sustained Release GH in the Treatment of Naive Pediatric Patients with GH Deficiency," *J. Clin. Endocrinol. Metab.*, 86(10):4700-4706 (2001).
Ronzi et al., "Optimisation of a Freeze-Drying Process of High Purity Factor VIII and Factor IX Concentrates," *Chemical Engineering and Processing*, 42:751-757 (2003).
Rosario, "Normal Values of Serum IGF-1 in Adults: Results from a Brazilian Population," *Arquivos Brasileiros de Endocrinologia & Metabologia*, 54(5):477-481 (2010).
Rudman et al., "Effects of Human Growth Hormone in Men over 60 Years Old," *N. Engl. J. Med.*, 323(1):1-6 (1990).
Runge et al., "Different Domains of the Glucagon and Glucagon-Like Peptide-1 Receptors Provide the Critical Determinants of Ligand Selectivity," *British Journal of Pharmacology*, 138:787-794 (2003).
Russell et al., "Local Injections of Human or Rat Growth Hormone or of Purified Human Somatomedin-C Stimulate Unilateral Tibial Epiphyseal Growth in Hypophysectomized Rats," *Endocrinology*, 116(6):2563-2567 (1985).
Sambrook et al., *Molecular Cloning: A Laboratory Manual*, Cold Spring Harbor Laboratory Press, Cold Spring Harbor, New York (2001).
Saudek et al., "A Preliminary Trial of the Programmable Implantable Medication System for Insulin Delivery," *N. Engl. J. Med.*, 321:574 (1989).
Schein, "The Shape of the Messenger: Using Protein Structure Information to Design Novel Cytokine-Based Therapeutics," *Current Pharmaceutical Design*, 8(24):2113-2129 (2002) (Abstract).
Scheuttrumpf et al., "Factor IX Variants Improve Gene Therapy Efficacy for Hemophilia B," *Blood*, 105.6:2316-2323 (2005).
Schneider, "GMP Requirements for Master and Working Cell Bank," *Pharmazeutische Industrie*, 67(11):1366-1369 (2005).
Schulte, "Half-Life Extension through Albumin Fusion Technologies," *Thrombosis Research*, 124(Suppl. 2):S6-S8 (2009).
Sefton, "Implantable Pumps," *Critical Reviews in Biomedical Engineering*, 14.3:201-240 (1986).
Shechter et al., "Reversible PEGylation of Peptide YY3-36 Prolongs its Inhibition of Food Intake in Mice," *FEBS Lett.*, 579(11):2439-2444 (2005).
Sheffield et al., "Effects of Genetic Fusion of Factor IX to Albumin on in vivo Clearance in Mice and Rabbits," *British Journal of Haematology*, 126:565-573 (2004).
Silverman et al., "A Long-Acting Human Growth Hormone(Nutropin Depot): Efficacy and Safety Following Two Years of Treatment in Children with Growth Hormone Deficiency," *J. Pediatr. Endocrinol. Metab.*, 15(Suppl. 2):715-722 (2022).
Smeland et al., "Treatment of Burkitt's/Burkitt-Like Lymphoma in Adolescents and Adults: A 20-Year Experience from the Norwegian Radium Hospital with the Use of Three Successive Regimens," *Ann. Oncol.*, 15(7):1072-1078 (2004).
Srour et al., "Regulation of Human Factor IX Expression Using Doxycycline-Inducible Gene Expression System," *Thromb. Haemost.*, 90:398-405 (2003).
Stuart et al., "Polycythemia Vera," *Am. Fam. Physician*, 69(9):2139-2144 (2004).
Studier et al., "Use of T7 RNA Polymerase to Direct Expression of Cloned Genes," *Methods of Enzymol.*, 185:60-89 (1990).
Su et al., "Curcumin Inhibits Human Lung Cell Carcinoma Cancer Tumour Growth in a Murine Xenograft Model," *Phytother. Res.*, 24:189-191 (2010).
Sugahara et al., "Characterization of the O-Glycosylation Sites in the Chorionic Gonadotropin β Subunit in vivo Using Site-Directed Mutagenesis and Gene Transfer," *Journal of Biological Chemistry*, 271.34:20797-20804 (1996).
Supplementary European Search Report for European Appln. No. 07749922.6 dated Oct. 8, 2009.
Supplementary European Search Report for European Appln. No. 09797630.2 dated Dec. 5, 2011.
Supplementary European Search Report for European Appln. No. 10796803.4 dated Feb. 28, 2013.
Supplementary European Search Report for European Appln. No. 12819794.4 dated Feb. 24, 2015.
Supplementary European Search Report for European Application No. 13749077.7 dated Oct. 22, 2015.
Supplementary European Search Report for European Appln. No. 14856666.4 dated May 3, 2017.
Supplementary European Search Report for European Application No. 16811146.6 completed Dec. 14, 2018.
Takamatsu et al., "Expression of Bacterial Chloramphenicol Acetyltransferase Gene in Tobacco Plants Mediated by TMV-RNA," *EMBO J.*, 6:307-311 (1987).
Takeya et al., "Bovine Factor VII. Its Purification and Complete Amino Acid Sequence," *Journal of Biological Chemistry*, 236(29):14868-14877 (1988).
Tape et al., "Apolipoprotein AI and Apolipoprotein SAA Half-Lives During Acute Inflammation and Amyloidogenesis," *Biochemica et Biophysica Acta*, 1043(3):295-300 (1990).
Tharakan et al., "Emerging Therapies in the Treatment of 'Diabesity': Beyond GLP-1," *Trends Pharmacol. Sci.*, 32(1):8-15 (2011).
The Merck Index: An Encyclopedia of Chemicals, Drugs, and Biologicals, 15th ed., Item No. 4561, Gonadotropin, pp. 835-836 (2013).
Treat et al., "Liposome Encapsulated Doxorubicin—Preliminary Results of Phase I and Phase II Trials" in: G. Lopez-Berestein et al., eds., *Liposomes in the Therapy of Infectious Diseases and Cancer*, Alan R. Liss (New York), pp. 353-365 (1989).
Uenalp et al., "Factor VII Deficiency Associated with Valproate Treatment," *Pediatrics International*, 50(3):403-405 (2008) (Abstract).
Venn et al., "Biosynthesis and Metabolism in vivo of Intervertebral-Disc Proteoglycans in the Mouse," *Biochem. J.*, 215:217-225 (1983).
Verhoef et al., "Recombinant Human Erythropoietin for the Treatment of Anemia in the Myelodysplastic Syndromes: A Clinical and Erythrokinetic Assessment," *Ann. Hematol.*, 64(1): 16-21 (1992).
Vyshkovsy (ed.), "Description of Medicinal Products and Active Substances," in *State Register of Medicines of Russia. SRM. Medicines Encyclopedia*, Moscow, Issue 15, p. 745 (2006).
Weiss et al., "Noncompliance in Neurologic Patients," *Current Treatment Options in Neurology*, 7:419-425 (2005).
Weissbach et al., "Methods for Plant Molecular Biology," Selected Methods in Enzymology (USA), Section VIII; pp. 421-463 (1988).
Wells, "Additivity of Mutational Effects in Proteins," *Biochemistry*, 29:8509-8517 (1990).
White et al., "Mammalian Recombinant Coagulation Proteins: Structure and Function," *Transfus. Sci.*, 19(2):177-189 (1998).
Wildt et al., "The Humanization of N-Glycosylation Pathways in Yeast," *Nature Reviews Microbiology*, 3.2:119-128 (2005).
Wilken et al., "A Novel Four-Amino Acid Determinant Defines Conformational Freedom within Chorionic Gonadotropin β-Subunits," Biochemistry, 46.14:4417-4424 (2007).
Wilson et al., "Assessing Annotation Transfer for Genomics: Quantifying the Relations Between Protein Sequence, Structure and Function through Traditional and Probabilistic Scores," *Journal of Molecular Biology*, 297(1):233-249 (2000).
Winoto et al., "A Novel, Inducible and T Cell-Specific Enhancer Located at the 3' End of the T Cell Receptor Alpha Locus," *EMBO J.*, 8:729-733 (1989).
Wynne et al., "Subcutaneous Oxyntomodulin Reduces Body Weight in Overweight and Obese Subjects a Double-Blind, Randomized, Controlled Trial," *Diabetes*, 54.8:2390-2395 (2005).

(56) References Cited

OTHER PUBLICATIONS

Yefenof et al., "Interferon Amplifies Complement Activation by Burkitt's Lymphoma Cells," *Nature*, 313(6004):68 (1985).

Yin et al., "Recombinant Human Growth Hormone Replacement Therapy in HIV-Associated Wasting and Visceral Adiposity," *Exper. Rev. Anti-Infect. Ther.*, 3(5):727-736 (2005).

Yong et al., "The Molecular Design and Drug Development of Recombinant Long-Acting Follicle Stimulating Hormone," Institute of Molecular Medicine, Huaqiao University, Quanzhou, China and Centre of Reproduction and Genomics, AgResearch, Invermay, Mosgiel, New Zealand. Acta Pharmaceutica Sinica, 47(4):421-426 (Abstract only) (2012).

Zheng et al., "The Impact of Glycosylation on Monoclonal Antibody Conformation and Stability," *Mabs*, 3(6):568-576 (2011).

Zhong et al., "The N-Terminal Epidermal Growth Factor-Like Domain in Factor IX and Factor X Represents an Important Recognition Motif for Binding to Tissue Factor," *J. Biol. Chem.*, 277(5):3622-3631 (2002).

Zhong et al., "Biological Insights into Therapeutic Protein Modifications throughout Trafficking and their Biopharmaceutical Applications," *Intl. J. Cell Biol.*, vol. 2013, Article ID 273086, 19 pp. (2013).

\* cited by examiner

| DS Batch Number | Manufacturing Site | Manufacturing Date | Clone | Batch Size (net) | Use |
|---|---|---|---|---|---|
| EN648-01-08-005 | Xcellerex | Oct 2008 | 2 | 200L | Acute toxicity and PK studies 1592-001 and 1592-002, Used to prepare reference standard RS0809 |
| EN648-01-09-002 | Xcellerex | Feb 2009 | 2 | 500L | 4-week toxicity studies 1592-003 and 1592-004 |
| 648-01-09-003B | Xcellerex | Apr 2009 | 2 | 700L | Phase I Clinical Trial CP-4-001 Phase II Clinical Trial CP-4-003 |
| EN648-01-10-014A | Xcellerex | October 2010 | 28 | 200L | 26-week chronic toxicity study in monkeys (1592-006), Reproductive/developmental toxicity in rats (1592-007, 1592-008, 1592-009) |
| EN648-01-10-019A | Xcellerex | December 2010 | 28 | 700L | 26-week chronic toxicity study in monkeys (1592-006), Reproductive/developmental toxicity in rats (1592-007, 1592-008, 1592-009) Used to prepare reference standard RS0911 |
| 648-01-11-003 | Xcellerex | June 2011 | 28 | 700L | Phase II Pediatric Clinical Trial |
| 648-01-11-003A | Xcellerex | June 2011 | 28 | 700L | Phase II Pediatric Clinical Trial |
| GMP-1 | Rentschler | January 2012 | 28 | 700L | Phase II Pediatric Clinical Trial |
| GMP-2 | Rentschler | May 2012 | 28 | 700L | Phase II Pediatric Clinical Trial |

Gray mark : DS batches at 20 and 40 mg/ml manufactured from the same GMP 700L scale batch

FIGURE 24

| Analytical method | Acceptance criteria | Xc. (DS)/Sc. (DP) 4-11-X003A-S1 | RB (DS) 155C011001 |
|---|---|---|---|
| SE-HPLC (area-%) | HMWS ≤ 8.0% | 1.7 | <0.9 |
| | Monomer ≥ 92% | 98.3 | >99.1 |
| | Dimer: Report result | 0.9 | 0.3 |
| | Polymers: Report result | 0.8 | <0.6 |
| RP-HPLC (area-%) | Total related forms: ≤ 6 area-% | 3.1 | 2.7 |
| | Main peak: ≥ 94 area-% | 96.9 | 97.3 |
| | Any related forms > 1.0 area-%: Report result | 2.8 (related form 3: 1.1 related form 4: 1.7) | 1.7 (related form 4: 1.7) |

FIGURE 29

Stability results of GMP1 (RB)
% Main Peak

| Incubation time (m) | -70C | 5C | 25C |
|---|---|---|---|
| 0 | 97.25 | 97.25 | 97.25 |
| 0.5 | | | 92.9 |
| 1 | 97.1 | 95.9 | 91 |
| 3 | 97.2 | 94.9 | 86.4 |

Stability results of XCLX (tested at RB)
% Main Peak

| Incubation time (m) | -70C | 5C | 25C |
|---|---|---|---|
| 0 | 96.9 | 96.9 | 96.9 |
| 0.5 | | | 94.6 |
| 1 | | | 93.6 |
| 3 | | | 89.8 |

| Incubation time (m) | %Peak 3 | | |
|---|---|---|---|
|  | -70C | 5C | 25C |
| 0 | 0.72 | 0.72 | 0.72 |
| 0.5 |  |  | 1.1 |
| 1m | 0.7 | 0.7 | 1.6 |
| 3m | 0.7 | 0.8 | 4.3 |

| Incubation time (m) | %Peak 3 | | |
|---|---|---|---|
|  | -70C | 5C | 25C |
| 0 | 1.1 | 1.1 | 1.1 |
| 0.5 |  |  | 1.4 |
| 1 |  |  | 2 |
| 3 |  |  | 4.5 |

RB
% Peak 5

| Incubation time (m) | -70C | 5C | 25C |
|---|---|---|---|
| 0 | 1.72 | 1.72 | 1.72 |
| 0.5 | | | 4.9 |
| 1m | 1.9 | 2.7 | 5.8 |
| 3m | 1.7 | 3.3 | 6.9 |

XCLX
% Peak 5

| Incubation time (m) | -70C | 5C | 25C |
|---|---|---|---|
| 0 | 1.7 | 1.7 | 1.7 |
| 0.5 | | | 3.7 |
| 1m | | | 4 |
| 3m | | | 4.6 |

| Lane | Sample name | [µg] | Gel |
|---|---|---|---|
| 1 | Milli-Q Water | - | |
| 2 | Serva IEF Marker pH 3-10 | N/A | |
| 3 | MOD-4023 reference standard (SR-929KU.2) | 10 | |
| 4 | Xcellerex/Scigen MOD-4023 4-09-X003B-S1 | 10 | |
| 5 | Xcellerex/Scigen MOD-4023 4-09-X003B-S2 | 10 | |
| 6 | Xcellerex MOD-4023 EN648-01-10-014 A | 10 | |
| 7 | Xcellerex MOD-4023 EN648-01-10-019 A | 10 | |
| 8 | Xcellerex/Scigen MOD-4023 4-11-X003A-S1 | 10 | |
| 9 | Rentschler Biotechnologie MOD-4023 155C011001 | 10 | |
| 10 | Serva IEF Marker pH 3-10 | N/A | |

FIGURE 35A

| Lane | SR-Nr. / SP-Nr. / Analysen-Nr. / Sample ID | Sample name | [µg/lane] | Colloidal Blue – Staining |
|---|---|---|---|---|
| 1 | - | Blank | - | |
| 2 | SR-206Pt.0 | Serva IEF Marker pH 3-10 | N/A | |
| 3 | SR-929SI.1 | MOD-4023 reference standard | 10 | |
| 4 | SR-929KU.2 | MOD-4023 reference standard | 10 | |
| 5 | SP1061/1 / 200041013 | PRA_SP001061/1_5°C, t= 3 months | 10 | |
| 6 | SP1061/1 / 200041017 | PRA_SP001061/1_25°C/60% RH, t= 3 months | 10 | |
| 7 | SP1062 / 1201865 | PRA MOD-4023 (40 mg/mL) Comparability study Xcellerex batch, Ch.: 648-01-11-003A, 25°C±2°C, t= 3 months | 10 | |
| 8 | - | Blank | - | |
| 9 | SR-206Pt.0 | Serva IEF Marker pH 3-10 | N/A | |
| 10 | - | Blank | - | |

FIGURE 35B

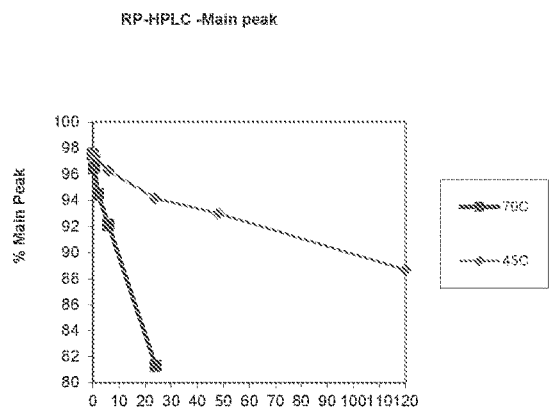
FIGURE 36A
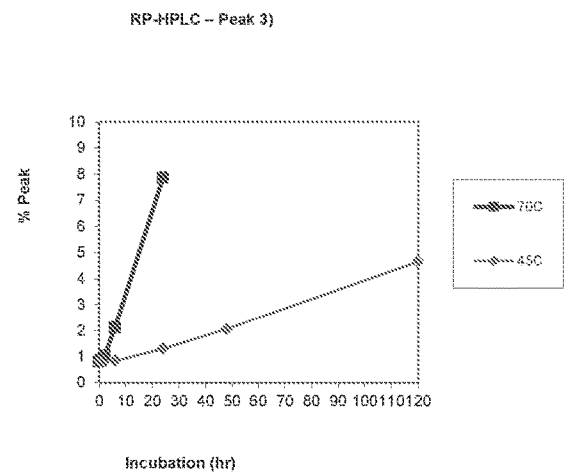
FIGURE 36B
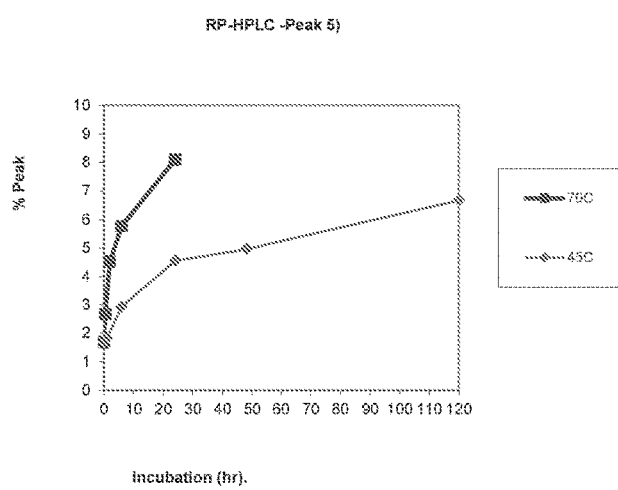
FIGURE 36C
| Storage Temp | Hours at Incubation Temp. | %Main Peak | Peak at 21-22min | Peak at 25-26min |
|---|---|---|---|---|
| 45°C | 0 | 97.50 | 0.81 | 1.69 |
| | 1 | 97.40 | 0.77 | 1.83 |
| | 6 | 96.24 | 0.83 | 2.93 |
| | 24 | 94.15 | 1.30 | 4.55 |
| | 48 | 92.99 | 2.06 | 4.96 |
| | 120 | 88.68 | 4.65 | 6.67 |
| 70°C | 0 | 97.50 | 0.81 | 1.69 |
| | 0.5 | 96.48 | 0.85 | 2.67 |
| | 2 | 94.46 | 1.02 | 4.52 |
| | 6 | 92.12 | 2.12 | 5.77 |
| | 24 | 81.29 | 7.87 | 8.09 |
FIGURE 36D

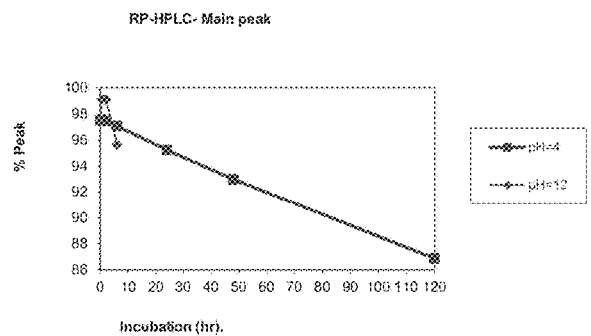
FIGURE 37A
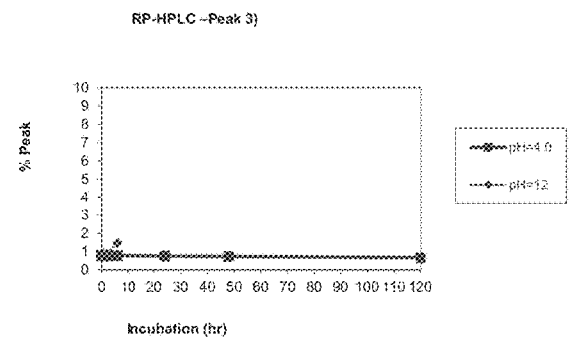
FIGURE 37B
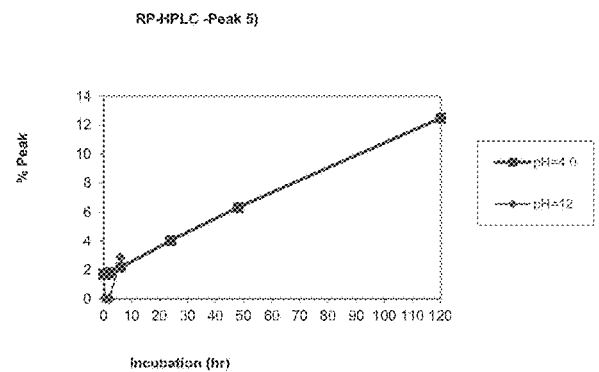
FIGURE 37C
| pH | Incubation time (hr) | %Main Peak | Peak 3 | Peak 5 |
|---|---|---|---|---|
| pH=12 | 0 | 97.51 | 0.79 | 1.70 |
|  | 0.5 | 99.14 | 0.86 | 0.00 |
|  | 2 | 99.11 | 0.89 | 0.00 |
|  | 6 | 95.65 | 1.48 | 2.86 |
| pH=4.0 | 0 | 97.51 | 0.79 | 1.70 |
|  | 0.5 | 97.57 | 0.75 | 1.68 |
|  | 2 | 97.46 | 0.74 | 1.80 |
|  | 6 | 97.08 | 0.77 | 2.16 |
|  | 24 | 95.24 | 0.74 | 4.02 |
|  | 48 | 92.97 | 0.72 | 6.31 |
|  | 120 | 86.86 | 0.65 | 12.49 |
FIGURE 37D Tested samples:
RB – 40 mg/ml, pH=5.9
RB - 10 mg/ml, pH=6.2
XCLX - 40 mg/ml, pH=6.2

% Mian Peak

| Incubation time (m) | RB 40 mg/ml pH=5.9 | RB 10 mg/ml pH=6.2 | XCLX 40 mg/ml pH=6.2 |
|---|---|---|---|
| 0 | 97.3 | 97.3 | 96.9 |
| 0.5 | 92.9 | 95.5 | 94.5 |
| 1 | 91 | | 93.5 |
| 3 | 86.4 | | 89.8 |

% Peak 3

| Incubation time (m) | RB 40 mg/ml pH=5.9 | RB 10 mg/ml pH=6.2 | XCLX 40 mg/ml pH=6.2 |
|---|---|---|---|
| 0 | 0.72 | 0.7 | 1.1 |
| 0.5 | 1.1 | 1.2 | 1.4 |
| 1 | 1.6 | | 2 |
| 3 | 4.3 | | 4.5 |

% Peak 5

| Incubation time (m) | RB 40 mg/ml pH=5.9 | RB 10 mg/ml pH=6.2 | XCLX 40 mg/ml pH=6.2 |
|---|---|---|---|
| 0 | 1.72 | 1.7 | 1.7 |
| 0.5 | 4.9 | 2.8 | 3.7 |
| 1 | 5.8 | | 4 |
| 3 | 6.9 | | 4.6 |

RB % peak 7

| Incubation time (m) | RB 40 mg/ml pH=5.9 | RB 10 mg/ml pH=6.2 | XCLX 40 mg/ml pH=6.2 |
|---|---|---|---|
| 0 | 0 | 0 | 0 |
| 0.5 | 0.6 | 0.1 | 0 |
| 1m | 1 | | 0 |
| 3m | 1.3 | | 0 |

FIGURE 39

SEQUENCE LISTING

```
<160> NUMBER OF SEQ ID NOS: 50

<210> SEQ ID NO 1
<211> LENGTH: 221
<212> TYPE: PRT
<213> ORGANISM: Homo sapiens

<400> SEQUENCE: 1

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160
```

-continued

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln
    210                 215                 220

<210> SEQ ID NO 2
<211> LENGTH: 249
<212> TYPE: PRT
<213> ORGANISM: Homo sapiens

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ser Ser Ser
    210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
                245

<210> SEQ ID NO 3
<211> LENGTH: 277
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
1               5                   10                  15

Leu Ser Leu Pro Leu Gly Leu Pro Val Gly Ser Ser Ser Lys
            20              25              30

Ala Pro Pro Ser Leu Pro Ser Pro Ser Arg Leu Pro Gly Pro Ser
        35              40              45

Asp Thr Pro Ile Leu Pro Gln Ala Pro Pro Arg Leu Ile Cys Asp Ser
        50              55              60

Arg Val Leu Glu Arg Tyr Leu Leu Glu Ala Lys Glu Ala Glu Asn Ile
65              70              75              80

Thr Thr Gly Cys Ala Glu His Cys Ser Leu Asn Glu Asn Ile Thr Val
                85              90              95

Pro Asp Thr Lys Val Asn Phe Tyr Ala Trp Lys Arg Met Glu Val Gly
        100             105             110

Gln Gln Ala Val Glu Val Trp Gln Gly Leu Ala Leu Leu Ser Glu Ala
        115             120             125

Val Leu Arg Gly Gln Ala Leu Leu Val Asn Ser Ser Gln Pro Trp Glu
130             135             140

Pro Leu Gln Leu His Val Asp Lys Ala Val Ser Gly Leu Arg Ser Leu
145             150             155             160

Thr Thr Leu Leu Arg Ala Leu Gly Ala Gln Lys Glu Ala Ile Ser Pro
                165             170             175

Pro Asp Ala Ala Ser Ala Ala Pro Leu Arg Thr Ile Thr Ala Asp Thr
        180             185             190

Phe Arg Lys Leu Phe Arg Val Tyr Ser Asn Phe Leu Arg Gly Lys Leu
        195             200             205

Lys Leu Tyr Thr Gly Glu Ala Cys Arg Thr Gly Asp Arg Ser Ser Ser
210             215             220

Ser Lys Ala Pro Pro Ser Leu Pro Ser Pro Ser Arg Leu Pro Gly
225             230             235             240

Pro Ser Asp Thr Pro Ile Leu Pro Gln Ser Ser Ser Lys Ala Pro
                245             250             255

Pro Pro Ser Leu Pro Ser Pro Ser Arg Leu Pro Gly Pro Ser Asp Thr
        260             265             270

Pro Ile Leu Pro Gln
        275

<210> SEQ ID NO 4
<211> LENGTH: 387
<212> TYPE: PRT
<213> ORGANISM: Homo sapiens

<400> SEQUENCE: 4

Met Gly Val His Glu Cys Pro Ala Trp Leu Trp Leu Leu Ser Leu
1               5               10              15

Leu Ser Leu Pro Leu Gly Leu Pro Val Leu Gly Ala Pro Pro Arg Leu
            20              25              30

Ile Cys Asp Ser Arg Val Leu Glu Arg Tyr Leu Leu Glu Ala Lys Glu
        35              40              45

Ala Glu Asn Ile Thr Thr Gly Cys Ala Glu His Cys Ser Leu Asn Glu
        50              55              60

Asn Ile Thr Val Pro Asp Thr Lys Val Asn Phe Tyr Ala Trp Lys Arg
65              70              75              80

Met Glu Val Gly Gln Gln Ala Val Glu Val Trp Gln Gly Leu Ala Leu
                85              90              95

Leu Ser Glu Ala Val Leu Arg Gly Gln Ala Leu Leu Val Asn Ser Ser
        100             105             110

```
Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ala Pro Pro
210                 215                 220

Arg Leu Ile Cys Asp Ser Arg Val Leu Glu Arg Tyr Leu Leu Glu Ala
225                 230                 235                 240

Lys Glu Ala Glu Asn Ile Thr Thr Gly Cys Ala Glu His Cys Ser Leu
                245                 250                 255

Asn Glu Asn Ile Thr Val Pro Asp Thr Lys Val Asn Phe Tyr Ala Trp
            260                 265                 270

Lys Arg Met Glu Val Gly Gln Gln Ala Val Glu Val Trp Gln Gly Leu
        275                 280                 285

Ala Leu Leu Ser Glu Ala Val Leu Arg Gly Gln Ala Leu Leu Val Asn
290                 295                 300

Ser Ser Gln Pro Trp Glu Pro Leu Gln Leu His Val Asp Lys Ala Val
305                 310                 315                 320

Ser Gly Leu Arg Ser Leu Thr Thr Leu Leu Arg Ala Leu Gly Ala Gln
                325                 330                 335

Lys Glu Ala Ile Ser Pro Pro Asp Ala Ala Ser Ala Ala Pro Leu Arg
            340                 345                 350

Thr Ile Thr Ala Asp Thr Phe Arg Lys Leu Phe Arg Val Tyr Ser Asn
        355                 360                 365

Phe Leu Arg Gly Lys Leu Lys Leu Tyr Thr Gly Glu Ala Cys Arg Thr
370                 375                 380

Gly Asp Arg
385

<210> SEQ ID NO 5
<211> LENGTH: 221
<212> TYPE: PRT
<213> ORGANISM: Homo sapiens

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
            20                  25                  30

Ala Pro Pro Pro Ser Leu Pro Ser Pro Ser Arg Leu Pro Gly Pro Ser
        35                  40                  45

Asp Thr Pro Ile Leu Pro Gln Ala Pro Pro Arg Leu Ile Cys Asp Ser
    50                  55                  60

Arg Val Leu Glu Arg Tyr Leu Leu Glu Ala Lys Glu Ala Glu Asn Ile
65                  70                  75                  80

Thr Thr Gly Cys Ala Glu His Cys Ser Leu Asn Glu Asn Ile Thr Val
```

```
                    85                  90                  95
Pro Asp Thr Lys Val Asn Phe Tyr Ala Trp Lys Arg Met Glu Val Gly
            100                 105                 110
Gln Gln Ala Val Glu Val Trp Gln Gly Leu Ala Leu Leu Ser Glu Ala
            115                 120                 125
Val Leu Arg Gly Gln Ala Leu Leu Val Asn Ser Ser Gln Pro Trp Glu
        130                 135                 140
Pro Leu Gln Leu His Val Asp Lys Ala Val Ser Gly Leu Arg Ser Leu
145                 150                 155                 160
Thr Thr Leu Leu Arg Ala Leu Gly Ala Gln Lys Glu Ala Ile Ser Pro
                165                 170                 175
Pro Asp Ala Ala Ser Ala Ala Pro Leu Arg Thr Ile Thr Ala Asp Thr
            180                 185                 190
Phe Arg Lys Leu Phe Arg Val Tyr Ser Asn Phe Leu Arg Gly Lys Leu
        195                 200                 205
Lys Leu Tyr Thr Gly Glu Ala Cys Arg Thr Gly Asp Arg
210                 215                 220

<210> SEQ ID NO 6
<211> LENGTH: 249
<212> TYPE: PRT
<213> ORGANISM: Homo sapiens

<400> SEQUENCE: 6

Met Gly Val His Glu Cys Pro Ala Trp Leu Trp Leu Leu Ser Leu
1               5                   10                  15
Leu Ser Leu Pro Leu Gly Leu Pro Val Leu Gly Ser Ser Ser Lys
            20                  25                  30
Ala Pro Pro Pro Ser Leu Pro Ser Pro Ser Arg Leu Pro Gly Pro Ser
        35                  40                  45
Asp Thr Pro Ile Leu Pro Gln Ala Pro Arg Leu Ile Cys Asp Ser
    50                  55                  60
Arg Val Leu Glu Arg Tyr Leu Leu Glu Ala Lys Glu Ala Glu Asn Ile
65                  70                  75                  80
Thr Thr Gly Cys Ala Glu His Cys Ser Leu Asn Glu Asn Ile Thr Val
                85                  90                  95
Pro Asp Thr Lys Val Asn Phe Tyr Ala Trp Lys Arg Met Glu Val Gly
            100                 105                 110
Gln Gln Ala Val Glu Val Trp Gln Gly Leu Ala Leu Leu Ser Glu Ala
            115                 120                 125
Val Leu Arg Gly Gln Ala Leu Leu Val Asn Ser Ser Gln Pro Trp Glu
        130                 135                 140
Pro Leu Gln Leu His Val Asp Lys Ala Val Ser Gly Leu Arg Ser Leu
145                 150                 155                 160
Thr Thr Leu Leu Arg Ala Leu Gly Ala Gln Lys Glu Ala Ile Ser Pro
                165                 170                 175
Pro Asp Ala Ala Ser Ala Ala Pro Leu Arg Thr Ile Thr Ala Asp Thr
            180                 185                 190
Phe Arg Lys Leu Phe Arg Val Tyr Ser Asn Phe Leu Arg Gly Lys Leu
        195                 200                 205
Lys Leu Tyr Thr Gly Glu Ala Cys Arg Thr Gly Asp Arg Ser Ser Ser
    210                 215                 220
Ser Lys Ala Pro Pro Pro Ser Leu Pro Ser Pro Ser Arg Leu Pro Gly
225                 230                 235                 240
```

Pro Ser Asp Thr Pro Ile Leu Pro Gln
            245

<210> SEQ ID NO 7
<211> LENGTH: 25
<212> TYPE: DNA
<213> ORGANISM: Artificial
<220> FEATURE:
<223> OTHER INFORMATION: Forward primer for EPO-CTP constructs

<400> SEQUENCE: 7
aatctagagg tcatcatggg ggtgc                                    25

<210> SEQ ID NO 8
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 8
attgcggccg cggatccaga agacctttat tg                            32

<210> SEQ ID NO 9
<211> LENGTH: 25
<212> TYPE: DNA
<213> ORGANISM: Artificial
<220> FEATURE:
<223> OTHER INFORMATION: Reverse primer for EPO-CTP constructs

<400> SEQUENCE: 9
taaatattgg ggtgtccgag ggccc                                    25

<210> SEQ ID NO 10
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 10
ccaatattac cacaagcccc accacgcctc at                            32

<210> SEQ ID NO 11
<211> LENGTH: 35
<212> TYPE: DNA
<213> ORGANISM: Artificial
<220> FEATURE:
<223> OTHER INFORMATION: Reverse primer for EPO-CTP constructs

<400> SEQUENCE: 11
tgcggccgcg gatccttatc tgtcccctgt cctgc                         35

<210> SEQ ID NO 12
<211> LENGTH: 17
<212> TYPE: DNA
<213> ORGANISM: Artificial
<220> FEATURE:
<223> OTHER INFORMATION: Forward primer for EPO-CTP constructs

<400> SEQUENCE: 12
gccctgctgt cggaagc                                             17

<210> SEQ ID NO 13
<211> LENGTH: 32
<212> TYPE: DNA

-continued

```
<213> ORGANISM: Artificial
<220> FEATURE:
<223> OTHER INFORMATION: Reverse primer for EPO-CTP constructs

<400> SEQUENCE: 13
attgcggccg cggatccaga agacctttat tg                                32

<210> SEQ ID NO 14
<211> LENGTH: 32
<212> TYPE: DNA
<213> ORGANISM: Artificial
<220> FEATURE:
<223> OTHER INFORMATION: Reverse primer for EPO-CTP constructs

<400> SEQUENCE: 14
ctttgaggaa gaggagccca ggactgggag gc                                32

<210> SEQ ID NO 15
<211> LENGTH: 24
<212> TYPE: DNA
<213> ORGANISM: Artificial
<220> FEATURE:
<223> OTHER INFORMATION: Forward primer for EPO-CTP constructs

<400> SEQUENCE: 15
cctgggctcc tcttcctcaa aggc                                         24

<210> SEQ ID NO 16
<211> LENGTH: 193
<212> TYPE: PRT
<213> ORGANISM: Homo sapiens

<400> SEQUENCE: 16
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 17
<211> LENGTH: 34
<212> TYPE: PRT
<213> ORGANISM: Artificial
<220> FEATURE:
<223> OTHER INFORMATION: CTP amino acid sequence

<400> SEQUENCE: 17

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

Pro Gln

<210> SEQ ID NO 18
<211> LENGTH: 28
<212> TYPE: PRT
<213> ORGANISM: Artificial
<220> FEATURE:
<223> OTHER INFORMATION: CTP amino acid sequence

<400> SEQUENCE: 18

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 19
<211> LENGTH: 27
<212> TYPE: PRT
<213> ORGANISM: Homo sapiens

<400> SEQUENCE: 19

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 20
<211> LENGTH: 786
<212> TYPE: DNA
<213> ORGANISM: Homo sapiens

<400> SEQUENCE: 20
tctagaggtc atcatggggg tgcacgaatg tcctgcctgg ctgtggcttc tcctgtccct      60
tctgtcgctc cctctgggcc tcccagtcct gggctcctct tcctcaaagg cccctccccc    120
gagccttcca gtccatccc gactcccggg ccctcggac accccaatat taccacaagc    180
cccaccacgc tcatctgtg acagccgagt cctggagagg tacctcttgg aggccaagga    240
ggccgagaat atcacgacgg gctgtgctga acactgcagc ttgaatgaga atatcactgt    300
cccagacacc aaagttaatt tctatgcctg gaagaggatg gaggtcgggc agcaggccgt    360
agaagtctgg cagggcctgg ccctgctgtc ggaagctgtc ctgcggggcc aggccctgtt    420
ggtcaactct tcccagccgt gggagcccct gcagctgcat gtggataaag ccgtcagtgg    480
ccttcgcagc ctcaccactc tgcttcgggc tctgggagcc cagaaggaag ccatctcccc    540
tccagatgcg gcctcagctg ctccactccg aacaatcact gctgacactt tccgcaaact    600
cttccgagtc tactccaatt tcctccgggg aaagctgaag ctgtacacag ggaggcctg    660
caggacaggg gacagatcct cttcctcaaa ggcccctccc ccgagccttc caagtccatc    720

```
ccgactcccg gggccctcgg acaccccgat cctcccacaa taaaggtctt ctggatccgc    780
ggccgc                                                              786
```

<210> SEQ ID NO 21
<211> LENGTH: 873
<212> TYPE: DNA
<213> ORGANISM: Homo sapiens

<400> SEQUENCE: 21

```
tctagaggtc atcatggggg tgcacgaatg tcctgcctgg ctgtggcttc tcctgtccct    60
tctgtcgctc cctctgggcc tcccagtcct gggctcctct tcctcaaagg cccctccccc   120
gagccttcca agtccatccc gactcccggg gccctcggac accccaatat taccacaagc   180
cccaccacgc ctcatctgtg acagccgagt cctggagagg tacctcttgg aggccaagga   240
ggccgagaat atcacgacgg gctgtgctga acactgcagc ttgaatgaga atatcactgt   300
cccagacacc aaagttaatt tctatgcctg gaagaggatg gaggtcgggc agcaggccgt   360
agaagtctgg cagggcctgg ccctgctgtc ggaagctgtc ctgcggggcc aggccctgtt   420
ggtcaactct cccagccgt gggagcccct gcagctgcat gtggataaag ccgtcagtgg   480
ccttcgcagc ctcaccactc tgcttcgggc tctgggagcc cagaaggaag ccatctcccc   540
tccagatgcg gcctcagctg ctccactccg aacaatcact gctgacactt ccgcaaact   600 cttccgagtc tactccaatt tcctccgggg aaagctgaag ctgtacacag ggaggcctg   660 caggacaggg gacagatcct cttcctcaaa ggcccctccc ccgagccttc aagtccatc   720 ccgactcccg ggccctccg acacaccaat cctgccacag agcagctcct ctaaggcccc   780
tcctccatcc ctgccatccc cctcccggct gcctggcccc tctgacaccc ctatcctgcc   840
tcagtgatga aggtcttctg gatccgcggc cgc                                 873
```

<210> SEQ ID NO 22
<211> LENGTH: 221
<212> TYPE: PRT
<213> ORGANISM: Homo sapiens

<400> SEQUENCE: 22

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Ser Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160
```

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln
    210                 215                 220

<210> SEQ ID NO 23
<211> LENGTH: 217
<212> TYPE: PRT
<213> ORGANISM: Homo sapiens

<400> SEQUENCE: 23

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
    195                 200                 205

Arg Ser Val Glu Gly Ser Cys Gly Phe
    210                 215

<210> SEQ ID NO 24
<211> LENGTH: 166
<212> TYPE: PRT
<213> ORGANISM: Homo sapiens

<400> SEQUENCE: 24

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

```
Gln Phe Gln Lys Glu Asp Ala Ala Leu Thr Ile Tyr Glu Met Leu Gln
         50                  55                  60
Asn Ile Phe Ala Ile Phe Arg Gln Asp Ser Ser Thr Gly Trp Asn
 65                  70                  75                  80
Glu Thr Ile Val Glu Asn Leu Leu Ala Asn Val Tyr His Gln Ile Asn
                 85                  90                  95
His Leu Lys Thr Val Leu Glu Glu Lys Leu Glu Lys Glu Asp Phe Thr
            100                 105                 110
Arg Gly Lys Leu Met Ser Ser Leu His Leu Lys Arg Tyr Tyr Gly Arg
        115                 120                 125
Ile Leu His Tyr Leu Lys Ala Lys Glu Tyr Ser His Cys Ala Trp Thr
    130                 135                 140
Ile Val Arg Val Glu Ile Leu Arg Asn Phe Tyr Phe Ile Asn Arg Leu
145                 150                 155                 160
Thr Gly Tyr Leu Arg Asn
                165

<210> SEQ ID NO 25
<211> LENGTH: 30
<212> TYPE: PRT
<213> ORGANISM: Homo sapiens

<400> SEQUENCE: 25

His Ala Glu Gly Thr Phe Thr Ser Asp Val Ser Ser Tyr Leu Glu Gly
 1               5                  10                  15
Gln Ala Ala Lys Glu Phe Ile Ala Trp Leu Val Lys Gly Arg
            20                  25                  30

<210> SEQ ID NO 26
<211> LENGTH: 21
<212> TYPE: PRT
<213> ORGANISM: Homo sapiens

<400> SEQUENCE: 26

Met Thr Asn Lys Cys Leu Leu Gln Ile Ala Leu Leu Leu Cys Phe Ser
 1               5                  10                  15
Thr Thr Ala Leu Ser
            20

<210> SEQ ID NO 27
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 27
ctctagagga catggccac                                                    19

<210> SEQ ID NO 28
<211> LENGTH: 24
<212> TYPE: DNA
<213> ORGANISM: Artificial
<220> FEATURE:
<223> OTHER INFORMATION: Reverse primer for HGH-CTP constructs

<400> SEQUENCE: 28
acagggaggt ctggggttc tgca                                               24

<210> SEQ ID NO 29
```

```
<211> LENGTH: 26
<212> TYPE: DNA
<213> ORGANISM: Artificial
<220> FEATURE:
<223> OTHER INFORMATION: Forward primer for HGH-CTP constructs

<400> SEQUENCE: 29
tgcagaaccc ccagacctcc ctgtgc                                    26

<210> SEQ ID NO 30
<211> LENGTH: 22
<212> TYPE: DNA
<213> ORGANISM: Artificial
<220> FEATURE:
<223> OTHER INFORMATION: Reverse primer for HGH-CTP constructs

<400> SEQUENCE: 30
ccaaactcat caatgtatct ta                                        22

<210> SEQ ID NO 31
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 31
ctctagagga catggccac                                            19

<210> SEQ ID NO 32
<211> LENGTH: 25
<212> TYPE: DNA
<213> ORGANISM: Artificial
<220> FEATURE:
<223> OTHER INFORMATION: Reverse primer for HGH-CTP constructs

<400> SEQUENCE: 32
cgaactcctg gtaggtgtca aaggc                                     25

<210> SEQ ID NO 33
<211> LENGTH: 25
<212> TYPE: DNA
<213> ORGANISM: Artificial
<220> FEATURE:
<223> OTHER INFORMATION: Forward primer for HGH-CTP constructs

<400> SEQUENCE: 33
gcctttgaca cctaccagga gttcg                                     25

<210> SEQ ID NO 34
<211> LENGTH: 33
<212> TYPE: DNA
<213> ORGANISM: Artificial
<220> FEATURE:
<223> OTHER INFORMATION: NotI Reverse primer for HGH-CTP constructs

<400> SEQUENCE: 34
acgcggccgc atccagacct tcatcactga ggc                            33

<210> SEQ ID NO 35
<211> LENGTH: 34
<212> TYPE: DNA
<213> ORGANISM: Artificial
<220> FEATURE:
<223> OTHER INFORMATION: Reverse primer for HGH-CTP constructs

<400> SEQUENCE: 35
```
gcggccgcgg actcatcaga agccgcagct gccc        34

<210> SEQ ID NO 36
<211> LENGTH: 217
<212> TYPE: PRT
<213> ORGANISM: Homo sapiens

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 37
<211> LENGTH: 245
<212> TYPE: PRT
<213> ORGANISM: Homo sapiens

<400> SEQUENCE: 37

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

```
Ser Asn Leu Glu Leu Leu Arg Ile Ser Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
210                 215                 220

Pro Pro Ser Leu Pro Ser Pro Ser Arg Leu Pro Gly Pro Ser Asp Thr
225                 230                 235                 240

Pro Ile Leu Pro Gln
            245

<210> SEQ ID NO 38
<211> LENGTH: 273
<212> TYPE: PRT
<213> ORGANISM: Homo sapiens

<400> SEQUENCE: 38

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
210                 215                 220
```

Pro Pro Ser Leu Pro Ser Pro Ser Arg Leu Pro Gly Pro Ser Asp Thr
225                 230                 235                 240

Pro Ile Leu Pro Gln Ser Ser Ser Lys Ala Pro Pro Pro Ser Leu
        245                 250                 255

Pro Ser Pro Ser Arg Leu Pro Gly Pro Ser Asp Thr Pro Ile Leu Pro
        260                 265                 270

Gln

<210> SEQ ID NO 39
<211> LENGTH: 301
<212> TYPE: PRT
<213> ORGANISM: Homo sapiens

<400> SEQUENCE: 39

Met Ala Thr Gly Ser Arg Thr Ser Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
                35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255

Pro Ser Pro Ser Arg Leu Pro Gly Pro Ser Asp Thr Pro Ile Leu Pro
        260                 265                 270

Gln Ser Ser Ser Lys Ala Pro Pro Pro Ser Leu Pro Ser Pro Ser
        275                 280                 285

Arg Leu Pro Gly Pro Ser Asp Thr Pro Ile Leu Pro Gln
        290                 295                 300

<210> SEQ ID NO 40

<211> LENGTH: 285
<212> TYPE: PRT
<213> ORGANISM: Homo sapiens

<400> SEQUENCE: 40

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Phe Pro Thr Ile Pro Leu Ser Arg Leu Phe
            35                  40                  45

Asp Asn Ala Met Leu Arg Ala His Arg Leu His Gln Leu Ala Phe Asp
        50                  55                  60

Thr Tyr Gln Glu Phe Glu Glu Ala Tyr Ile Pro Lys Glu Gln Lys Tyr
65                  70                  75                  80

Ser Phe Leu Gln Asn Pro Gln Thr Ser Leu Cys Phe Ser Glu Ser Ile
                85                  90                  95

Pro Thr Pro Ser Asn Arg Glu Glu Thr Gln Gln Lys Ser Asn Leu Glu
            100                 105                 110

Leu Leu Arg Ile Ser Leu Leu Leu Ile Gln Ser Trp Leu Glu Pro Val
            115                 120                 125

Gln Phe Leu Arg Ser Val Phe Ala Asn Ser Leu Val Tyr Gly Ala Ser
        130                 135                 140

Asp Ser Asn Val Tyr Asp Leu Leu Lys Asp Leu Glu Glu Gly Ile Gln
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
            180                 185                 190

Ala Leu Leu Lys Asn Tyr Gly Leu Leu Tyr Cys Phe Arg Lys Asp Met
        195                 200                 205

Asp Lys Val Glu Thr Phe Leu Arg Ile Val Gln Cys Arg Ser Val Glu
    210                 215                 220

Gly Ser Cys Gly Phe Ser Ser Ser Lys Ala Pro Pro Pro Ser Leu
225                 230                 235                 240

Pro Ser Pro Ser Arg Leu Pro Gly Pro Ser Asp Thr Pro Ile Leu Pro
            245                 250                 255

Gln Ser Ser Ser Lys Ala Pro Pro Ser Leu Pro Ser Pro Ser
        260                 265                 270

Arg Leu Pro Gly Pro Ser Asp Thr Pro Ile Leu Pro Gln
        275                 280                 285
```

<210> SEQ ID NO 41
<211> LENGTH: 273
<212> TYPE: PRT
<213> ORGANISM: Homo sapiens

<400> SEQUENCE: 41

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
        50                  55                  60
```

```
Asp Asn Ala Met Leu Arg Ala His Arg Leu His Gln Leu Ala Phe Asp
 65                  70                  75                  80

Thr Tyr Gln Glu Phe Glu Glu Ala Tyr Ile Pro Lys Glu Gln Lys Tyr
                 85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
                115                 120                 125

Leu Leu Arg Ile Ser Leu Leu Leu Ile Gln Ser Trp Leu Glu Pro Val
                130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
                180                 185                 190

Phe Lys Gln Thr Tyr Ser Lys Phe Asp Thr Asn Ser His Asn Asp Asp
                195                 200                 205

Ala Leu Leu Lys Asn Tyr Gly Leu Leu Tyr Cys Phe Arg Lys Asp Met
210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Ser Leu
                245                 250                 255

Pro Ser Pro Ser Arg Leu Pro Gly Pro Ser Asp Thr Pro Ile Leu Pro
                260                 265                 270

Gln

<210> SEQ ID NO 42
<211> LENGTH: 245
<212> TYPE: PRT
<213> ORGANISM: Homo sapiens

<400> SEQUENCE: 42

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Ser Ser Ser Lys Ala
                 20                  25                  30

Pro Pro Pro Ser Leu Pro Ser Pro Ser Arg Leu Pro Gly Pro Ser Asp
                 35                  40                  45

Thr Pro Ile Leu Pro Gln Phe Pro Thr Ile Pro Leu Ser Arg Leu Phe
 50                  55                  60

Asp Asn Ala Met Leu Arg Ala His Arg Leu His Gln Leu Ala Phe Asp
 65                  70                  75                  80

Thr Tyr Gln Glu Phe Glu Glu Ala Tyr Ile Pro Lys Glu Gln Lys Tyr
                 85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
                115                 120                 125

Leu Leu Arg Ile Ser Leu Leu Leu Ile Gln Ser Trp Leu Glu Pro Val
                130                 135                 140

Gln Phe Leu Arg Ser Val Phe Ala Asn Ser Leu Val Tyr Gly Ala Ser
145                 150                 155                 160
```

```
Asp Ser Asn Val Tyr Asp Leu Leu Lys Asp Leu Glu Glu Gly Ile Gln
            165                 170                 175

Thr Leu Met Gly Arg Leu Glu Asp Gly Ser Pro Arg Thr Gly Gln Ile
        180                 185                 190

Phe Lys Gln Thr Tyr Ser Lys Phe Asp Thr Asn Ser His Asn Asp Asp
    195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe
            245

<210> SEQ ID NO 43
<211> LENGTH: 12
<212> TYPE: PRT
<213> ORGANISM: Artificial
<220> FEATURE:
<223> OTHER INFORMATION: CTP amino acid sequence

<400> SEQUENCE: 43

Ser Ser Ser Ser Lys Ala Pro Pro Pro Ser Leu Pro
1               5                   10

<210> SEQ ID NO 44
<211> LENGTH: 853
<212> TYPE: DNA
<213> ORGANISM: Homo sapiens

<400> SEQUENCE: 44
tctagaggac atggccaccg gcagcaggac cagcctgctg ctggccttcg gcctgctgtg      60
cctgccatgg ctgcaggagg gcagcgccag ctcttcttct aaggctccac ccccatctct     120
gcccagcccc agcagactgc cgggcccag cgacacaccc attctgcccc agttccccac     180
catccccctg agcaggctgt cgacaacgc catgctgagg gctcacaggc tgcaccagct     240
ggcctttgac acctaccagg agttcgagga agcctacatc cccaaggagc agaagtacag     300
cttcctgcag aacccccaga cctccctgtg cttcagcgag agcatcccca cccccagcaa     360
cagagaggag acccagcaga gagcaacct ggagctgctg aggatctccc tgctgctgat     420
ccagagctgg ctggagcccg tgcagttcct gagaagcgtg ttcgccaaca gcctggtgta     480
cggcgccagc gacagcaacg tgtacgacct gctgaaggac ctggaggagg catccagac     540 cctgatgggc cggctggagg acggcagccc caggaccggc cagatcttca gcagacctac     600
cagcaagttc gacaccaaca gccacaacga cgacgccctg ctgaagaact acgggctgct     660
gtactgcttc agaaaggaca tggacaaggt ggagaccttc ctgaggatcg tgcagtgcag     720
aagcgtggag ggcagctgcg gcttcagctc cagcagcaag gcccctcccc cgagcctgcc     780
ctccccaagc aggctgcctg ggccctccga cacaccaatc ctgcctcagt gatgaaggtc     840
tggatgcggc cgc                                                        853

<210> SEQ ID NO 45
<211> LENGTH: 937
<212> TYPE: DNA
<213> ORGANISM: Homo sapiens

<400> SEQUENCE: 45
tctagaggac atggccaccg gcagcaggac cagcctgctg ctggccttcg gcctgctgtg      60
```

```
cctgccatgg ctgcaggagg gcagcgccag ctcttcttct aaggctccac ccccatctct    120
gcccagcccc agcagactgc cgggcccag cgacacaccc attctgcccc agttccccac     180 catcccctg agcaggctgt tcgacaacgc catgctgagg gctcacaggc tgcaccagct     240
ggcctttgac acctaccagg agttcgagga agcctacatc cccaaggagc agaagtacag    300
cttcctgcag aaccccagga cctccctgtg cttcagcgag agcatcccca ccccagcaa     360 cagagaggag acccagcaga agagcaacct ggagctgctg aggatctccc tgctgctgat    420
ccagagctgg ctggagcccg tgcagttcct gagaagcgtg ttcgccaaca gcctggtgta    480
cggcgccagc gacagcaacg tgtacgacct gctgaaggac ctggaggagg catccagac    540 cctgatgggc cggctggagg acggcagccc caggaccggc cagatcttca gcagaccta    600 cagcaagttc gacaccaaca gccacaacga cgacgccctg ctgaagaact acgggctgct    660
gtactgcttc agaaaggaca tggacaaggt ggagaccttc ctgaggatcg tgcagtgcag    720
aagcgtggag ggcagctgcg gcttcagctc cagcagcaag gcccctcccc cgagcctgcc    780
ctccccaagc aggctgcctg ggcctccga cacaccaatc ctgccacaga gcagctcctc    840
taaggcccct cctccatccc tgccatcccc ctcccggctg cctggcccct ctgacacccc    900
tatcctgcct cagtgatgaa ggtctggatg cggccgc                              937

<210> SEQ ID NO 46
<211> LENGTH: 889
<212> TYPE: DNA
<213> ORGANISM: Homo sapiens

<400> SEQUENCE: 46
tctagaggac atggccaccg gcagcaggac cagcctgctg ctggccttcg gcctgctgtg     60
cctgccatgg ctgcaggagg gcagcgccag ctcttcttct aaggctccac ccccgagcct    120
gcccttcccc accatccccc tgagcaggct gttcgacaac gccatgctga gggctcacag    180
gctgcaccag ctggcctttg acacctacca ggagttcgag gaagcctaca tccccaagga    240
gcagaagtac agcttcctgc agaaccccca gacctccctg tgcttcagcg agagcatccc    300 caccccagc aacagagagg agacccagca agagcaac ctggagctgc tgaggatctc    360
cctgctgctg atccagagct ggctggagcc cgtgcagttc ctgagaagcg tgttcgccaa    420
cagcctggtg tacggcgcca gcgacagcaa cgtgtacgac ctgctgaagg acctggagga    480
gggcatccag accctgatgg gccggctgga ggacggcagc cccaggaccg gccagatctt    540
caagcagacc tacagcaagt cgacaccaa cagccacaac gacgacgccc tgctgaagaa    600
ctacgggctg ctgtactgct tcagaaagga catggacaag gtggagacct tcctgaggat    660
cgtgcagtgc agaagcgtgg agggcagctg cggcttcagc tccagcagca aggcccctcc    720
cccgagcctg ccctccccaa gcaggctgcc tgggcctcc gacacaccaa tcctgccaca    780
gagcagctcc tctaaggccc ctcctccatc cctgccatcc cctcccggc tgcctggccc    840 ctctgacacc cctatcctgc ctcagtgatg aaggtctgga tgcggccgc                 889

<210> SEQ ID NO 47
<211> LENGTH: 217
<212> TYPE: PRT
<213> ORGANISM: Homo sapiens

<400> SEQUENCE: 47

Met Ala Thr Gly Ser Arg Thr Ser Leu Leu Leu Ala Phe Gly Leu Leu
1               5                   10                  15
```

```
Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
             85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 48
<211> LENGTH: 33
<212> TYPE: PRT
<213> ORGANISM: Homo sapiens

<400> SEQUENCE: 48

Asp Pro Arg Phe Gln Asp Ser Ser Ser Ser Lys Ala Pro Pro Pro Ser
 1               5                  10                  15

Leu Pro Ser Pro Ser Arg Leu Pro Gly Pro Ser Asp Thr Pro Ile Leu
             20                  25                  30

Gln

<210> SEQ ID NO 49
<211> LENGTH: 26
<212> TYPE: PRT
<213> ORGANISM: Homo sapiens

<400> SEQUENCE: 49

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
             20                  25
```

```
<210> SEQ ID NO 50
<211> LENGTH: 17
<212> TYPE: DNA
<213> ORGANISM: Artificial Sequence
<220> FEATURE:
<223> OTHER INFORMATION: Reverse primer for EPO-CTP constructs

<400> SEQUENCE: 50
gcttccgaca gcagggc                                                    17
```

LONG-ACTING POLYPEPTIDES AND METHODS OF PRODUCING AND ADMINISTERING SAME

CROSS REFERENCE TO RELATED APPLICATIONS

This application is a division of U.S. patent application Ser. No. 15/200,813 filed on Jul. 1, 2016 and now U.S. Pat. No. 11,197,915, which is a continuation of U.S. patent application Ser. No. 14/555,308 filed on Nov. 26, 2014 (abandoned), which is a continuation of International Application No. PCT/IL2014/050910 filed on Oct. 21, 2014 (published as WO 2015/059695), which is a continuation in-part of U.S. patent application Ser. No. 14/309,496 filed on Jun. 19, 2014 (abandoned), and a continuation in-part of U.S. patent application Ser. No. 14/059,134 filed on Oct. 21, 2013 (abandoned), each of which are incorporated by reference herein in their entireties.

INCORPORATION OF SEQUENCE LISTING

The present application is being filed along with a sequence listing in electronic format. The sequence listing is provided as a file entitled Sequence Listing_P35132US03.txt, created on Dec. 8, 2021, which is 52 KB in size. The information in the electronic format of the sequence listing is incorporated herein by reference in its entirety.

FIELD OF INVENTION

CTP-modified human growth hormone polypeptides and pharmaceutical formulations and pharmaceutical compositions comprising the same and methods of producing, and using the same are disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administered by infusion, frequent injection of peptide drugs causes considerable discomfort to a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

Thus, there is a need for technologies that will prolong the half-lives of therapeutic polypeptides while maintaining a high pharmacological efficacy thereof. Such desired peptide drugs should also meet the requirements of enhanced serum stability, high activity and a low probability of inducing an undesired immune response when injected into a subject. The present invention addresses this need by providing CTP-modified peptides having prolonged half-lives while maintaining a high pharmacological efficacy, and while having enhanced serum stability, high activity and low probability of inducing undesired immune responses in a subject.

SUMMARY OF THE INVENTION

In one embodiment, the invention relates to a pharmaceutical formulation comprising a buffer, a tonicity agent, and a CTP-modified polypeptide consisting of a growth hormone and one chorionic gonadotropin carboxy terminal peptide (CTP) attached to the amino terminus of said growth hormone, and two chorionic gonadotropin CTPs attached to the carboxy terminus of said growth hormone. In one embodiment, the growth hormone is a human growth hormone. In one embodiment, the tonicity agent is sodium chloride. In one embodiment, the tonicity agent is 147 mM sodium chloride. In one embodiment, the formulation is a liquid formulation. In one embodiment, the formulation is at a pH of about 6.2-6.4.

In one embodiment, the invention relates to a formulation for a once a week administration to a subject having a growth hormone deficiency. In another embodiment, the subject is an adult. In another embodiment, the subject is a growth hormone deficient adult. In another embodiment, the subject is a child. In another embodiment, the subject is a growth hormone deficient child. In another embodiment, the invention relates to a process for making a pharmaceutical formulation for a once a week administration to a subject having a growth hormone deficiency, the process comprising the steps of:
  a. modifying a growth hormone by attaching one chorionic gonadotropin carboxy terminal peptide (CTP) attached to the amino terminus of said growth hormone, and two chorionic gonadotropin CTPs attached to the carboxy terminus of said growth hormone;
  b. mixing the modified growth hormone in step a. with said buffer, and said tonicity agent at a pH of 6.2-6.4; and,
  c. pre-filling a syringe with said formulation.

In one embodiment, the invention relates to a pharmaceutical composition for a once a week administration to a subject having a growth hormone deficiency comprising a CTP-modified polypeptide, said CTP-modified polypeptide consisting of a growth hormone and one chorionic gonadotropin carboxy terminal peptide (CTP) attached to the amino terminus of said growth hormone, and two chorionic gonadotropin CTPs attached to the carboxy terminus of said growth hormone. In one embodiment, the growth hormone is a human growth hormone. In another embodiment, the subject is an adult. In another embodiment, the subject is a growth hormone deficient adult. In another embodiment, the subject is a child. In another embodiment, the subject is a growth hormone deficient child.

In one embodiment, the invention relates to a once weekly dosage form comprising a pharmaceutical formulation of this invention or a pharmaceutical composition of this invention.

In one embodiment, the invention relates to a process for filling a syringe with a formulation provided herein comprising the steps of:
  a. formulating a once a week dosage form of said CTP-modified hGH having a pre-determined amount of CTP-modified hGH; and,
  b. filling the syringe with said formulation.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 24 is a table showing non-GMP and GMP batches produced in 10 mM Citrate, 147 mM NaCl at pH 6.

FIG. 29 is a table showing the transfer of MOD-4023 Manufacturing from Xcellerex (XC) to Rentschler (RB).

FIG. 35A shows IEF Profile of MOD-4023 Batches. There's a similar band pattern in a pI-value range from 3.5 to 4.2 In one XCLX batch there are less faint isoforms in the high pI boundary. In RB batch there are more faint isoforms in the low pI boundary.

FIG. 35B shows Stability results (IEF) from RB and XCLX (3 months at 25° C.). More diffused bands in XCLX sample.

FIG. 36A-D shows Effect of high temperatures on % of peaks (clone 2) (FIG. 36A—mail peak; FIG. 36D). The formation of both peaks (3 and 5) is temperature dependent and accelerates at high temperature. (FIG. 36B and FIG. 36C)

FIG. 37A-D shows Effect of pH on % of Peaks (clone 2) (FIG. 37A—main peak; FIG. 37D). Peak 3: No change in the % of the peak after incubation for up to 5 days at pH=4 and up to 2 h at pH=12 (FIG. 37B). Peak 5: No change in the % of the peak after incubation for up to 6 h at pH=4. However, following 6 h a sharp increase in the peak % was observed. At pH 12 incubation for up to 2 h—the peak disappears (FIG. 37C).

FIG. 39 shows pH effect on RP-HPLC related forms. Tested samples: RB—40 mg/ml, pH=5.9; RB—10 mg/ml, pH=6.2; XCLX—40 mg/ml, pH=6.2.

DETAILED DESCRIPTION OF THE INVENTION

Figure 1:
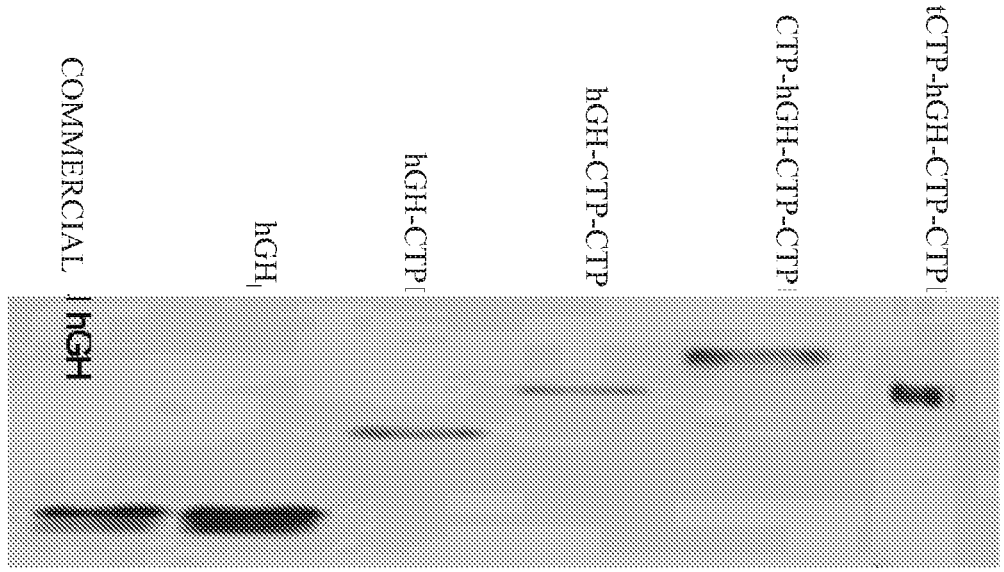
FIG. 1 is a Western blot illustrating the molecular weight & identity of MOD-4020 (SEQ ID NO: 36), MOD-4021 (SEQ ID NO: 37), MOD-4022 (SEQ ID NO: 38), MOD-4023 (SEQ ID NO: 39) and MOD-4024 (SEQ ID NO: 40). A PAGE SDS gel was blotted and stained using monoclonal anti-hGH antibodies. The photograph indicates that like commercial and wild type hGH, MOD-7020-4 variants are recognized by anti-hGH antibodies.

This application claims the benefit of United States Patent Application Publication Number US-2014-0113860-A1, filed Oct. 21, 2013 and claims the benefit of U.S. patent application Ser. No. 14/309,496, filed Jun. 19, 2014. These applications are hereby incorporated by reference in their entirety herein.

In one embodiment, the invention relates to a pharmaceutical formulation comprising a buffer, a tonicity agent, and a CTP-modified polypeptide consisting of a growth hormone and one chorionic gonadotropin carboxy terminal peptide (CTP) attached to the amino terminus of said growth hormone, and two chorionic gonadotropin CTPs attached to the carboxy terminus of said growth hormone.

In one embodiment, the invention relates to a formulation for a once a week administration to a subject having a growth hormone deficiency. In another embodiment, the subject is an adult. In another embodiment, the subject is a growth hormone deficient adult. In another embodiment, the subject is a child. In another embodiment, the subject is a growth hormone deficient child. In another embodiment, the invention relates to a process for making a pharmaceutical formulation for a once a week administration to a subject having a growth hormone deficiency, the process comprising the steps of:

a. modifying a growth hormone by attaching one chorionic gonadotropin carboxy terminal peptide (CTP) attached to the amino terminus of said growth hormone, and two chorionic gonadotropin CTPs attached to the carboxy terminus of said growth hormone;

b. mixing the modified growth hormone in step a. with said buffer, and said tonicity agent at a pH of 6.2-6.4; and, c. pre-filling a syringe with said formulation.

In one embodiment, the invention relates to a process for filling a syringe with a formulation provided herein comprising the steps of:

a. formulating a once a week dosage form of said CTP-modified human growth hormone (hGH) having a pre-determined amount of CTP-modified hGH; and, b. filling the syringe with said formulation.

In one embodiment, the present invention describes long-acting polypeptides and methods of producing and using same. In another embodiment, long-acting polypeptides comprise carboxy terminal peptide (CTP) of human Chorionic Gonadotropin (hCG). In another embodiment, CTP acts as a protectant against degradation of proteins or peptides derived therefrom. In another embodiment, CTP extends circulatory half-lives of proteins or peptides derived therefrom. In some embodiments, CTP enhances the potency of proteins or peptides derived therefrom.

In another embodiment, "CTP peptide," "carboxy terminal peptide," "CTP sequence," and "chorionic gonadotropin C-terminal peptide" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, "peptide of interest" and "polypeptide sequence of interest" are used interchangeably herein. In another embodiment, the peptide of interest is a full-length protein. In another embodiment, the peptide of interest is a protein fragment. Each possibility represents a separate embodiment of the present invention.

In another embodiment, the invention provides a pharmaceutical formulation comprising a polypeptide consisting of a growth hormone, a single chorionic gonadotropin carboxy terminal peptide attached to the amino terminus of the growth hormone, and two chorionic gonadotropin carboxy terminal peptides attached to the carboxy terminus of the growth hormone. In another embodiment, the invention provides a pharmaceutical formulation comprising polypeptide consisting of a growth hormone, a single chorionic gonadotropin carboxy terminal peptide attached to the amino terminus of the growth hormone, two chorionic gonadotropin carboxy terminal peptides attached to the carboxy terminus of the growth hormone, and a signal peptide attached to the amino terminus of one chorionic gonadotropin carboxy terminal peptide. In another embodiment, the pharmaceutical formulation further comprises a buffer and a tonicity agent. In another embodiment, the buffer is 10 mM citrate and the tonicity agent is 147 mM NaCl. In one embodiment, the formulation is at about a pH of 6.0. In another embodiment, the formulation is at about a pH of 6.2. In another embodiment, the formulation is at about a pH of 6.4. In another embodiment, the formulation is at about a pH range of 6.0-6.4. In one embodiment, the buffer is 10 mM citrate, the tonicity agent is 147 mM NaCl, and the pH is 6.0. In another embodiment, the formulation is a liquid formulation.

In another embodiment, provided herein is a once weekly dosage form comprising the pharmaceutical formulation provided herein.

In another embodiment, the invention provides a pharmaceutical composition comprising a polypeptide consisting of a growth hormone, a single chorionic gonadotropin carboxy terminal peptide attached to the amino terminus of the growth hormone, and two chorionic gonadotropin carboxy terminal peptides attached to the carboxy terminus of the growth hormone. In another embodiment, the invention provides a pharmaceutical composition comprising polypeptide consisting of a growth hormone, a single chorionic gonadotropin carboxy terminal peptide attached to the amino terminus of the growth hormone, two chorionic gonadotropin carboxy terminal peptides attached to the carboxy terminus of the growth hormone, and a signal peptide attached to the amino terminus of one chorionic gonadotropin carboxy terminal peptide.

In another embodiment, a growth hormone comprising CTPs as described herein has enhanced in vivo biological activity compared the same growth hormone without CTPs. In another embodiment, a growth hormone comprising at least one CTP attached to its amino terminus and at least two CTPs attached to its carboxy terminus has enhanced in vivo biological activity compared the same growth hormone without CTPs. In another embodiment, a growth hormone comprising one CTP attached to its amino terminus and two CTPs attached to its carboxy terminus has enhanced in vivo biological activity compared the same growth hormone without CTPs.

In another embodiment, a polypeptide comprising at least two carboxy-terminal peptide (CTP) sequences of chorionic gonadotropin attached to a polypeptide sequence of interest, wherein a first CTP sequence of the at least two CTP sequences is attached to an amino terminus of the polypeptide sequence of interest and a second CTP sequence of the at least two CTP sequences is attached to the carboxy terminus of the polypeptide sequence of interest is provided. In another embodiment, the carboxy-terminal peptide (CTP) sequence is of human chorionic gonadotropin.

In another embodiment, a subject is a human subject. In one embodiment, the human subject is growth hormone deficient. In one embodiment, the subject is growth hormone deficient. In another embodiment, a subject is a pet. In another embodiment, a subject is a mammal. In another embodiment, a subject is a farm animal. In another embodiment, a subject is a dog. In another embodiment, a subject is a cat. In another embodiment, a subject is a monkey. In another embodiment, a subject is a horse. In another embodiment, a subject is a cow. In another embodiment, a subject is a mouse. In another embodiment, a subject is a rat. In one embodiment, the subject is male. In another embodiment, the subject is female. In another embodiment, the subject is a growth hormone deficient (GHD) adult. In another embodiment, the subject is a pre-pubertal growth hormone deficient (GHD) child. As demonstrated herein, various doses of MOD-4023 (CTP-hGH-CTP-CTP) provided a good catch-up growth response in pre-pubescent children (see Example 10).

The phrase "polypeptide sequence of interest" refers, in another embodiment, to any polypeptide sequence, such as one comprising a biological activity. In another embodiment, the peptide is glycosylated. In another embodiment, the peptide is non-glycosylated. Examples of polypeptides which benefit from an extension in their circulatory half-life include, but are not limited to erythropoietin (EPO), interferons, human growth hormone (hGH) and glucagon-like peptide-1(GLP-1). In one embodiment, the polypeptide is a growth hormone (GH). In another embodiment, the polypeptide is a human growth hormone (hGH).

In one embodiment, the configuration of CTP-growth hormone-CTP-CTP as described herein comprises a growth hormone or an active fragment thereof connected via a linker to at least one CTP unit. In one embodiment, the linker is a peptide bond. In another embodiment, the configuration of CTP-growth hormone-CTP-CTP as described herein comprises a growth hormone or an active fragment thereof connected via a peptide bond to at least one CTP unit. In another embodiment, a CTP-growth hormone-CTP-CTP as described herein comprises a growth hormone or an active fragment thereof connected via a peptide bond to at least one CTP unit which is connected to an additional CTP unit via a peptide bond. In another embodiment, a polypeptide as described herein comprising a growth hormone fragments thereof and CTP units and/or fragments thereof are interconnected via a peptide bond. In another embodiment, one nucleic acid molecule encodes a polypeptide as described herein comprising a growth hormone and/or fragments thereof and CTP units and/or fragments thereof.

In another embodiment, the carboxy-terminal peptide (CTP) is attached to the polypeptide sequence of interest via a linker. In another embodiment, at least one CTP is optionally attached to said polypeptide sequence of interest via a linker. In another embodiment, the linker which connects the CTP sequence to the polypeptide sequence of interest is a covalent bond. In another embodiment, the linker which connects the CTP sequence to the polypeptide sequence of interest is a peptide bond. In another embodiment, the linker which connects the CTP sequence to the polypeptide sequence of interest is a substituted peptide bond. In another embodiment, the carboxy-terminal peptide (CTP) sequence comprises an amino acid sequence selected from the sequences set forth in SEQ ID NO: 48.

In another embodiment, SEQ ID NO: 48 comprises the following amino acid (AA) sequence:

```
                                      (SEQ ID NO: 48)
         DPRFQDSSSSKAPPPSLPSPSRLPGPSDTPILQ.
```

In another embodiment, the carboxy terminal peptide (CTP) of human Chorionic Gonadotropin (hCG) is fused to a protein. In another embodiment, the carboxy terminal peptide (CTP) of human Chorionic Gonadotropin (hCG) is fused to a peptide of said protein. In one embodiment, the protein or peptide thereof is a growth hormone. In one embodiment, the protein or peptide thereof is a human growth hormone. In another embodiment, the carboxy terminal peptide (CTP) of human hCG is fused to a glycoprotein. In another embodiment, the carboxy terminal peptide (CTP) of hCG is fused to a glycoprotein hormone. In another embodiment, the CTP of hCG is fused to a peptide derived from a glycoprotein hormone. In some embodiments, glycoprotein hormones comprise EPO, FSH, or TSH and peptides derived therefrom.

In some embodiments, a CTP sequence at both the amino terminal end of a polypeptide and at the carboxy terminal end of the polypeptide provide enhanced protection against degradation of a protein. In some embodiments, CTP sequences at both the amino terminal end of a polypeptide and at the carboxy terminal end of the polypeptide provide an extended half-life to the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced protection against degradation of a protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced activity of the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced protection against degradation of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced activity the attached protein.

In some embodiments, a CTP sequences at both the amino terminal end of a growth hormone and at the carboxy terminal end of the growth hormone provide enhanced protection against degradation of a growth hormone. In another embodiment, at least one CTP sequence at the amino terminal end of a growth hormone and two CTP units in the carboxy terminal end of a growth hormone provide enhanced protection against clearance. In another embodiment, at least one CTP sequence at the amino terminal end of a growth hormone and two CTP units in the carboxy terminal end of a growth hormone provide prolonged clearance time. In another embodiment, at least one CTP sequence at the amino terminal end of a growth hormone and two CTP units in the carboxy terminal end of a growth hormone enhance $C_{max}$ of a growth hormone. In another embodiment, at least one CTP sequence at the amino terminal end of a growth hormone and two CTP units in the carboxy terminal end of a growth hormone enhance $T_{max}$ of a growth hormone. In another embodiment, at least one CTP sequence at the amino terminal end of a growth hormone and two CTP units in the carboxy terminal end of a growth hormone enhanced T1/2.

In some embodiments, CTP sequences at both the amino terminal end of a growth hormone and at the carboxy terminal end of the growth hormone extend the half-life of the modified growth hormone. In another embodiment, at least a single CTP sequence at the amino terminal end of a growth hormone and at least two CTP sequences at the carboxy terminal end of the growth hormone provide an extended half-life to the modified growth hormone. In another embodiment, a single CTP sequence at the amino terminal end of a growth hormone and two CTP sequences at the carboxy terminal end of the growth hormone provide extended half-life to the attached growth hormone. In another embodiment, a single CTP sequence at the amino terminal end of a growth hormone and two CTP sequences in tandem at the carboxy terminal end of the growth hormone provide extended half-life to the modified growth hormone.

In some embodiments, a CTP sequence at the amino terminal end of a polypeptide, a CTP sequence at the carboxy terminal end of the growth hormone, and at least one additional CTP sequence attached in tandem to the CTP sequence at the carboxy terminus provide enhanced protection against degradation to a growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus extend the half-life of the growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus enhance the biological activity of the growth hormone.

In one embodiment, the sequence of at least one CTP consists of an amino acid sequence selected from the group consisting of: SEQ ID NO: 17 and SEQ ID NO: 18. In another embodiment, the carboxy terminal peptide (CTP) peptide of the present invention comprises the amino acid sequence from amino acid 112 to position 145 of human chorionic gonadotropin, as set forth in SEQ ID NO: 17. In another embodiment, the CTP sequence of the present invention comprises the amino acid sequence from amino acid 118 to position 145 of human chorionic gonadotropin, as set forth in SEQ ID NO: 18. In another embodiment, the CTP sequence also commences from any position between positions 112-118 and terminates at position 145 of human chorionic gonadotropin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotropin CTP which differs from the native CTP by 1-5 conservative amino acid substitutions as described in U.S. Pat. No. 5,712,122. In another embodiment, the CTP peptide is a variant of chorionic gonadotropin CTP which differs from the native CTP by 1 conservative amino acid substitution. In another embodiment, the CTP peptide is a variant of chorionic gonadotropin CTP which differs from the native CTP by 2 conservative amino acid substitutions. In another embodiment, the CTP peptide is a variant of chorionic gonadotropin CTP which differs from the native CTP by 3 conservative amino acid substitutions. In another embodiment, the CTP peptide is a variant of chorionic gonadotropin CTP which differs from the native CTP by 4 conservative amino acid substitutions. In another embodiment, the CTP peptide is a variant of chorionic gonadotropin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native CTP DNA sequence or a peptide thereof. In another embodiment, the CTP peptide DNA sequence of the present invention is at least 80% homologous to the native CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, at least one of the chorionic gonadotropin CTP amino acid sequences is truncated. In another embodiment, both of the chorionic gonadotropin CTP amino acid sequences are truncated. In another embodiment, 2 of the chorionic gonadotropin CTP amino acid sequences are truncated. In another embodiment, 2 or more of the chorionic gonadotropin CTP amino acid sequences are truncated. In another embodiment, all of the chorionic gonadotropin CTP amino acid sequences are truncated. In one embodiment, the truncated CTP comprises the first 10 amino acids of SEQ ID NO: 43. In one embodiment, the truncated CTP comprises the first 11 amino acids of SEQ ID NO: 43. In one embodiment, the truncated CTP comprises the first 12 amino acids of SEQ ID NO: 43. In one embodiment, the truncated CTP comprises the first 13 amino acids of SEQ ID NO: 43. In one embodiment, the truncated CTP comprises the first 14 amino acids of SEQ ID NO: 43. In one embodiment, the truncated CTP comprises the first 15 amino acids of SEQ ID NO: 43. In one embodiment, the truncated CTP comprises the first 16 amino acids of SEQ ID NO: 43. In one embodiment, the truncated CTP comprises the last 14 amino acids of SEQ ID NO: 43.

In one embodiment, at least one of the chorionic gonadotropin CTP amino acid sequences is glycosylated. In another embodiment, both of the chorionic gonadotropin CTP amino acid sequences are glycosylated. In another embodiment, 2 of the chorionic gonadotropin CTP amino acid sequences are glycosylated. In another embodiment, 2 or more of the chorionic gonadotropin CTP amino acid sequences are glycosylated. In another embodiment, all of the chorionic gonadotropin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites. Each possibility represents a separate embodiment of the present invention.

In some embodiments, "homology" according to the present invention also encompasses deletions, insertions, or substitution variants, including an amino acid substitution thereof, and biologically active polypeptide fragments thereof.

In some embodiments, human growth hormone (hGH) is utilized according to the teachings of the present invention. In some embodiments, the attachment of CTP sequence to both the amino and carboxy termini of the hGH protein results in increased potency (FIGS. 2, 3, 5, 7 and 9). In some embodiments, the attachment of CTP sequence to both the amino and carboxy termini of the hGH protein results in prolonged in-vivo activity. In one embodiment, CTP-hGH polypeptides of the present invention are set forth in SEQ ID NO: 39-41.

As provided herein, growth gain was demonstrated in hypophysectomized rats (which have no growth hormone secretion) following injections of CTP-hGH. As further provided herein, growth grain with excellent correlation to the patients' catch up growth was demonstrated in pre-pubertal growth hormone deficient children (see Example 10, herein).

In one embodiment, provided herein is a method of achieving normal growth recovery of a pre-pubertal growth hormone deficient child, the method comprising administering a pharmaceutical composition comprising a CTP-modified growth hormone provided herein. In another embodiment, provided herein is a method of achieving growth recovery of a pre-pubertal growth hormone deficient child, the method comprising administering a pharmaceutical composition comprising a CTP-modified growth hormone provided herein.

In one embodiment, the phrase "human growth hormone" (hGH) refers to a polypeptide, such as set forth in Genbank Accession No. P01241 (SEQ ID NO: 47), exhibiting hGH activity (i.e. stimulation of growth).

In another embodiment, "human growth hormone" (hGH) refers to a polypeptide, such as set forth in Genbank Accession No. P01241, exhibiting hGH activity (i.e. stimulation of growth). In another embodiment, "GH" of the present invention also refers to homologues. In another embodiment, a GH amino acid sequence of the methods and compositions the present invention is at least 50% homologous to a GH sequence set forth herein as determined using BlastP software of the National Center of Biotechnology Information (NCBI) using default parameters. In another embodiment, the percent homology is 60%. In another embodiment, the percent homology is 70%. In another embodiment, the percent homology is 80%. In another embodiment, the percent homology is 90%. In another embodiment, the percent homology is at least 95%. In another embodiment, the percent homology is greater than 95%. Each possibility represents a separate embodiment of the present invention.

Exemplary CTP-GH polypeptides and CTP-hGH polypeptides of the present invention are set forth in SEQ ID NO: 39, SEQ ID NO: 40 and SEQ ID NO: 41.

In another embodiment, the methods of the present invention provide a growth hormone (GH) peptide having additionally at least one CTP amino acid peptide on the N-terminus and at least one CTP amino acid peptide on the C-terminus for stimulating muscle growth. In another embodiment, the methods of the present invention provide a GH peptide having additionally one CTP amino acid peptide on the N-terminus and two CTP amino acid peptides on the C-terminus for stimulating muscle growth. In another embodiment, the methods of the present invention provide a GH peptide set forth in SEQ ID NO: 23 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 36 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 37 having additionally at least one CTP amino acid peptide on the N-terminus for stimulating muscle growth. In another embodiment, the methods of the present invention provide a GH peptide set forth in SEQ ID NO: 38, having additionally at least one CTP amino acid peptide on the N-terminus for stimulating muscle growth. In another embodiment, the methods of the present invention provide a GH peptide set forth in SEQ ID NO: 39 for stimulating muscle growth. In another embodiment, the methods of the present invention provide a GH peptide set forth in SEQ ID NO: 40 for stimulating muscle growth. In another embodiment, the methods of the present invention provide a GH peptide set forth in SEQ ID NO: 41 for stimulating muscle growth. In another embodiment, the methods of the present invention provide a GH peptide set forth in SEQ ID NO: 42 having additionally at least one CTP amino acid peptide on the N-terminus for stimulating muscle growth. In another embodiment, the methods of the present invention provide a GH peptide modified by CTPs as provided herein for stimulating muscle growth.

In another embodiment, the methods of the present invention provide a nucleic acid sequence encoding a GH peptide having additionally at least one CTP amino acid peptide on the N-terminus and at least one CTP amino acid peptide on the C-terminus for stimulating muscle growth. In another embodiment, the methods of the present invention provide a nucleic acid sequence encoding a GH peptide having additionally one CTP amino acid peptide on the N-terminus and two CTP amino acid peptides on the C-terminus for stimulating muscle growth. In one embodiment, the methods of the present invention provide a nucleic acid of SEQ ID NO: 44 encoding a GH peptide comprising one CTP amino acid peptide on the N-terminus and one CTP amino acid peptides on the C-terminus for stimulation muscle growth. In another embodiment, the methods of the present invention provide a nucleic acid of SEQ ID NO: 45 encoding a GH peptide comprising one CTP amino acid peptide on the N-terminus and two CTP amino acid peptides on the C-terminus for stimulating muscle growth. In another embodiment, the methods of the present invention provide a nucleic acid of SEQ ID NO: 46 encoding a GH peptide and one CTP amino acid peptide on the N-terminus and two CTP amino acid peptides on the C-terminus for stimulating muscle growth.

In one embodiment, the present invention provides a method of reducing the dosing frequency of a growth hormone in a subject, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the present invention provides a method of improving the area under the curve (AUC) of a growth hormone in a subject, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the present invention provides a formulation comprising a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, wherein said formulation has increased stability. In one embodiment, the formulation is stable for at least one year. In another embodiment, the formulation is stable for at least two years.

In one embodiment, the present invention provides a method of treating a subject in need of GH therapy, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby reducing the dosing frequency of a growth hormone in a subject.

In another embodiment, the present invention provides a method of increasing insulin-like growth factor (IGF-1) levels in a subject, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby increasing insulin-like growth factor (IGF-1) levels in a subject.

In another embodiment, the present invention provides a method of maintaining insulin-like growth factor (IGF-1) levels in a subject, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby maintaining insulin-like growth factor (IGF-1) levels in a subject. In another embodiment, the IGF-1 levels are kept in a defined range, as further provided herein.

In another embodiment, the present invention provides a method of increasing and maintaining insulin-like growth factor (IGF-1) levels within a defined range in a subject, comprising administering to said subject a therapeutically effective amount of a polypeptide consisting of a growth hormone, one chorionic gonadotropin carboxy terminal peptide (CTP) attached to the amino terminus of said growth hormone, and two chorionic gonadotropin CTPs attached to the carboxy terminus of said growth hormone, and wherein said polypeptide optionally consists of a signal peptide attached to the amino terminus of said one CTP, thereby increasing and maintaining insulin-like growth factor (IGF-1) levels within a defined range in a subject.

In another embodiment, the defined range is a therapeutic dose range achieved by administering a CTP-modified growth hormone provided herein. In another embodiment, the defined range is one in which the Cmax and Ctrough of the sinusoidal behavior of IGF-1 are maintained following consecutive administrations of a CTP-modified growth hormone as further provided herein (see Example 15). In another embodiment, the defined range is a therapeutic dose range for consecutively administering a CTP-modified growth hormone provided herein with excellent responsiveness in a subject and with minimal need for dose modification. In another embodiment, the defined range is comparable to the range of IGF-1 levels in individuals that are considered to be normal. In another embodiment, the defined range is the normal range of IGF-1 levels/values in normal individuals. In another yet embodiment, the defined range is within the normal range when IGF-1 SDS values are within ±2 SDS.

In another embodiment, the methods of the present invention provide any of the CTP-modified GH peptides described herein, for stimulating bone growth.

In another embodiment, the methods of the present invention provide a nucleic acid sequence encoding any of the CTP-modified GH peptides described herein, for stimulating bone growth.

In another embodiment, conjugated growth hormones of this invention are used in the same manner as unmodified growth hormones. In another embodiment, conjugated growth hormones of this invention have an increased circulating half-life and plasma residence time, decreased clearance, and increased clinical activity in vivo. In another embodiment, due to the improved properties of the conjugated growth hormones as described herein, these conjugates are administered less frequently than unmodified growth hormones. In another embodiment, conjugated growth hormones as described herein are administered once a week to once every two weeks. In another embodiment, conjugated growth hormones as described herein are administered once every two weeks to once every three weeks. In another embodiment, conjugated growth hormones as described herein are administered once a day to three times a week. In another embodiment, decreased frequency of administration will result in improved patient compliance leading to improved treatment outcomes, as well as improved patient quality of life. In another embodiment, compared to conventional conjugates of growth hormones linked to poly(ethylene glycol) it has been found that growth hormone CTP conjugates having the molecular weight and linker structure of the conjugates of this invention have an improved potency, improved stability, elevated AUC levels, enhanced circulating half-life. In another embodiment, compared to conventional conjugates of growth hormones linked to poly(ethylene glycol) it has been found that growth hormones having the molecular weight and linker structure of the conjugates of this invention have an improved potency, improved stability, elevated AUC levels, enhanced circulating half-life. In another embodiment, a therapeutically effective amount of a conjugated growth hormone is the amount of conjugate necessary for the in vivo measurable expected biological activity. In another embodiment, a growth hormone utilized according to the teachings of the present invention exhibits increased potency. In some embodiments, the attachment of CTP sequence to both the amino and carboxy termini of a growth hormone results in prolonged in-vivo activity.

In another embodiment, a therapeutically effective amount of a conjugated growth hormone is determined according to factors as the exact type of condition being treated, the condition of the patient being treated, as well as the other ingredients in the composition. In another embodiment, a therapeutically effective amount of a conjugated growth hormone is 0.01 to 10 µg per kg body weight administered once a week. In another embodiment, a therapeutically effective amount of a conjugated growth hormone is 0.1 to 1 µg per kg body weight, administered once a week. In another embodiment, a pharmaceutical composition comprising a conjugated growth hormone is formulated at strength effective for administration by various means to a human patient.

In another embodiment, the growth hormone is any growth hormone known to one of skill in the art. In another embodiment, the growth hormone is a human growth hormone. In another embodiment, the growth hormone is a non-human growth hormone. In another embodiment, the nucleotide sequence and/or the amino acid sequence of a growth hormone is available in a gene bank database. In another embodiment, the growth hormone is a homologue. In another embodiment, a homologue also refers to a deletion, insertion, or substitution variant, including an amino acid substitution, thereof and biologically active polypeptide fragments thereof.

In another embodiment, the growth hormone is variant of hGH missing exons 2, 3, 4, or any combination thereof. In another embodiment, the growth hormone comprises a signal peptide. In another embodiment, the growth hormone comprises a signal cleavage site. In another embodiment, polypeptides comprising GH modified by CTPs of the present invention comprise recombinant GH.

In another embodiment, the methods of the present invention provide a GH peptide of the present invention for maintaining muscle quality.

In another embodiment, the methods of the present invention provide a GH of the present invention for maintaining bone quality.

In another embodiment, the methods of the present invention provide a GH-CTP nucleic acid sequence of the present invention for maintaining bone quality.

In another embodiment, the methods of the present invention provide any of the CTP-modified GH peptides described herein, for treating a wasting disease.

In another embodiment, the methods of the present invention provide a nucleic acid sequence encoding any of the CTP-modified GH peptides described herein, for treating a wasting disease.

In another embodiment, the methods of the present invention provide any of the CTP-modified GH peptides described herein, for increasing cardiac function.

In another embodiment, the methods of the present invention provide a nucleic acid sequence encoding any of the CTP-modified GH peptides described herein, for increasing cardiac function.

In another embodiment, the methods of the present invention provide a GH peptides described herein, for increasing lipolysis.

In another embodiment, the methods of the present invention provide a nucleic acid sequence encoding any of the CTP-modified GH peptides described herein, for increasing lipolysis.

In another embodiment, the methods of the present invention provide any of the CTP-modified GH peptides described herein, for improving fluid balance.

In another embodiment, a growth hormone of the invention comprises the gene bank amino acid deposited sequence under accession no. AAA72260. In another embodiment, a growth hormone of the invention comprises the gene bank amino acid deposited sequence under accession no. AAK69708. In another embodiment, a growth hormone of the invention comprises the gene bank amino acid deposited sequence under accession no. CAA01435. In another embodiment, a growth hormone of the invention comprises the gene bank amino acid deposited sequence under accession no. CAA01329. In another embodiment, a growth hormone of the invention comprises the gene bank amino acid deposited sequence under accession no. CAA00380. In another embodiment, a growth hormone of the invention comprises the gene bank amino acid deposited sequence under accession no. AAA72555. In another embodiment, a growth hormone of the invention comprises the gene bank amino acid deposited sequence under accession no. NP_000506.2. In another embodiment, a growth hormone of the invention comprises the gene bank amino acid deposited sequence under accession no. NP_072053.1. In another embodiment, a growth hormone of the invention comprises the gene bank amino acid deposited sequence under accession no. NP_072054.1. In another embodiment, a growth hormone of the invention comprises the gene bank amino acid deposited sequence under accession no. NP_072055.1. In another embodiment, a growth hormone of the invention comprises the gene bank amino acid deposited sequence under accession no. NP_072056.1.

In another embodiment, the methods of the present invention provide a nucleic acid sequence encoding a GH peptide having additionally at least one CTP amino acid peptide on the N-terminus and at least one CTP amino acid peptide on the C-terminus for improving fluid balance. In another embodiment, the methods of the present invention provide a nucleic acid sequence encoding a GH peptide having additionally one CTP amino acid peptide on the N-terminus and two CTP amino acid peptides on the C-terminus for improving fluid balance. In one embodiment, the methods of the present invention provide a nucleic acid of SEQ ID NO: 44 encoding a GH peptide comprising one CTP amino acid peptide on the N-terminus and one CTP amino acid peptides on the C-terminus for improving fluid balance. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving fluid balance. In another embodiment, the methods of the present invention provide a nucleic acid of SEQ ID NO: 46 encoding a GH peptide and one CTP amino acid peptide on the N-terminus and two CTP amino acid peptides on the C-terminus for improving fluid balance.

In another embodiment, the methods of the present invention provide a GH peptide having additionally at least one CTP amino acid peptide on the N-terminus and at least one CTP amino acid peptide on the C-terminus for treating osteoporosis. In another embodiment, the methods of the present invention provide a GH peptide having additionally one CTP amino acid peptide on the N-terminus and two CTP amino acid peptides on the C-terminus for treating osteoporosis. In another embodiment, the methods of the present invention provide a GH peptide set forth in SEQ ID NO: 23 having additionally at least one CTP amino acid peptide on the N-terminus and at least one CTP amino acid peptide on the C-terminus for treating osteoporosis. In another embodiment, the methods of the present invention provide a GH peptide set forth in SEQ ID NO: 36 having additionally at least one CTP amino acid peptide on the N-terminus and at least one CTP amino acid peptide on the C-terminus for treating osteoporosis. In another embodiment, the methods of the present invention provide a GH peptide set forth in SEQ ID NO: 37 having additionally at least one CTP amino acid peptide on the N-terminus for treating osteoporosis. In another embodiment, the methods of the present invention provide a GH peptide set forth in SEQ ID NO: 38 having additionally at least one CTP amino acid peptide on the N-terminus for treating osteoporosis. In another embodiment, the methods of the present invention provide a GH peptide set forth in SEQ ID NO: 39 for treating osteoporosis. In another embodiment, the methods of the present invention provide a GH peptide set forth in SEQ ID NO: 40 for treating osteoporosis. In another embodiment, the methods of the present invention provide a GH peptide set forth in SEQ ID NO: 41 for treating osteoporosis. In another embodiment, the methods of the present invention provide a GH peptide set forth in SEQ ID NO: 42 having additionally at least one CTP amino acid peptide on the N-terminus for treating osteoporosis. In another embodiment, the methods of the present invention provide a GH peptide modified by CTPs, as provided herein, for treating osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for treating osteoporosis. In another embodiment, the methods of the present invention provide a nucleic acid sequence encoding a GH peptide having additionally one CTP amino acid peptide on the N-terminus and two CTP amino acid peptides on the C-terminus for treating osteoporosis. In one embodiment, the methods of the present invention provide a nucleic acid of SEQ ID NO: 44 encoding a GH peptide comprising one CTP amino acid peptide on the N-terminus and one CTP amino acid peptides on the C-terminus for for treating osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for treating osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for treating osteoporosis.

In another embodiment, the methods of the present invention provide a GH peptide having additionally at least one CTP amino acid peptide on the N-terminus and at least one CTP amino acid peptide on the C-terminus for inhibiting osteoporosis. In another embodiment, the methods of the present invention provide a GH peptide having additionally one CTP amino acid peptide on the N-terminus and two CTP amino acid peptides on the C-terminus for inhibiting osteoporosis. In another embodiment, the methods of the present invention provide a GH peptide set forth in SEQ ID NO: 23 having additionally at least one CTP amino acid peptide on the N-terminus and at least one CTP amino acid peptide on the C-terminus for inhibiting osteoporosis. In another embodiment, the methods of the present invention provide a GH peptide set forth in SEQ ID NO: 36 having additionally at least one CTP amino acid peptide on the N-terminus and at least one CTP amino acid peptide on the C-terminus for inhibiting osteoporosis. In another embodiment, the methods of the present invention provide a GH peptide set forth in SEQ ID NO: 37 having additionally at least one CTP amino acid peptide on the N-terminus for inhibiting osteoporosis. In another embodiment, the methods of the present invention provide a GH peptide set forth in SEQ ID NO: 38 having additionally at least one CTP amino acid peptide on the N-terminus for inhibiting osteoporosis. In another embodiment, the methods of the present invention provide a GH peptide set forth in SEQ ID NO: 39 for inhibiting osteoporosis. In another embodiment, the methods of the present invention provide a GH peptide set forth in SEQ ID NO: 40 for inhibiting osteoporosis. In another embodiment, the methods of the present invention provide a GH peptide set forth in SEQ ID NO: 41 for inhibiting osteoporosis. In another embodiment, the methods of the present invention provide a GH peptide set forth in SEQ ID NO: 42 having additionally at least one CTP amino acid peptide on the N-terminus for inhibiting osteoporosis. In another embodiment, the methods of the present invention provide a GH peptide modified by CTPs, as provided herein, for inhibiting osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for inhibiting osteoporosis. In another embodiment, the methods of the present invention provide a nucleic acid sequence encoding a GH peptide having additionally one CTP amino acid peptide on the N-terminus and two CTP amino acid peptides on the C-terminus for inhibiting osteoporosis. In one embodiment, the methods of the present invention provide a nucleic acid of SEQ ID NO: 44 encoding a GH peptide comprising one CTP amino acid peptide on the N-terminus and one CTP amino acid peptides on the C-terminus for inhibiting osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for inhibiting osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for inhibiting osteoporosis.

In another embodiment, the methods of the present invention provide a GH peptide of the present invention for improving exercise capacity.

In another embodiment, the methods of the present invention provide a GH peptide having additionally at least one CTP amino acid peptide on the N-terminus and at least one CTP amino acid peptide on the C-terminus for improving lung function. In another embodiment, the methods of the present invention provide a GH peptide having additionally one CTP amino acid peptide on the N-terminus and two CTP amino acid peptides on the C-terminus for improving lung function. In another embodiment, the methods of the present invention provide a GH peptide set forth in SEQ ID NO: 23 having additionally at least one CTP amino acid peptide on the N-terminus and at least one CTP amino acid peptide on the C-terminus for improving lung function. In another embodiment, the methods of the present invention provide a GH peptide set forth in SEQ ID NO: 36 having additionally at least one CTP amino acid peptide on the N-terminus and at least one CTP amino acid peptide on the C-terminus for improving lung function. In another embodiment, the methods of the present invention provide a GH peptide set forth in SEQ ID NO: 37 having additionally at least one CTP amino acid peptide on the N-terminus for improving lung function. In another embodiment, the methods of the present invention provide a GH peptide set forth in SEQ ID NO: 38 having additionally at least one CTP amino acid peptide on the N-terminus for improving lung function. In another embodiment, the methods of the present invention provide a GH peptide set forth in SEQ ID NO: 39 for improving lung function. In another embodiment, the methods of the present invention provide a GH peptide set forth in SEQ ID NO: 40 for improving lung function. In another embodiment, the methods of the present invention provide a GH peptide set forth in SEQ ID NO: 41 for improving lung function. In another embodiment, the methods of the present invention provide a GH peptide set forth in SEQ ID NO: 42 having additionally at least one CTP amino acid peptide on the N-terminus for improving lung function. In another embodiment, the methods of the present invention provide a GH peptide modified by CTPs as provided herein for improving lung function.

In another embodiment, the methods of the present invention provide a nucleic acid sequence encoding a GH peptide having additionally at least one CTP amino acid peptide on the N-terminus and at least one CTP amino acid peptide on the C-terminus for improving lung function. In another embodiment, the methods of the present invention provide a nucleic acid sequence encoding a GH peptide having additionally one CTP amino acid peptide on the N-terminus and two CTP amino acid peptides on the C-terminus for improving lung function. In one embodiment, the methods of the present invention provide a nucleic acid of SEQ ID NO: 44 encoding a GH peptide comprising one CTP amino acid peptide on the N-terminus and one CTP amino acid peptides on the C-terminus for improving lung function. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving lung function. In another embodiment, the methods of the present invention provide a nucleic acid of SEQ ID NO: 46 encoding a GH peptide and one CTP amino acid peptide on the N-terminus and two CTP amino acid peptides on the C-terminus for improving lung function.

In another embodiment, the methods of the present invention provide a GH peptide having additionally at least one CTP amino acid peptide on the N-terminus and at least one CTP amino acid peptide on the C-terminus for improving immunity. In another embodiment, the methods of the present invention provide a GH peptide having additionally one CTP amino acid peptide on the N-terminus and two CTP amino acid peptides on the C-terminus for improving immunity. In another embodiment, the methods of the present invention provide a GH peptide set forth in SEQ ID NO: 23 having additionally at least one CTP amino acid peptide on the N-terminus and at least one CTP amino acid peptide on the C-terminus for improving immunity. In another embodiment, the methods of the present invention provide a GH peptide set forth in SEQ ID NO: 36 having additionally at least one CTP amino acid peptide on the N-terminus and at least one CTP amino acid peptide on the C-terminus for improving immunity. In another embodiment, the methods of the present invention provide a GH peptide set forth in SEQ ID NO: 37 having additionally at least one CTP amino acid peptide on the N-terminus for improving immunity. In another embodiment, the methods of the present invention provide a GH peptide set forth in SEQ ID NO: 38 having additionally at least one CTP amino acid peptide on the N-terminus for improving immunity. In another embodiment, the methods of the present invention provide a GH peptide set forth in SEQ ID NO: 39 for improving immunity. In another embodiment, the methods of the present invention provide a GH peptide set forth in SEQ ID NO: 40 for improving immunity. In another embodiment, the methods of the present invention provide a GH peptide set forth in SEQ ID NO: 41 for improving immunity. In another embodiment, the methods of the present invention provide a GH peptide set forth in SEQ ID NO: 42 having additionally at least one CTP amino acid peptide on the N-terminus for improving immunity. In another embodiment, the methods of the present invention provide a GH peptide modified by CTPs, as provided herein, for improving immunity.

In another embodiment, the methods of the present invention provide a nucleic acid sequence encoding a GH peptide having additionally at least one CTP amino acid peptide on the N-terminus and at least one CTP amino acid peptide on the C-terminus for improving immunity. In another embodiment, the methods of the present invention provide a nucleic acid sequence encoding a GH peptide having additionally one CTP amino acid peptide on the N-terminus and two CTP amino acid peptides on the C-terminus for improving immunity. In one embodiment, the methods of the present invention provide a nucleic acid of SEQ ID NO: 44 encoding a GH peptide comprising one CTP amino acid peptide on the N-terminus and one CTP amino acid peptides on the C-terminus for improving immunity. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving immunity. In another embodiment, the methods of the present invention provide a nucleic acid of SEQ ID NO: 46 encoding a GH peptide and one CTP amino acid peptide on the N-terminus and two CTP amino acid peptides on the C-terminus for improving immunity.

In another embodiment, the methods of the present invention provide a GH peptide having additionally at least one CTP amino acid peptide on the N-terminus and at least one CTP amino acid peptide on the C-terminus for regrowing vital organs. In another embodiment, the methods of the present invention provide a GH peptide having additionally one CTP amino acid peptide on the N-terminus and two CTP amino acid peptides on the C-terminus for regrowing vital organs. In another embodiment, the methods of the present invention provide a GH peptide set forth in SEQ ID NO: 23 having additionally at least one CTP amino acid peptide on the N-terminus and at least one CTP amino acid peptide on the C-terminus for regrowing vital organs. In another embodiment, the methods of the present invention provide a GH peptide set forth in SEQ ID NO: 36 having additionally at least one CTP amino acid peptide on the N-terminus and at least one CTP amino acid peptide on the C-terminus for regrowing vital organs. In another embodiment, the methods of the present invention provide a GH peptide set forth in SEQ ID NO: 37 having additionally at least one CTP amino acid peptide on the N-terminus for regrowing vital organs. In another embodiment, the methods of the present invention provide a GH peptide set forth in SEQ ID NO: 38 having additionally at least one CTP amino acid peptide on the N-terminus for regrowing vital organs. In another embodiment, the methods of the present invention provide a GH peptide set forth in SEQ ID NO: 39 for regrowing vital organs. In another embodiment, the methods of the present invention provide a GH peptide set forth in SEQ ID NO: 40 for regrowing vital organs. In another embodiment, the methods of the present invention provide a GH peptide set forth in SEQ ID NO: 41 for regrowing vital organs. In another embodiment, the methods of the present invention provide a GH peptide set forth in SEQ ID NO: 42 having additionally at least one CTP amino acid peptide on the N-terminus for regrowing vital organs. In another embodiment, the methods of the present invention provide a GH peptide modified by CTPs, as provided herein, for regrowing vital organs.

In another embodiment, the methods of the present invention provide a nucleic acid sequence encoding a GH peptide having additionally at least one CTP amino acid peptide on the N-terminus and at least one CTP amino acid peptide on the C-terminus for regrowing vital organs. In another embodiment, the methods of the present invention provide a nucleic acid sequence encoding a GH peptide having additionally one CTP amino acid peptide on the N-terminus and two CTP amino acid peptides on the C-terminus for regrowing vital organs. In one embodiment, the methods of the present invention provide a nucleic acid of SEQ ID NO: 44 encoding a GH peptide comprising one CTP amino acid peptide on the N-terminus and one CTP amino acid peptides on the C-terminus for for regrowing vital organs. In another embodiment, the methods of the present invention provide a nucleic acid of SEQ ID NO: 45 encoding a GH peptide comprising one CTP amino acid peptide on the N-terminus and two CTP amino acid peptides on the C-terminus for regrowing vital organs. In another embodiment, the methods of the present invention provide a nucleic acid of SEQ ID NO: 46 encoding a GH peptide and one CTP amino acid peptide on the N-terminus and two CTP amino acid peptides on the C-terminus for regrowing vital organs.

In another embodiment, the methods of the present invention provide a GH peptide of the present invention for increasing sense of well-being.

In another embodiment, the methods of the present invention provide a GH peptide having additionally at least one CTP amino acid peptide on the N-terminus and at least one CTP amino acid peptide on the C-terminus for restoring REM sleep. In another embodiment, the methods of the present invention provide a GH peptide having additionally one CTP amino acid peptide on the N-terminus and two CTP amino acid peptides on the C-terminus for restoring REM sleep. In another embodiment, the methods of the present invention provide a GH peptide set forth in SEQ ID NO: 23 having additionally at least one CTP amino acid peptide on the N-terminus and at least one CTP amino acid peptide on the C-terminus for restoring REM sleep. In another embodiment, the methods of the present invention provide a GH peptide set forth in SEQ ID NO: 36 having additionally at least one CTP amino acid peptide on the N-terminus and at least one CTP amino acid peptide on the C-terminus for restoring REM sleep. In another embodiment, the methods of the present invention provide a GH peptide set forth in SEQ ID NO: 37 having additionally at least one CTP amino acid peptide on the N-terminus for restoring REM sleep. In another embodiment, the methods of the present invention provide a GH peptide set forth in SEQ ID NO: 38 having additionally at least one CTP amino acid peptide on the N-terminus for restoring REM sleep. In another embodiment, the methods of the present invention provide a GH peptide set forth in SEQ ID NO: 39 for restoring REM sleep. In another embodiment, the methods of the present invention provide a GH peptide set forth in SEQ ID NO: 40 for restoring REM sleep. In another embodiment, the methods of the present invention provide a GH peptide set forth in SEQ ID NO: 41 for restoring REM sleep. In another embodiment, the methods of the present invention provide a GH peptide set forth in SEQ ID NO: 42 having additionally at least one CTP amino acid peptide on the N-terminus for restoring REM sleep. In another embodiment, the methods of the present invention provide a GH peptide modified by CTPs, as provided herein, for restoring REM sleep.

In another embodiment, the methods of the present invention provide a nucleic acid sequence encoding a GH peptide having additionally at least one CTP amino acid peptide on the N-terminus and at least one CTP amino acid peptide on the C-terminus for restoring REM sleep. In another embodiment, the methods of the present invention provide a nucleic acid sequence encoding a GH peptide having additionally one CTP amino acid peptide on the N-terminus and two CTP amino acid peptides on the C-terminus for restoring REM sleep. In one embodiment, the methods of the present invention provide a nucleic acid of SEQ ID NO: 44 encoding a GH peptide comprising one CTP amino acid peptide on the N-terminus and one CTP amino acid peptides on the C-terminus for restoring REM sleep. In another embodiment, the methods of the present invention provide a nucleic acid of SEQ ID NO: 45 encoding a GH peptide comprising one CTP amino acid peptide on the N-terminus and two CTP amino acid peptides on the C-terminus for restoring REM sleep. In another embodiment, the methods of the present invention provide a nucleic acid of SEQ ID NO: 46 encoding a GH peptide and one CTP amino acid peptide on the N-terminus and two CTP amino acid peptides on the C-terminus for restoring REM sleep.

In another embodiment, the methods of the present invention provide a nucleic acid sequence encoding a GH protein as described herein. In another embodiment, the methods of the present invention provide a nucleic acid sequence encoding polypeptide comprising hGH modified by CTPs for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof.

In some embodiments, "homology" according to the present invention also encompasses deletions, insertions, or substitution variants, including an amino acid substitution, thereof and biologically active polypeptide fragments thereof. In one embodiment the substitution variant is one in which the glutamine in position 65 of hGH is substituted by a valine [Gellerfors et al., J Pharm Biomed Anal 1989, 7:173-83].

In another embodiment, the nucleic acid molecule encoding a growth hormone as described herein encodes any amino acid sequence of a growth hormone known to one of skill in the art. In another embodiment, the nucleic acid molecule encoding a growth hormone as described herein encodes an hGH. In another embodiment, the nucleic acid molecule encoding a growth hormone comprises the gene bank nucleic acid deposited sequence under accession no. NM_000515.3. In another embodiment, the nucleic acid molecule encoding a growth hormone comprises the gene bank nucleic acid deposited sequence under accession no. NM_022559.2. In another embodiment, the nucleic acid molecule encoding a growth hormone comprises the gene bank nucleic acid deposited sequence under accession no. NM_022560.2. In another embodiment, the nucleic acid molecule encoding a growth hormone comprises the gene bank nucleic acid deposited sequence under accession no. NM_022561.2. In another embodiment, the nucleic acid molecule encoding a growth hormone comprises the gene bank nucleic acid deposited sequence under accession no. NM_022562.2.

In one embodiment, the homologue also refers to a deletion, insertion, or substitution variant, including an amino acid substitution, thereof and biologically active polypeptide fragments thereof.

In another embodiment the polypeptide sequence of interest is an hGH. In another embodiment the polypeptide sequence of interest is a peptide or a protein including any modified form.

In another embodiment, the methods of the present invention provide hGH having additionally at least one CTP amino acid peptide on the N-terminus and at least one CTP amino acid peptide on the C-terminus for the treatment of wasting disease, AIDS, cachexia, or hGH deficiency.

In one embodiment, the invention is employed in veterinary medicine. In one embodiment, the present invention provides treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

In some embodiments, the CTP sequences modification is advantageous in permitting lower dosages to be used.

In some embodiments, "polypeptide" as used herein encompasses native polypeptides (either degradation products, synthetically synthesized polypeptides or recombinant polypeptides) and peptidomimetics (typically, synthetic polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinbelow.

In some embodiments, polypeptide bonds (—CO—NH—) within the polypeptide are substituted. In some embodiments, the polypeptide bonds are substituted by N-methylated bonds (—N(CH3)—CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2—). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2—). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the polypeptides of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides of the present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide of the present invention is synthesized using a polynucleotide encoding a polypeptide of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention.

In some embodiments, polynucleotides which express the polypeptides of the present invention are as set forth in SEQ ID NOs: 44, 45 and 46.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In some embodiments, signal sequences include, but are not limited to the endogenous signal sequence for EPO as set forth in SEQ ID NO: 19 or the endogenous signal sequence for IFN-β1 as set forth in SEQ ID NO: 26. In another embodiment, the signal sequence is N-terminal to the CTP sequence that is in turn N-terminal to the polypeptide sequence of interest; e.g. the sequence is (a) signal sequence—(b) CTP—(c) sequence of interest—(d) optionally 1 or more additional CTP sequences. In another embodiment, 1 or more CTP sequences is inserted between the signal sequence of a polypeptide sequence of interest and the polypeptide sequence of interest itself, thus interrupting the wild-type sequence of interest. Each possibility represents a separate embodiment of the present invention.

In another embodiment, the growth hormone further comprises a signal peptide. In some embodiments, signal sequences include, but are not limited to the endogenous signal sequence. In some embodiments, signal sequences include, but are not limited to the endogenous signal sequence of any known growth hormone or growth hormones. In another embodiment, the polypeptides and methods of the present invention provide a growth hormone having additionally a signal peptide of comprising the following amino acid sequence:

```
                                        (SEQ ID NO: 49)
MATGSRTSLLLAFGLLCLPWLQEGSA.
```

In one embodiment, following expression and secretion, the signal peptides are cleaved from the precursor proteins resulting in the mature proteins.

In some embodiments, polynucleotides of the present invention are prepared using PCR techniques using procedures and methods known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1 and FIG. 3.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in $E.\ coli$; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In some embodiments, the recombinant polypeptides are synthesized and purified; their therapeutic efficacy can be assayed in vivo or in vitro. In one embodiment, production of GH modified by CTPs using recombinant DNA technology is performed.

In some embodiments, the recombinant polypeptides are synthesized and purified; their therapeutic efficacy can be assayed either in vivo or in vitro. In one embodiment, the binding activities of the recombinant GH modified by CTPs of the present invention can be ascertained using various assays.

In one embodiment, the present invention comprises CTP-GH-CTP polypeptides. In one embodiment, recombinant DNA technology methods are used for the production of CTP-GH-CTP polypeptides. In one embodiment, the present invention comprises CTP-GH-CTP-CTP polypeptides. In one embodiment, recombinant DNA technology methods are used for the production of CTP-GH-CTP-CTP polypeptides, as illustrated in Example 1 and FIG. 1. In one embodiment, the therapeutic efficacy of the CTP-GH-CTP polypeptides or CTP-GH-CTP-CTP polypeptides of the present invention is assayed either in vivo. In one embodiment, the therapeutic efficacy of the CTP-GH-CTP or CTP-GH-CTP-CTP polypeptides of the present invention is assayed either in vitro. In one embodiment, the binding activities of the recombinant GH polypeptides of the present invention are measured using Nb2 (a prolactin-dependent rat lymphoma cell line (ECACC Cell Bank)) or a FCD-P1 murine cell line, previously transfected with human growth hormone receptor. In one embodiment, binding of GH to these receptors induces cell proliferation which in one embodiment is measured by the levels of MTT cellular stain as a function of GH activity. In one embodiment, in vivo activity is deduced by measuring weight gain over time in treated growth hormone deficient animals.

In one embodiment, the present invention provides a method of inducing growth or weight gain in a subject, comprising administering to the subject a therapeutically effective amount of a polypeptide comprising a growth hormone, one chorionic gonadotropin carboxy terminal peptide (CTP) attached to an amino terminus of said growth hormone, and two chorionic gonadotropin CTPs attached to a carboxy terminus of the growth hormone, thereby inducing growth or weight gain in a subject.

In another embodiment, the present invention provides a method of inducing growth or weight gain in a non-human subject, comprising the step of administering to said non-human subject a therapeutically effective amount of an expression vector comprising a polynucleotide consisting of a nucleic acid encoding a polypeptide, said polypeptide consisting of a non-human growth hormone, one chorionic gonadotropin carboxy terminal peptide (CTP) attached to the amino terminus of said non-human growth hormone, and two chorionic gonadotropin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of inducing weight loss or decreasing body fat in a subject, comprising administering to said subject a therapeutically effective amount of a polypeptide comprising a growth hormone, one chorionic gonadotropin carboxy terminal peptide (CTP) attached to the amino terminus of said growth hormone, and two chorionic gonadotropin CTPs attached to the carboxy terminus of said growth hormone, thereby inducing weight loss or decreasing body fat in said subject. In one embodiment, said subject is obese. In another embodiment, said subject is overweight.

In another embodiment, the present invention provides a method of decreasing body fat in a non-human subject, comprising administering to said subject a therapeutically effective amount of an expression vector comprising a polynucleotide, said polynucleotide consisting of a non-human growth hormone, one chorionic gonadotropin carboxy terminal peptide (CTP) attached to the amino terminus of said non-human growth hormone, and two chorionic gonadotropin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of decreasing fat deposits in a subject. In another embodiment, the present invention provides a method of increasing muscle mass in a subject. In another embodiment, the present invention provides a method of promoting muscle growth in a subject. In another embodiment, the present invention provides a method of increasing muscle to fat ratio. In another embodiment, the present invention provides a method of decreasing body mass index (BMI) or Quetelet index.

In another embodiment, growth is measured by weight gain. In another embodiment, growth is measured by height gain. In another embodiment, growth is measured by weight gain. In another embodiment, growth is measured by muscle mass gain. In another embodiment, growth is measured by weight gain. In another embodiment, growth is measured by bone mass gain. In another embodiment, growth is measured by weight gain. In another embodiment, growth is measured by muscle mass gain. In another embodiment, the weight gain is due to bone and/or muscle mass gain. In another embodiment, growth is measured by any known measure known to one of skill in the art.

In some embodiment, human growth hormone polypeptides of the present invention can be used to treat a subject, with conditions related to growth and weight, such as a growth deficiency disorder, AIDS wasting, aging, impaired immune function of HIV-infected subjects, a catabolic illness, surgical recovery, a congestive cardiomyopathy, liver transplantation, liver regeneration after hepatectomy, chronic renal failure, renal osteodystrophy, osteoporosis, achondroplasia/hypochondroplasia, skeletal dysplasia, a chronic inflammatory or nutritional disorder such as Crohn's disease, short bowel syndrome, juvenile chronic arthritis, cystic fibrosis, male infertility, X-linked hypophosphatemic rickets, Down's syndrome, Spina bifida, Noonan Syndrome, obesity, impaired muscle strength and fibromyalgia. In some embodiments, interferon polypeptides of the present invention are used to treat a subject, with a variety of conditions such as hairy cell leukemia (HCL), Kaposi's sarcoma (KS), chronic myelogenous leukemia (CML), chronic Hepatitis C (CHC), condylomata acuminata (CA), chronic Hepatitis B, malignant melanoma, follicular non-Hodgkin's lymphoma, multiple sclerosis, chronic granulomatous disease, Mycobacterium avium complex (MAC), pulmonary fibrosis and osteoporosis.

In one embodiment, the polypeptides of the present invention can be provided to the individual per se. In one embodiment, the polypeptides of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the polypeptide sequence of interest, which is accountable for the biological effect.

In some embodiments, any of the compositions of this invention will comprise at least two CTP sequences bound to a protein of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which can be used interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

In one embodiment, where the pharmaceutical formulation or the pharmaceutical composition is administered via injection to a subject, it is done so using a syringe or a PEN device.

In another embodiment, polypeptides comprising GH modified by CTPs of the present invention are administered in a dose of 1-90 micrograms in 0.1-5 ml solution. In another embodiment, polypeptides comprising GH modified by CTPs are administered in a dose of 1-50 micrograms in 0.1-5 ml solution. In another embodiment, polypeptides comprising GH modified by CTPs are administered in a dose of 1-25 micrograms in 0.1-5 ml solution. In another embodiment, polypeptides comprising GH modified by CTPs are administered in a dose of 50-90 micrograms in 0.1-5 ml solution. In another embodiment, polypeptides comprising GH modified by CTPs are administered in a dose of 10-50 micrograms in 0.1-5 ml solution. In another embodiment, polypeptides comprising GH modified by CTPs are administered in a dose of 5 milligrams (mg) in 1 ml solution, or 10 mg in 1 ml solution, or 20 mg in 1 ml solution, or 40 mg in 1 ml solution.

In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection twice a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection three times a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every two weeks. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 17 days. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 19 days weeks. In one embodiment, administration is by intramuscular (IM) injection. In one embodiment, administration is by subcutaneous (SC) injection. In one embodiment, administration is by intravenous (IV) injection.

Various embodiments of dosage ranges are contemplated by this invention. The dosage of the polypeptide of the present invention, in one embodiment, is in the range of 0.05-80 mg/day. In another embodiment, the dosage is in the range of 0.05-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day. In another embodiment, the dosage is in the range of 0.5-50 mg/day. In another embodiment, the dosage is in the range of 5-80 mg/day. In another embodiment, the dosage is in the range of 35-65 mg/day. In another embodiment, the dosage is in the range of 35-65 mg/day. In another embodiment, the dosage is in the range of 20-60 mg/day. In another embodiment, the dosage is in the range of 40-60 mg/day. In another embodiment, the dosage is in a range of 45-60 mg/day. In another embodiment, the dosage is in the range of 40-60 mg/day. In another embodiment, the dosage is in a range of 60-120 mg/day. In another embodiment, the dosage is in the range of 120-240 mg/day. In another embodiment, the dosage is in the range of 40-60 mg/day. In another embodiment, the dosage is in a range of 240-400 mg/day. In another embodiment, the dosage is in a range of 45-60 mg/day. In another embodiment, the dosage is in the range of 15-25 mg/day. In another embodiment, the dosage is in the range of 5-10 mg/day. In another embodiment, the dosage is in the range of 55-65 mg/day.

In one embodiment, the dosage is 20 mg/day. In another embodiment, the dosage is 30 mg/day. In another embodiment, the dosage is 40 mg/day. In another embodiment, the dosage is 50 mg/day. In another embodiment, the dosage is 60 mg/day. In another embodiment, the dosage is 70 mg/day. In another embodiment, the dosage is 80 mg/day. In another embodiment, the dosage is 90 mg/day. In another embodiment, the dosage is 100 mg/day.

The dosage of the GH modified by CTPs of the present invention, in one embodiment, is in the range of 0.005-100 mg/week. In another embodiment, the dosage is in the range of 0.005-5 mg/week. In another embodiment, the dosage is in the range of 0.01-50 mg/week. In another embodiment, the dosage is in the range of 0.1-20 mg/week. In another embodiment, the dosage is in the range of 0.1-10 mg/week. In another embodiment, the dosage is in the range of 0.01-5 mg/week. In another embodiment, the dosage is in the range of 0.001-0.01 mg/week. In another embodiment, the dosage is in the range of 0.001-0.1 mg/week. In another embodiment, the dosage is in the range of 0.1-5 mg/week. In another embodiment, the dosage is in the range of 0.5-50 mg/week. In another embodiment, the dosage is in the range of 0.2-15 mg/week. In another embodiment, the dosage is in the range of 0.8-65 mg/week. In another embodiment, the dosage is in the range of 1-50 mg/week. In another embodiment, the dosage is in the range of 5-10 mg/week. In another embodiment, the dosage is in the range of 8-15 mg/week. In another embodiment, the dosage is in a range of 10-20 mg/week. In another embodiment, the dosage is in the range of 20-40 mg/week. In another embodiment, the dosage is in a range of 60-120 mg/week. In another embodiment, the dosage is in the range of 12-40 mg/week. In another embodiment, the dosage is in the range of 40-60 mg/week. In another embodiment, the dosage is in a range of 50-100 mg/week. In another embodiment, the dosage is in a range of 1-60 mg/week. In another embodiment, the dosage is in the range of 15-25 mg/week. In another embodiment, the dosage is in the range of 5-10 mg/week. In another embodiment, the dosage is in the range of 55-65 mg/week. In another embodiment, the dosage is in the range of 1-5 mg/week.

In another embodiment, the GH dosage given to a subject is 50% of the standard dosage given to a reference subject from the same population of subjects (e.g. children, elderly, men, women, GH deficient, specific nationality, etc). In another embodiment, the dosage is 30% of the dosage given to a subject from a specific population of subjects. In another embodiment, the dosage is 45% of the dosage given to a subject from a specific population of subjects. In another embodiment, the dosage is 100% of the dosage given to a subject from a specific population of subjects.

In another embodiment, the dosage is 1-5 mg/week. In another embodiment, the dosage is 2 mg/week. In another embodiment, the dosage is 4 mg/week. In another embodiment, the dosage is 1.2 mg/week. In another embodiment, the dosage is 1.8 mg/week. In another embodiment, the dosage is approximately the dosages described herein.

In another embodiment, the dosage is 1-5 mg/administration. In another embodiment, the dosage is 2 mg/administration. In another embodiment, the dosage is 4 mg/administration. In another embodiment, the dosage is 1.2 mg/administration. In another embodiment, the dosage is 1.8 mg/administration. In one embodiment, the composition is administered once a week. In another embodiment, the composition is administered once biweekly. In another embodiment, the composition is administered monthly. In another embodiment, the composition is administered daily.

In one embodiment, GH modified by CTPs is formulated in a liquid formulation.

In another embodiment, GH modified by CTPs is formulated in an intranasal dosage form. In another embodiment, GH modified by CTPs is formulated in an injectable dosage form. In another embodiment, GH modified by CTPs is administered to a subject in a dose ranging from 0.0001 mg to 0.6 mg. In another embodiment, GH modified by CTPs is administered to a subject in a dose ranging from 0.001 mg to 0.005 mg. In another embodiment, GH modified by CTPs is administered to a subject in a dose ranging from 0.005 mg to 0.01 mg. In another embodiment, GH modified by CTPs is administered to a subject in a dose ranging from 0.01 mg to 0.3 mg. In another embodiment, a GH modified by CTPs is administered to a subject in a dose in a dose ranging from 0.2 mg to 0.6 mg.

In another embodiment, GH modified by CTPs is administered to a subject in a dose ranging from 1-100 micrograms. In another embodiment, a GH modified by CTPs is administered to a subject in a dose ranging from 10-80 micrograms. In another embodiment, a GH modified by CTPs is administered to a subject in a dose ranging from 20-60 micrograms. In another embodiment, a GH modified by CTPs is administered to a subject in a dose ranging from 10-50 micrograms. In another embodiment, a GH modified by CTPs is administered to a subject in a dose ranging from 40-80 micrograms. In another embodiment, a GH modified by CTPs is administered to a subject in a dose ranging from 10-30 micrograms. In another embodiment, a GH modified by CTPs is administered to a subject in a dose ranging from 30-60 micrograms.

In another embodiment, GH modified by CTPs is administered to a subject in a dose ranging from 0.2 mg to 2 mg. In another embodiment, a GH modified by CTPs is administered to a subject in a dose ranging from 2 mg to 6 mg. In another embodiment, a GH modified by CTPs is administered to a subject in a dose ranging from 4 mg to 10 mg. In another embodiment, a GH modified by CTPs is administered to a subject in a dose ranging from 5 mg and 15 mg.

In another embodiment, a GH modified by CTPs is injected into the muscle (intramuscular injection). In another embodiment, a GH modified by CTPs is injected below the skin (subcutaneous injection). In another embodiment, a GH modified by CTPs is injected into the muscle. In another embodiment, a GH modified by CTPs is injected below the skin.

In another embodiment, the methods of the invention include increasing the compliance in the use of GH therapy, comprising providing to a subject in need thereof, a GH modified by CTPs, thereby increasing compliance in the use of growth hormone therapy.

In another embodiment, protein drugs of molecular weight lower than 50,000 daltons, such as GH modified by CTPs of the present invention are in general short-lived species in vivo, having short circulatory half-lives of several hours. In another embodiment, the subcutaneous route of administration in general provides slower release into the circulation. In another embodiment, the CTP modified polypeptide of the invention prolongs the half-live of protein drugs of molecular weight lower than 50,000 daltons, such as GH. In another embodiment, the CTP modified polypeptide of the invention enable interferons to exert their beneficial effects for a longer period of time.

In another embodiment, the immunogenicity of a CTP modified polypeptide comprising a GH modified by CTPs is equal to an isolated GH. In another embodiment, the immunogenicity of a CTP modified polypeptide comprising a GH modified by CTPs is comparable to an isolated GH. In another embodiment, modifying a GH as described herein with CTP peptides reduces the immunogenicity of the GH. In another embodiment, the CTP modified polypeptide comprising a GH is as active as an isolated GH protein. In another embodiment, the CTP modified polypeptide comprising a GH is more active than an isolated GH. In another embodiment, the CTP modified polypeptide comprising a GH maximizes the growth hormone's protective ability against degradation while minimizing reductions in bioactivity.

In another embodiment, the methods of the invention include increasing the compliance of subjects afflicted with chronic illnesses that are in need of a GH therapy. In another embodiment, the methods of the invention enable reduction in the dosing frequency of a GH by modifying the GH with CTPs as described hereinabove. In another embodiment, the term compliance comprises adherence. In another embodiment, the methods of the invention include increasing the compliance of patients in need of a GH therapy by reducing the frequency of administration of the GH. In another embodiment, reduction in the frequency of administration of the GH is achieved due to the CTP modifications which render the CTP-modified GH more stable. In another embodiment, reduction in the frequency of administration of the GH is achieved as a result of increasing T1/2 of the growth hormone. In another embodiment, reduction in the frequency of administration of the GH is achieved as a result of increasing the clearance time of the GH. In another embodiment, reduction in the frequency of administration of the growth hormone is achieved as a result of increasing the AUC measure of the growth hormone.

In another embodiment, the present invention provides a method of decreasing body fat in a non-human subject, comprising administering to said subject a therapeutically effective amount of an expression vector comprising a polynucleotide, said polynucleotide consisting of a non-human growth hormone, one chorionic gonadotropin carboxy terminal peptide (CTP) attached to the amino terminus of said non-human growth hormone, and two chorionic gonadotropin CTPs attached to the carboxy terminus of said non-human growth hormone, and wherein said polypeptide optionally consists of a signal peptide attached to the amino terminus of said one CTP, thereby inducing growth or weight gain in a non-human subject.

In another embodiment, the present invention provides a method of increasing insulin-like growth factor (IGF-1) levels in a human subject, comprising administering to said subject a therapeutically effective amount of a polypeptide comprising a growth hormone, one chorionic gonadotropin carboxy terminal peptide (CTP) attached to the amino terminus of said growth hormone, and two chorionic gonadotropin CTPs attached to the carboxy terminus of said growth hormone, thereby increasing IGF-1 levels in said subject.

In another embodiment, the present invention provides a method of increasing insulin-like growth factor (IGF-1) levels in a non-human subject, comprising administering to said subject a therapeutically effective amount of an expression vector comprising a polynucleotide, said polynucleotide consisting of a non-human growth hormone, one chorionic gonadotropin carboxy terminal peptide (CTP) attached to the amino terminus of said non-human growth hormone, and two chorionic gonadotropin CTPs attached to the carboxy terminus of said non-human growth hormone, and wherein said polypeptide optionally consists of a signal peptide attached to the amino terminus of said one CTP, thereby inducing growth or weight gain in a non-human subject.

In one embodiment, increasing IGF-1 levels in a human subject may be effective in treating, preventing or suppressing type 1 diabetes, type 2 diabetes, amyotrophic lateral sclerosis (ALS aka "Lou Gehrig's Disease"), severe burn injury and myotonic muscular dystrophy (MMD).

In another embodiment, a GH modified by CTPs is administered to a subject once a day. In another embodiment, a polypeptide comprising a GH modified by CTPs is administered to a subject once every two days. In another embodiment, a GH modified by CTPs is administered to a subject once every three days. In another embodiment, a GH modified by CTPs is administered to a subject once every four days. In another embodiment, a GH modified by CTPs is administered to a subject once every five days. In another embodiment, a GH modified by CTPs is administered to a subject once every six days. In another embodiment, a GH modified by CTPs is administered to a subject once every week. In another embodiment, a GH modified by CTPs is administered to a subject once every 7-14 days. In another embodiment, a GH modified by CTPs is administered to a subject once every 10-20 days. In another embodiment, a GH modified by CTPs is administered to a subject once every 5-15 days. In another embodiment, a GH modified by CTPs is administered to a subject once every 15-30 days.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the growth hormone dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcysteine, sodium metabisulfite and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, a syringe, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, the preparation of the present invention is formulated in liquid formulations for injection via a syringe or Pen device. In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

In one embodiment, the formulations provided herein also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcysteine, sodium metabisulfite and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the formulations further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The formulations provided herein also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of an effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition or formulation to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a GH modified by CTPs is administered via systemic administration. In another embodiment, a growth hormone as described herein is administered by intravenous, intramuscular or subcutaneous injection. In another embodiment, a GH modified by CTPs is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized GH modified by CTPs as described in sterile water for injection. In another embodiment, a pharmaceutical composition comprises a lyophilized growth hormone as described in sterile PBS for injection. In another embodiment, a pharmaceutical composition comprises a lyophilized growth hormone as described in sterile 0.9% NaCl for injection.

In another embodiment, the pharmaceutical composition comprising a GH modified by CTPs as described herein is further formulated to comprise complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a growth hormone as described herein and is further formulated to comprise lactobionic acid and an acetate/glycine buffer. In another embodiment, the pharmaceutical composition comprising a GH modified by CTPs as described herein is further formulated to comprise amino acids, such as arginine or glutamate that increase the solubility of interferon compositions in water. In another embodiment, the pharmaceutical composition comprises a lyophilized GH modified by CTPs as described herein and is further formulated to comprise glycine or human serum albumin (HSA), a buffer (e g. acetate) and an isotonic agent (e.g NaCl). In another embodiment, the pharmaceutical composition comprises a lyophilized GH modified by CTPs as described herein and is further formulated to comprise a phosphate buffer, glycine and HSA.

In another embodiment, the pharmaceutical composition comprising a GH modified by CTPs as described herein is stabilized when placed in buffered solutions having a pH between about 4 and 7.2. In another embodiment, the pharmaceutical composition comprising a GH modified by CTPs as described herein is stabilized when placed in buffered solutions having a pH between about 6 and 6.4. In another embodiment, the pharmaceutical composition comprising a GH modified by CTPs as described herein is stabilized when placed in buffered solutions having a pH of 6.0. In another embodiment, the pharmaceutical composition comprising a GH modified by CTPs as described herein is stabilized when placed in buffered solutions having a pH of 6.2. In another embodiment, the pharmaceutical composition comprising a GH modified by CTPs as described herein is stabilized when placed in buffered solutions having a pH of 6.4. In another embodiment, the pharmaceutical composition comprising a GH modified by CTPs as described herein is stabilized with an amino acid as a stabilizing agent and in some cases a salt (if the amino acid does not contain a charged side chain). In one embodiment, the pharmaceutical composition is stabilized at room temperature. In another embodiment, the pharmaceutical composition is stabilized at 4° C. In another embodiment, the pharmaceutical composition is stabilized at 5° C. In another embodiment, the pharmaceutical composition is stabilized at −20° C. In one embodiment, the pharmaceutical composition is stabilized for at least three months. In one embodiment, the pharmaceutical composition is stabilized for at least six months. In one embodiment, the pharmaceutical composition is stabilized for at least one year. In one embodiment, the pharmaceutical composition is stabilized for at least two years.

In another embodiment, the pharmaceutical composition comprising a GH modified by CTPs as described herein is formulated in a liquid composition comprising a stabilizing agent at between about 0.3% and 5% by weight which is an amino acid.

In another embodiment, the pharmaceutical composition comprising a GH modified by CTPs as described herein provides dosing accuracy and product safety. In another embodiment, the pharmaceutical composition comprising a GH modified by CTPs as described herein provides a biologically active, stable liquid formulation for use in injectable applications. In another embodiment, the pharmaceutical composition comprises a non-lyophilized GH modified by CTPs as described herein.

In another embodiment, the pharmaceutical composition comprising a GH modified by CTPs as described herein provides a liquid formulation permitting storage for a long period of time in a liquid state facilitating storage and shipping prior to administration.

In another embodiment, the pharmaceutical composition comprising a GH modified by CTPs as described herein comprises solid lipids as matrix material. In another embodiment, the injectable pharmaceutical composition comprising a GH modified by CTPs as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e. g. glycerides composed of fatty acids which are present in the emulsions for parenteral nutrition).

In another embodiment, the pharmaceutical composition comprising a GH modified by CTPs as described herein is in the form of liposomes (J. E. Diederichs and al., Pharm./nd. 56 (1994) 267-275).

In another embodiment, the pharmaceutical composition comprising a GH modified by CTPs as described herein comprises polymeric microparticles. In another embodiment, the injectable pharmaceutical composition comprising a GH modified by CTPs as described herein comprises polymeric microparticles. In another embodiment, the pharmaceutical composition comprising a GH modified by CTPs as described herein comprises nanoparticles. In another embodiment, the pharmaceutical composition comprising a GH modified by CTPs as described herein comprises liposomes. In another embodiment, the pharmaceutical composition comprising a GH modified by CTPs as described herein comprises lipid emulsion. In another embodiment, the pharmaceutical composition comprising a GH modified by CTPs as described herein comprises microspheres. In another embodiment, the pharmaceutical composition comprising a GH modified by CTPs as described herein comprises lipid nanoparticles. In another embodiment, the pharmaceutical composition comprising a GH modified by CTPs as described herein comprises lipid nanoparticles comprising amphiphilic lipids. In another embodiment, the pharmaceutical composition comprising a GH modified by CTPs as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the GH modified by CTPs of the present invention can be provided to the individual with additional active agents to achieve an improved therapeutic effect as compared to treatment with each agent by itself. In another embodiment, measures (e.g., dosing and selection of the complementary agent) are taken to minimize adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference. Other general references are provided throughout this document.

Example 1

Generation of hGH constructs

Materials and Methods

Four hGH clones (variants of 20 kD protein) were synthesized. XbaI-NotI fragments containing hGH sequences from the four variants were ligated into the eukaryotic expression vector pCI-dhfr previously digested with XbaI-NotI. DNA from the 4 clones (401-0, 1, 2, 3 and 4) was prepared. Another partial hGH clone (1-242 bp) from 22 kD protein was also synthesized (0606114). Primers were ordered from Sigma-Genosys. The primer sequences used to generate the hGH-CTP polypeptides of the present invention are summarized in Table 1 hereinbelow.

TABLE 1

| Primer number | SEQ ID NO | sequence | Restriction site (underlined in sequence) |
|---|---|---|---|
| 25 | 27 | 5' CTCTAGAGGACATGGCCAC 3' | XbaI |
| 32$^R$ | 28 | 5' ACAGGGAGGTCTGGGGGTTCTG CA 3' | |
| 33 | 29 | 5' TGCAGAACCCCCAGACCTCCCTG TGC 3' | |
| 4$^R$ | 30 | 5' CCAAACTCATCAATGTATCTT A 3' | |
| 25 | 31 | 5' CTCTAGAGGACATGGCCAC 3' | XbaI |
| 35$^R$ | 32 | 5' CGAACTCCTGGTAGGTGTCAAAG GC 3' | |
| 34 | 33 | 5' GCCTTTGACACCTACCAGGAGTT CG 3' | |

TABLE 1 -continued

| Primer number | SEQ ID NO | sequence | Restriction site (underlined in sequence) |
|---|---|---|---|
| 37$^R$ | 34 | 5'ACGCGGCCGCATCCAGACCTTCAT CACTGAGGC 3' | NotI |
| 39$^R$ | 35 | 5'GCGGCCGCGGACTCATCAGAAGCC GCAGCTGCCC 3' | |

Construction of 402-0-p69-1

(hGH) SEQ ID NO: 36: MOD-4020 is the wild type recombinant human growth hormone (without CTP) which was prepared for use as control in the below described experiments.

Three PCR reactions were performed. The first reaction was conducted with primer 25 and primer 32$^R$ and plasmid DNA of 0606114 (partial clone of hGH 1-242 bp) as a template; as a result of the PCR amplification, a 245 bp product was formed.

The second reaction was conducted with primer 33 and primer 4$^R$ and plasmid DNA of 401-0-p57-2 as a template; as a result of the PCR amplification, a 542 bp product was formed.

The last reaction was conducted with primers 25 and 4$^R$ and a mixture of the products of the previous two reactions as a template; as a result of the PCR amplification, a 705 bp product was formed and ligated into the TA cloning vector (Invitrogen, catalog K2000-01). The XbaI-NotI fragment containing hGH-0 sequence was ligated into the eukaryotic expression vector pCI-dhfr. The vector was transfected into DG-44 CHO cells. Cells were grown in protein-free medium.

Construction of 402-1-p83-5 (hGH-CTP) -

SEQ ID NO: 37 and 402-2-p72-3(hGH-

CTPx2) – SEQ ID NO: 38: MOD-4021 is a recombinant human growth hormone which was fused to 1 copy of the C-terminal peptide of the beta chain of human Chorionic Gonadotropin (CTP). The CTP cassette of MOD-4021 was attached to the C-terminus (one cassette). MOD-4022 is a recombinant human growth hormone which was fused to 2 copies of the C-terminal peptide of the beta chain of human Chorionic Gonadotropin (CTP). The two CTP cassettes of MOD-4022 were attached to the C-terminus (two cassettes).

Construction of hGH-CTP and hGH-CTP-CTP was performed in the same way as the construction of hGH-0. pCI-dhfr-401-1-p20-1 (hGH*-ctp) and pCI-dhfr-401-2-p21-2 (hGH*-ctp x2) were used as templates in the second PCR reaction.

MOD-4021 and MOD-4022 were expressed in DG-44 CHO cells. Cells were grown in protein-free medium. The molecular weight of MOD-4021 is ~30.5 Kd since hGH has a MW of 22 Kd while each "CTP cassette" contributes 8.5 Kd to the overall molecular weight (see FIG. 1). The molecular weight of MOD-4022 is ~39 Kd (see FIG. 1).

Construction of 402-3-p81-4 (CTP-hGH-CTP-CTP)- SEQ ID NO: 39 and 402-4-p82 9(CTP*hGH-CTP-CTP)-SEQ ID NO: 40: MOD-4023 is a recombinant human growth hormone which was fused to 3 copies of the C-terminal peptide of the beta chain of human Chorionic Gonadotropin (CTP). The three CTP cassettes of MOD-4023 were attached to both N-terminus (one cassette) and the C-terminus (two cassettes). MOD-4024 is a recombinant human growth hormone which is fused to 1 truncated and 2 complete copies of the C-terminal peptide of the beta chain of human Chorionic Gonadotropin (CTP). The truncated CTP cassette of MOD-4024 was attached to the N-terminus and two CTP cassettes were attached to the C-terminus (two cassettes).

Figure 3:
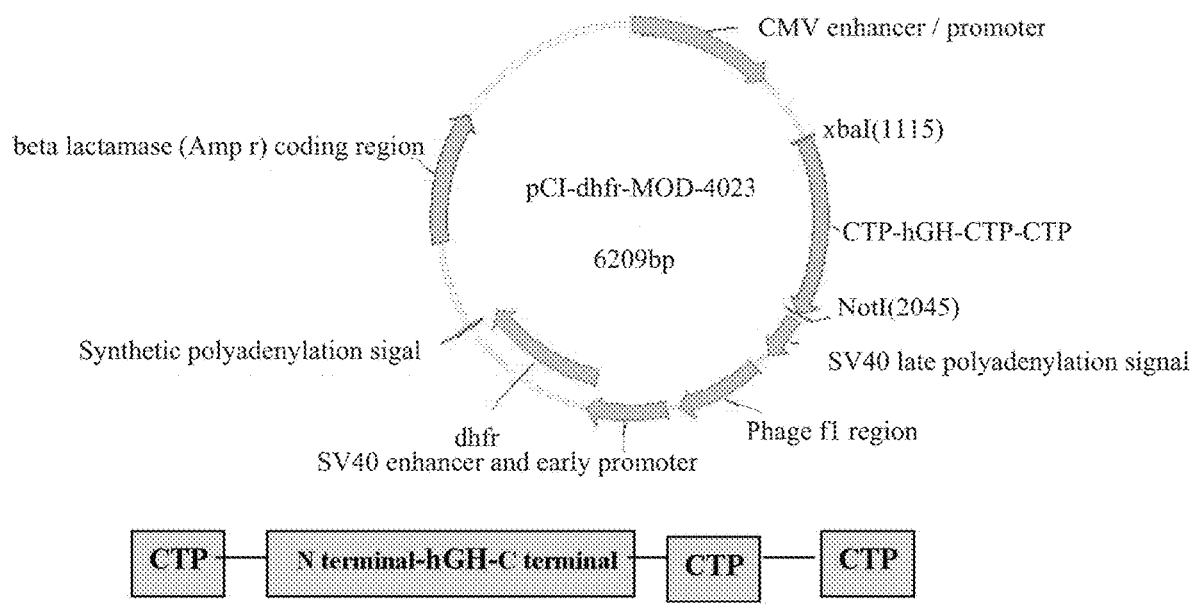
FIG. 3 includes two schemes (1) a map of CTP-hGH-CTP-CTP pCI-dhfr Plasmid and (2) structural protein formula of CTP-hGH-CTP-CTP.

Three PCR reactions were performed. The first reaction was conducted with primer 25 and primer $35^R$ and plasmid DNA of p401-3-p12-5 or 401-4-p22-1 as a template; as a result of the PCR amplification, a 265 or 220 bp product was formed. The second reaction was conducted with primer 34 and primer $37^R$ and plasmid DNA of TA-hGH-2-q65-1 as a template; as a result of the PCR amplification, a 695 bp product was formed. The last reaction was conducted with primers 25 and $37^R$ and a mixture of the products of the previous two reactions as a template; as a result of the PCR amplification, a 938 or 891 bp product was formed and ligated into TA cloning vector (Invitrogen, catalog K2000-01). XbaI-NotI fragment containing hGH sequence was ligated into our eukaryotic expression vector pCI-dhfr. (FIG. 3)

MOD-4023 and MOD-4024 were expressed in DG-44 CHO cells. Cells were grown in protein-free medium. The molecular weight of MOD-4023 is ~47.5 Kd (see FIG. 1) and the molecular weight of MOD-4024 is ~43.25 Kd (FIG. 1).

Construction of 402-6-p95a-8

(CTP-hGH-CTP-SEQ ID NO: 41: Construction of hGH-6 was performed in the same way as the construction of hGH-3. pCI-dhfr-402-1-p83-5 (hGH-ctp) was used as a template in the second PCR reaction.

Construction of 402-5-p96-4

(CTP-hGH)-SEQ ID NO: 42: PCR reaction was performed using primer 25 and primer $39^R$ and plasmid DNA of pCI-dhfr-ctp-EPO-ctp (402-6-p95a-8) as a template; as a result of the PCR amplification, a 763 bp product was formed and ligated into TA cloning vector (Invitrogen, catalog K2000-01). XbaI-NotI fragment containing ctp-hGH sequence was ligated into our eukaryotic expression vector pCI-dhfr to yield 402-5-p96-4 clone.

Example 2

In vivo bioactivity tests of hGH-CTP polypeptides of the present invention

The following experiment was performed in order to test the potential long acting biological activity of hGH-CTP polypeptides in comparison with commercial recombinant human GH and MOD-4020.

Materials and Methods

Female hypophysectomized rats (60-100 g) received a weekly S.C. injection of 21.7 μg hGH-CTP polypeptides or a once daily 5 μg S.C. injection of control commercial rhGH.

Weight was measured in all animals before treatment, 24 hours following first injection and then every other day until the end of the study on day 21. Each point represents the group's average weight gain percentage ((Weight day 0−weight last day)/Weight day 0). Average weight gain was normalized against once-daily injection of commercial hGH. The treatment schedule is summarized in Table 2.

TABLE 2

| No. | Drug | N | Route | Treatment Schedule | Equimolar Dose (μg/rat) | Accumulate Dosage (μg/rat) | Dose Vol.(ml) |
|---|---|---|---|---|---|---|---|
| 1 | Vehicle | 7 | s.c. | days 1, 7 and 13; 1/W | NA | NA | 0.25 |
| 2 | Mock | 7 | s.c | days 1, 7 and 13; 1/W | NA | NA | 0.25 |
| 3 | MOD-4020 SEQ ID NO: 36 | 7 | s.c | days 1, 7 and 13; 1/W | 21.7 | 65 | 0.25 |
| 4 | MOD-4021 SEQ ID NO: 37 | 7 | s.c. | days 1, 7 and 13; 1/W | 21.7 | 65 | 0.25 |
| 5 | MOD-4022 SEQ ID NO: 38 | 7 | s.c. | days 1, 7 and 13; 1/W | 21.7 | 65 | 0.25 |
| 6 | MOD-4023 SEQ ID NO: 39 | 7 | s.c. | days 1, 7 and 13; 1/W | 21.7 | 65 | 0.25 |
| 7 | MOD-4024 SEQ ID NO: 40 | 7 | s.c. | days 1, 7 and 13; 1/W | 21.7 | 65 | 0.25 |
| 8 | Commercial hGH v.1 | 7 | s.c. | days 1, 7 and 13; 1/W | 21.7 | 65 | 0.25 |
| 9 | Commercial hGH v.1 | 7 | s.c. | days 1-13; d/W | 5 | 65 | 0.25 |

Results

Figure 2:
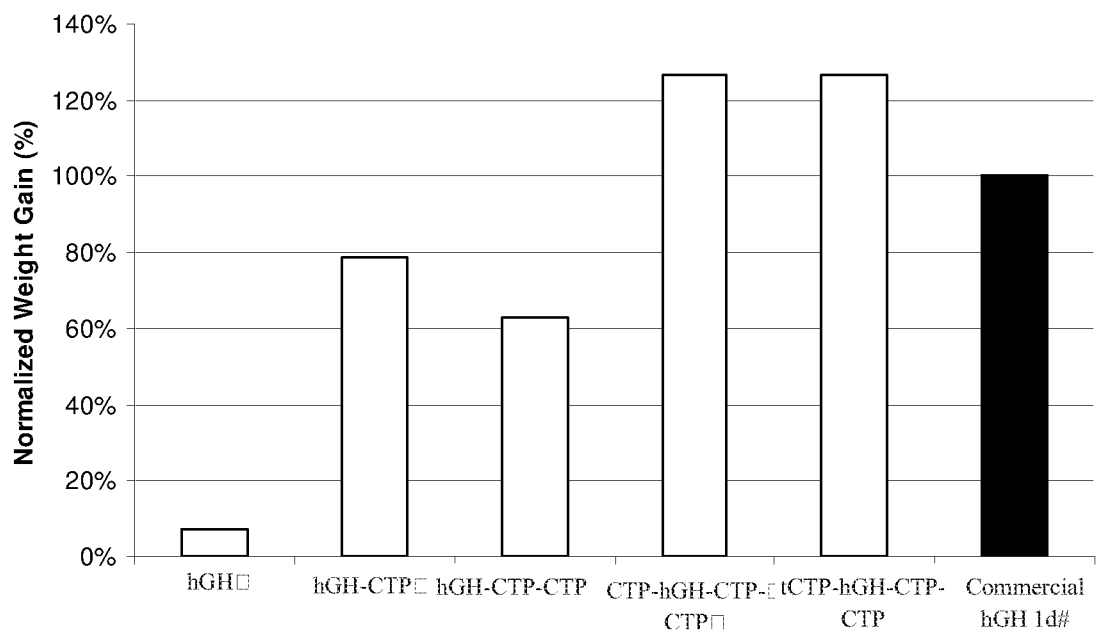
FIG. 2 is a bar graph illustrating the weight gain of hypophysectomized rats following administration of the GH-CTP polypeptides of the present invention.

Results are summarized in FIG. 2. These results show that MOD-4023 (SEQ ID NO: 39) and MOD-4024 (SEQ ID NO: 40) induced over 120% weight gain compared to commercial rhGH which induced 100% weight gain.

Conclusion

Three weekly doses (Days of injections; 1, 7, and 13) of 21.7 μg of MOD-4023 (SEQ ID NO: 39) and MOD-4024 (SEQ ID NO: 40) induced a 30% greater weight increase in hypophysectomised rats compared to commercial rhGH injected at the same accumulated dose which was administered once per day at a dose of 5 μg for 13 days.

Example 3

Pharmacokinetic studies of CTP-modified GH

Single-dose pharmacokinetic studies were conducted in Sprague-Dawley rats. All animal experimentation was conducted in accordance with the Animal Welfare Act, the Guide for the Care and Use of Laboratory Animals, and under the supervision and approval of the Institutional Animal Care and Use Committees of Modigene, Biotechnology General Ltd. Rats were housed either individually or two per cage in rooms with a 12-h light/dark cycle. Access to water (municipal supply) and noncertified rodent chow was provided ad libitum.

Figure 4:
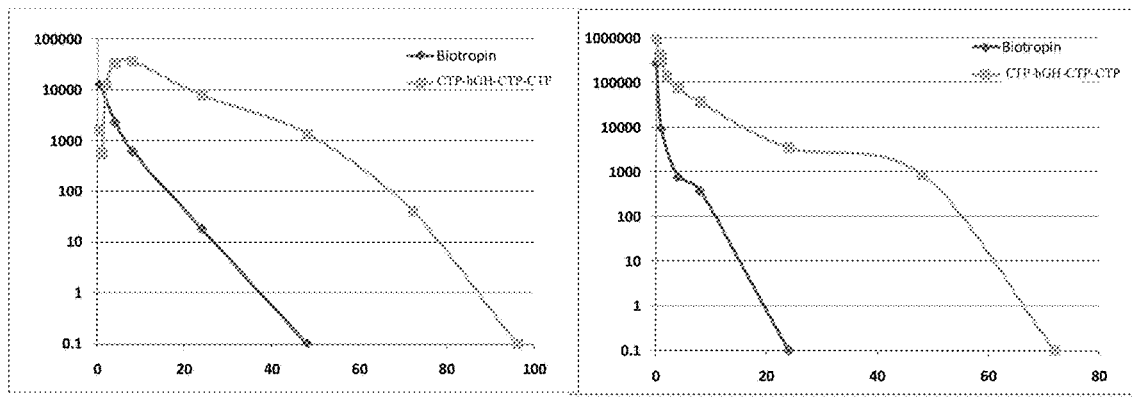
FIG. 4 are graphs showing the mean plasma CTP-hGH-CTP-CTP or GH concentrations (pg/ml) following a single i.v. or s.c. dose of CTP-hGH-CTP-CTP or GH in rats (n=3-6 per dose/route).

To compare the pharmacokinetics of CTP-hGH-CTP-CTP and GH in rats, four groups of Sprague-Dawley rats (270-290 g), three to six male rats per group. The rats were randomly assigned to four treatment groups (see Table 3). Rats were administered a single s.c. or i.v. injection of GH (50 µg/kg i.v. or s.c.) or CTP-hGH-CTP-CTP (108 µg/kg i.v. or s.c.). With the exception of the predose sample, which was collected under isoflurane anesthesia, blood collection was performed in unanesthetized animals. Blood samples (approximately 0.25 ml) were collected in EDTA-coated microtainers for ELISA analyses of CTP-hGH-CTP-CTP plasma concentration at the times outlined in Table 11. After each sampling, the blood volume was replaced with an equal volume of sterile 0.9% saline. Samples were stored on ice for up to 1 h prior to centrifugation and plasma harvest. Plasma samples were stored at approximately −20° C. prior to analysis.

analyzed individually, and mean±standard error of the mean (S.E.M.) values for the pharmacokinetic parameters are reported in Table 4 and FIG. 4.

CTP-hGH-CTP-CTP is a single chain protein of 275 amino acids and up to twelve O-linked carbohydrates. The structure consists of modified human Growth Hormone (Somatropin) attached to three copies of the C-terminal peptide (CTP) of the beta chain of human Chorionic Gonadotropin (hCG); one copy at the N-terminus and two copies (in tandem) at the C terminus. Human Growth Hormone is comprised of 191 amino acids. CTP is comprised of 28 amino acids and four O-linked sugar chains.

Example 4

*Pharmacokinetics of CTP -modified GH in SD rats*

The pharmacokinetics of CTP-hGH-CTP-CTP was evaluated and compared to that of commercial hGH (Biotropin).

TABLE 3

Experimental design of rat pharmacokinetic study

| Trt. Grp. | Test Article | No. of animals/ group/ timepoint | Dose Route | Gender | Dose Level (µg/kg) | Injected Vol. (µl) | Concentration (µg/ml)/Total vol. (ml) | Time-Points * (hours post-dose) |
|---|---|---|---|---|---|---|---|---|
| 1 | Biotropin | 6# | SC | Male | 50 | 500 | 20/5 | 0 (Pre-dose) 0.5, 2, 4, 8, 24, 48 |
| 2 | CTP-hGH-CTP-CTP | 6# | SC | Male | 108 | 500 | 43.2/5 | 0.5, 2, 4, 8, 24, 48, 72, 96 |
| 3 | Biotropin | 6# | IV | Male | 50 | 300 | 20/3 | 0, 0.12, 2, 4, 8, 24 |
| 4 | CTP-hGH-CTP-CTP | 6# | IV | Male | 108 | 300 | 43.2/3 | 0.12, 2, 4, 8, 24, 48, 72 |
| | | Volume of blood sample/time point-500 µl | | | | | | Terminal blood samples |

3 rats per time point

A commercial sandwich ELISA kit specific for detection of human growth hormone (Roche Diagnostics) was used for evaluation of the rat plasma samples. This kit detects human growth hormone in plasma by means of an antibody sandwich ELISA format. This kit was initially used to measure the concentration of CTP-hGH-CTP-CTP in rat plasma. For these plasma samples, a CTP-hGH-CTP-CTP standard curve (1.2-100 ng/ml) was used and the concentrations of CTP-hGH-CTP-CTP in rat plasma were interpolated from this curve.

Standard pharmacokinetic parameters, including clearance (CL or CL/F), volume of distribution (Vd or Vd/F), half-life ($t_{1/2}$), area under the plasma concentration versus time curve (AUC), maximal observed plasma concentration ($C_{max}$) and time to maximal observed plasma concentration ($T_{max}$), were obtained from plasma albutropin or GH concentration/time curves by noncompartmental analysis using the modeling program WinNonlin (Pharsight, version 3.1). Plasma CTP-hGH-CTP-CTP or GH concentration data were uniformly weighted for this analysis. The AUC was calculated using the log-linear trapezoidal analysis for the i.v. data and the linear-up/log-down trapezoidal method for the s.c. data. Plasma concentration profiles for each rat (with the exception of the s.c. albutropin data) or monkey were

TABLE 4

Mean pharmacokinetic parameters following single-dose i.v. and s.c. administration of CTP-hGH-CTP-CTP and GH (Biotropin) in Sprague-Dawley rats.

| | | SC | | IV | |
|---|---|---|---|---|---|
| PK Statistics | | | CTP-hGH-CTP- | | CTP-hGH-CTP- |
| Parameters | Units | Biotropin | CTP | Biotropin | CTP |
| Dose | mg/Kg | 50 | 50 | 50 | 50 |
| AUClast | hr * ng/mL | 41 | 680 | 162.7 | 1568.3 |
| Cmax | ng/ml | 13 | 36.8 | 275.8 | 926 |
| Tmax | hr | 0.5 | 8 | 0 | 0 |
| MRT | hr | 2.5 | 12.9 | 0.5 | 9.9 |
| T½ alpha | hr | | 1.58 | | 0.74 |
| T½ beta | hr | 1.73 | 9 | 0.5 | 6.9 |

Data Statistical Analysis

Analysis of serum samples was performed in order to determine specific concentration levels for each sample. Concentration and time-point data were processed using WinNonLin noncompartmental analysis.

Parameters that were determined included: AUC, MRT, t1/2, Cmax, and Tmax. FIG. 4 demonstrates the superior pharmacokinetic profile of CTP-hGH-CTP-CTP plasma concentration compared to GH concentrations (pg/ml) following a single i.v. or s.c. dose of CTP-hGH-CTP-CTP or GH in rats (n=3-6 per route).

Following a single S.C. injection of 50 μg/kg, clearance of CTP-hGH-CTP-CTP from SD rat's blood was significantly slower than that of CTP-hGH-CTP and of Biotropin. The corresponding calculated half-life times and AUCs were:

| Biotropin | T½ 1.7 h, AUC 41 hr * ng/mL |
| CTP-hGH-CTP | T½ 8.5 h, AUC 424 hr * ng/mL |
| CTP-hGH-CTP-CTP | T½ 9.0 h, AUC 680 hr * ng/mL |

Conclusion: CTP-hGH-CTP-CTP was chosen as the final candidate out of 6 other variants. CTP-hGH-CTP-CTP demonstrated superior performance in terms of biological activity and pharmacokinetics.

Example 5

Weight Gain Assay (WGA) for Single dose/Repeated dose of CTP-modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized were 70-90 grams, at the time of the experiment. This is the standard USP and EP bioassay for hGH. Hypophysectomized rats (rats from which the pituitary gland was removed) lose their ability to gain weight. Injections of hGH (and of CTP-hGH-CTP-CTP) to these rats result in weight gain. Based on the measured weight gain along a defined period of time and the amount of hGH injected, the specific activity of hGH (and CTP-hGH-CTP-CTP) is determined. Rats were administered either a single s.c. doses of 0.4, 0.8 and 4 mg/Kg or repeated s.c. doses of 0.6 and 1.8 mg/Kg 4 days apart for 3 weeks. Individual body weights of all animals are determined at randomization, prior to the first dosing, thereafter every two days or in case of decedents at the time of death, and prior to sacrifice.

Single Dose and Repeated Dose Weight Gain Assay

Figure 5:
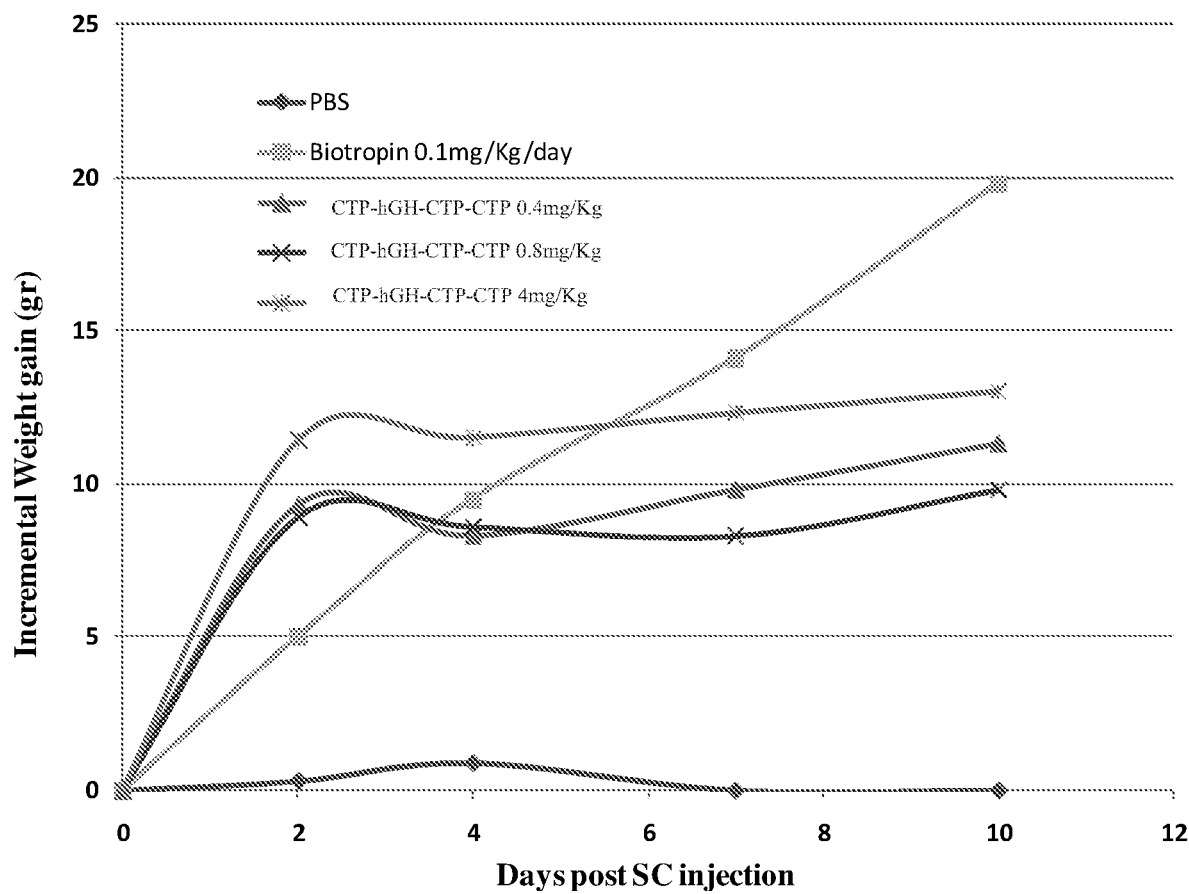
FIG. 5 are graphs showing the mean incremental weight gain following a single s.c. doses of CTP-hGH-CTP-CTP (0.4, 0.8 and 4 mg/Kg) in hypophysectomized rats in comparison to daily GH injections (0.1 mg/Kg/Day) (n=10 per dose).

The results comparing whole body growth response following different dosing patterns of CTP-hGH-CTP-CTP in hypophysectomized rats are demonstrated in FIG. 5. The results demonstrate that a single injection of 0.4 & 0.8 mg/Kg/day doses of hGH-CTP were equivalent to 4 daily injections of 0.1 mg/Kg/day of Biotropin. The peak of the hGH-CTP effect was after 2 days.

Figure 6:
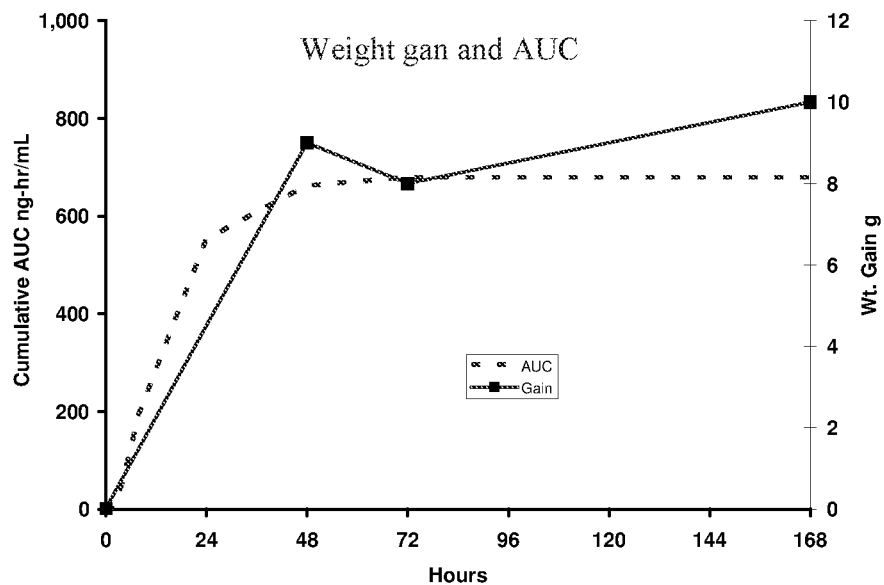
FIG. 6 is a graph showing the area Under the Curve following single injection of CTP-hGH-CTP-CTP correlates with Body Weight gain in Rats.

FIG. 6 further demonstrates that the area under the curve following single injection of CTP-hGH-CTP-CTP correlates with Body Weight gain in Rats. Thus, the collective data demonstrates that body weight gain is closely correlated with cumulative AUC.

Figure 7:
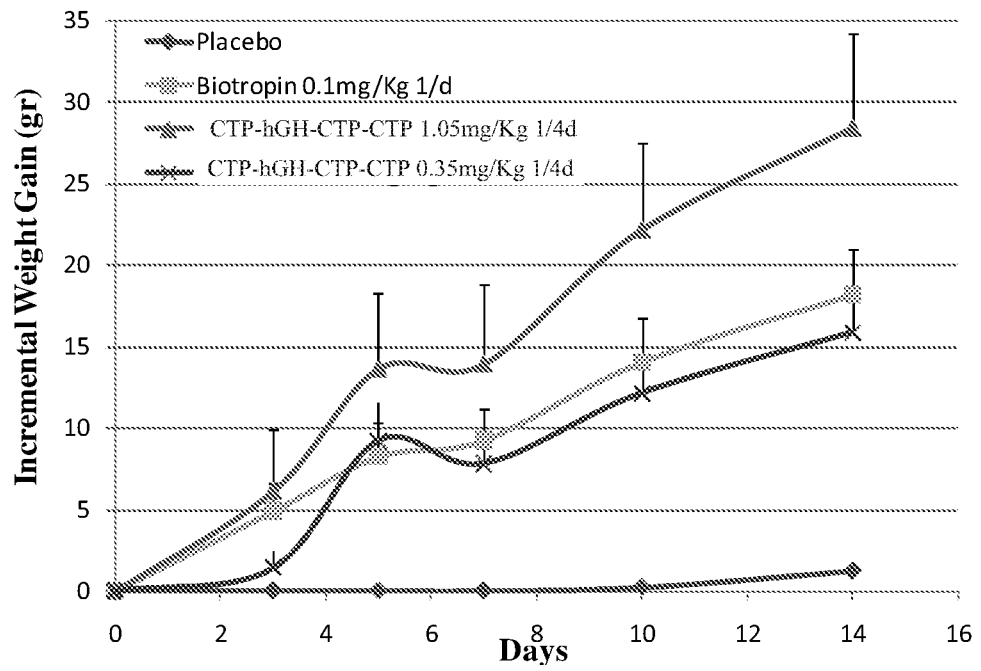
FIG. 7 is a graph showing the incremental weight gain following an s.c. doses of CTP-hGH-CTP-CTP (0.4, 0.8 and 4 mg/Kg) 4 days apart in hypophysectomized rats in comparison to daily GH injections (0.1 mg/Kg/Day) (n=10 per dose).

The hGH-CTP construct administered 4 days apart promotes the same weight gain as daily injections of Biotropin as demonstrated in FIG. 7. Half-life of hGH in humans is expected to be 5× better than in rats—indicating potential peak effect in humans after 10 days for one single injection. These results support administration of hGH-CTP construct, CTP-hGH-CTP-CTP, once weekly or bi-weekly in humans.

Example 6

Pharmacodynamics/Pharmacokinetics studies of CTP-modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized and sham rats were 70 and 150 g, respectively, at the time of the experiment.

Rats were administered a single s.c. with CTP-hGH-CTP-CTP, vehicle, human growth hormone CTP-hGH-CTP-CTP or human growth hormone (20 μg/rat) was administered s.c. in an injection volume of 0.2 ml/rat. The dose of GH was 0.35 and 1.05 μg/Kg, a dose of growth hormone that was equimolar with the amount of GH in a corresponding 0.6 and 1.8 μg/Kg dose of CTP-hGH-CTP-CTP. The treatment groups are summarized in Table 5. Following injection, plasma samples for IGF-1 analyses were obtained at the times described in Table 5. Samples were analyzed for IGF-1 concentration using a commercial ELISA (R&D systems).

TABLE 5

Treatment schedule for hypophysectomized rat study

| Trt. Grp. | Test Article | No. of animals/ group/ timepoint | Dose Route | Eq. Dose (mg/rat) | Eq. Dosage (mg/Kg) | CTP-hGH-CTP-CTP Conc. mg/ml | Dose Vol. (ml) | Time-Points * (hours post-dose) |
| --- | --- | --- | --- | --- | --- | --- | --- | --- |
| M7 | Biotropin | 9 | SC | 0.032 | 0.35 | 0.16 | 0.2 | 0 (Pre-dose) 0.5, 2, 4, 8, 24, 48, 72, 96 |
| M8 | Biotropin | 9 | SC | 0.095 | 1.05 | 0.475 | 0.2 | 0 (Pre-dose) 0.5, 2, 4, 8, 24, 48, 72, 96 |
| M9 | EN648-01-08-005 | 12 | SC | 0.032 (0.055) | 0.35 (0.6) | 0.275 | 0.2 | 1, 2, 4, 8, 24, 48, 72, 96 |

TABLE 5-continued

Treatment schedule for hypophysectomized rat study

| Trt. Grp. | Test Article | No. of animals/ group/ timepoint | Dose Route | Eq. Dose (mg/rat) | Eq. Dosage (mg/Kg) | CTP-hGH-CTP-CTP Conc. mg/ml | Dose Vol. (ml) | Time-Points * (hours post-dose) |
|---|---|---|---|---|---|---|---|---|
| M10 | EN648-01-08-005 | 12 | SC | 0.095 (0.165) | 1.05 (1.8) | 0.825 | 0.2 | 1, 2, 4, 8, 24, 48, 72, 96 Terminal blood samples |
| | | Volume of blood sample/time point-500 µl | | | | | | |

Non-compartmental pharmacokinetic analysis was performed on the mean serum concentration versus time curves for each group. CTP-hGH-CTP-CTP Cmax was significantly higher than Biotropin Cmax. The terminal half-live of CTP-hGH-CTP-CTP was 6 times higher than Biotropin.

TABLE 6

Pharmacokinetic Parameter Estimates of CTP-hGH-CTP-CTP and Biotropin Following a Single Subcutaneous Injection in hypophysectomized Rats

| Group | Dose mg/kg | Gender | Cmax ng/mL | Tmax hr | $AUC_{0-\infty}$ ng-hr/mL | $AUC_{0-t}$ ng-hr/mL | CL/F mL/hr/kg | $T_{1/2}$ hr |
|---|---|---|---|---|---|---|---|---|
| CTP-hGH-CTP-CTP | 1.8 | M | 2,150 | 8 | 37,713 | 37,695 | 0.928 | 6.86 |
| | 0.6 | M | 681 | 8 | 11,505 | 11,489 | 3.042 | 6.8 |
| hGH | 1.05 | M | 1,078 | 0.5 | 3,541 | 3,540 | 9.884 | 1 |
| | 0.35 | M | 439 | 0.5 | 1,279 | 1,279 | 27.36 | 1 |

Figure 8:
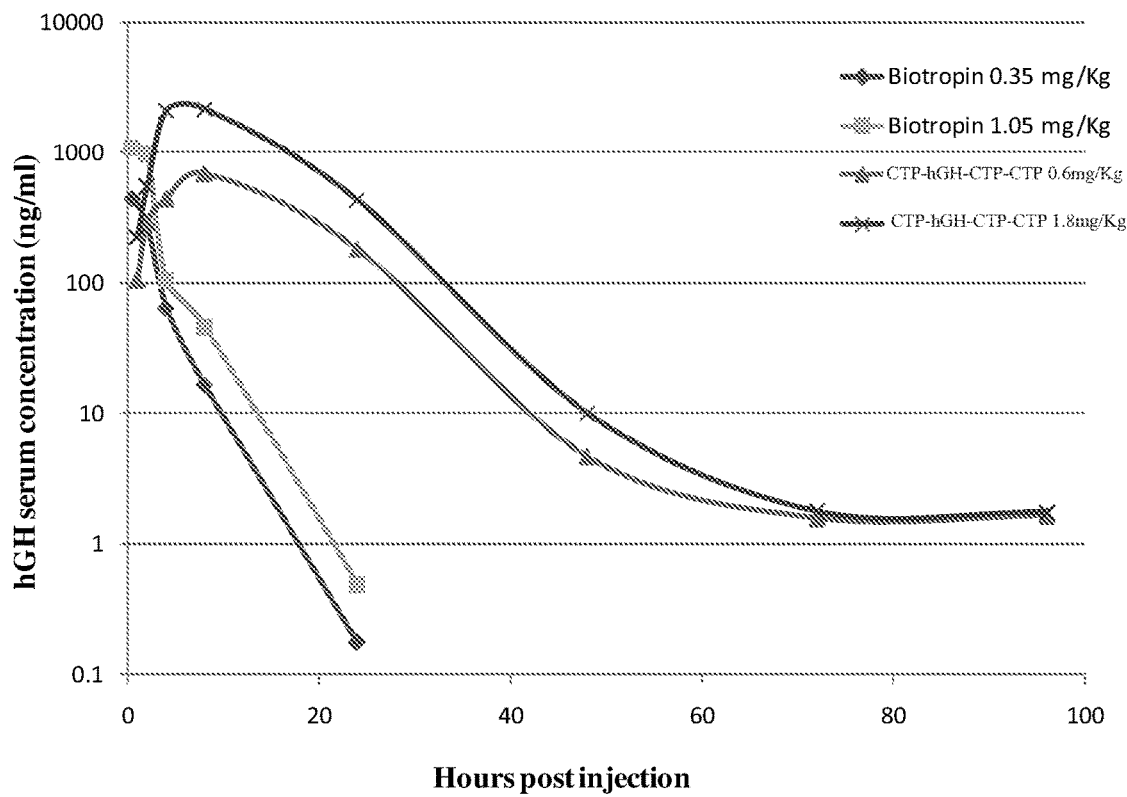
FIG. 8 is a graph showing hGH serum concentration in hypophysectomized rat following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomized rats for determination of PK/PD profile. Serum hGH post injection was measured using specific ELISA kits.

The $AUC_{0-t}$ and the $AUC_{0-\infty}$ were very similar suggesting the duration of sampling was adequate to characterize the pharmacokinetic profiles. AUC of CTP-hGH-CTP-CTP was 10 times higher than of Biotropin. Moreover, Cmax was generally proportional to dose and for CTP-hGH-CTP-CTP and it was twice higher than Cmax of Biotropin. However, as shown in FIG. 8, Tmax of CTP-hGH-CTP-CTP was 8 hr as compare to 0.5 hr of Biotropin, and the terminal half-lives did not appear to vary with dose level. T1/2 of CTP-hGH-CTP-CTP was 6.8 times longer than of Biotropin.

Figure 9:
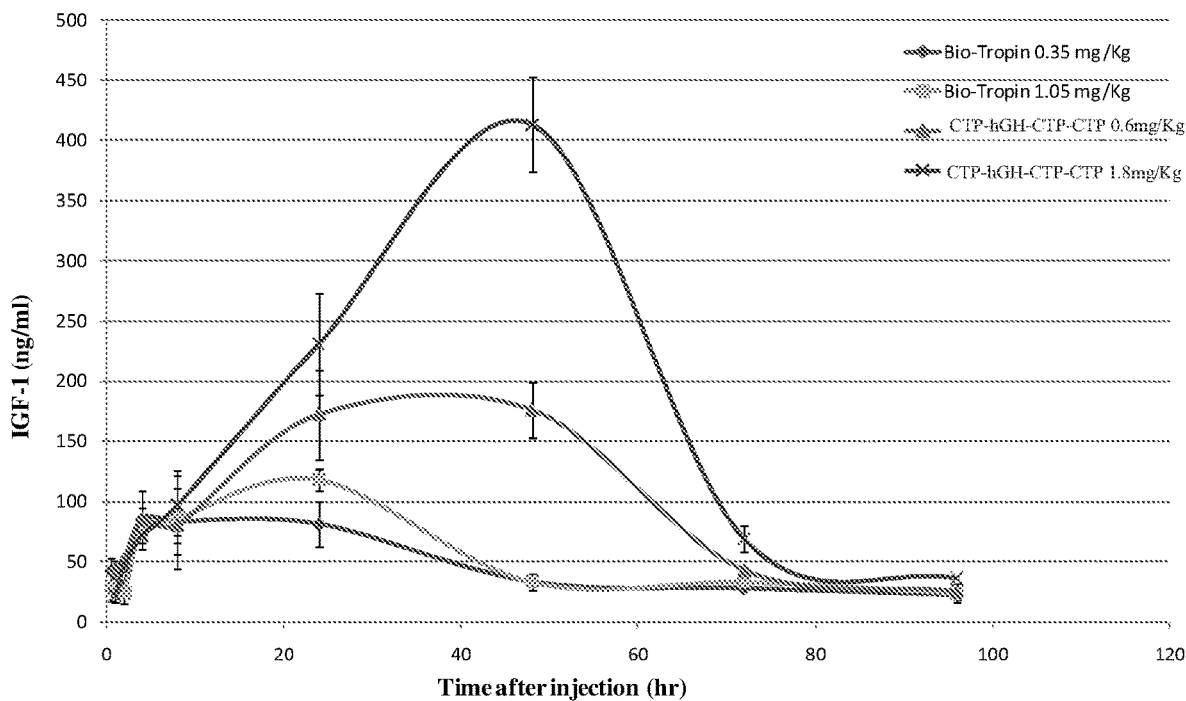
FIG. 9 is a graph showing IGF-1 serum levels in hypophysectomized rats following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomized rats for determination of PK/PD profile. Serum IGF-1 post injection was measured using specific ELISA kits (Roche Diagnostics).

Indirect effects of GH are mediated primarily by an insulin-like growth factor-I (IGF-1), a hormone that is secreted from the liver and other tissues in response to growth hormone. A majority of the growth promoting effects of growth hormone is actually due to IGF-1 acting on its target cells. Accordingly, the effect of the CTP-hGH construct, CTP-hGH-CTP-CTP, on IGF-1 serum levels in Hypophysectomized Rats was measured. FIG. 9 presents results of IGF-1 serum levels in Hypophysectomized Rats Following SC injection of CTP-hGH-CTP-CTP and commercial hGH.

Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum IGF-1 post injection was measured using specific ELISA kits (Roche Diagnostics).

The cumulative serum levels of IGF-1 following injection of CTP-hGH-CTP-CTP was significantly higher than following injection of Biotropin. Cmax was generally proportional to dose and for CTP-hGH-CTP-CTP it was 3-4 times higher than Cmax of Biotropin. Tmax of CTP-hGH-CTP-CTP was 36-48 hr as compare to 20-24 hr of Biotropin. In conclusion, higher hGH levels and longer presence in serum result in significant increase in IGF-1 levels.

Example 7

*Carbohydrate Content and Sialic Acid Content of CTP-modified GH*

Analysis of O-glycans is based on a Prozyme kit. O-glycans are chemically and enzymatically cleaved from the protein and separated from peptides using paper chromatography. Sequencing of the O-glycan pool is performed by sequential enzymatic digestions (exo-glycosidases) followed by HPLC analysis compared to standards.
Glycoprofiling with Sequence Analysis
Glycoprofiling was performed by Ludger Ltd. Two samples (EN648 and RS0708) were taken through triplicate releases and each release was also analyzed by HPLC in triplicate. Triplicate 300 µg samples of EN648 and RS0708 and a single 100 µl sample of citrate/sodium chloride buffer, plus a positive control fetuin (250 µg) and a 100 µl water negative control, were ultra-filtrated by centrifugation using a molecular weight cut off membrane of 10,000 Da to replace the buffer with water, then taken through hydrazinolysis under O-mode conditions (6 h at 60° C.). Released glycans were re-N-acetylated and cleaned up by LudgerClean CEX cartridges. An aliquot of the released glycans was then labeled with 2-aminobenzamide (2AB), cleaned up with Ludger Clean S cartridges and analyzed by LudgerSep-N2 HILIC-HPLC.
Monosaccharide Content
Analysis of neutral monosaccharides requires hydrolysis of glycans to their constituent monosaccharide components.

The hydrolysis was performed by Ludger Ltd, on intact glycoprotein samples. Specifically, 50 μg of intact glycoprotein was acid hydrolyzed, 2-AB (2-aminobenzamide) labeled and run on a reverse phase HPLC column. This method hydrolyzes all glycans present on the glycoprotein inclusive of N and O linked types.

Sialic Acid Profiling

Two samples (EN648 and RS0708) and a buffer control were analyzed. Sialic acid analysis requires mild acid release of the monosaccharides followed by DMB fluorophore labeling and HPLC analysis on a LudgerSep-R1 column. 50 μg of intact glycoprotein was acid hydrolyzed for each analysis.

Glyco Analysis of CTP-hGH-CTP-CTP

TABLE 7

Glycan analysis. Structural assignments and percentage areas of peaks are based upon HPLC and enzyme array digests.

| | | | | Percent from total glycans[e] | | | |
|---|---|---|---|---|---|---|---|
| Peak ID[a] | GU[b] | Structure[c] | name | Und[d] | NAN1 | ABS | ABS BTG |
| 1[f] | 0.92 | ◆—2AB + bgd | GalNAc | 0.4 | 0.4 | 0.6 | 53.0 |
| 2[f] | 1.02 | ◇—2AB + bgd | galactose | 1.9 | 9.7 | 23.8 | 26.5 |
| * | 1.72 | | | 4.3 | 4.6 | 2.3 | |
| 3 | 1.79 | ◇◆—2AB | Galβ1-3GalNAc | 2.3 | 67.7 | 69.4 | 17.1[h] |
| 4[g] | 2.25 | ★◇—2AB | NeuNAcα2-3Gal | 19.8 | 13.0[h] | | |
| * | 2.57 | | | 1.5 | 1.9 | 1.1 | 1.1 |
| 5 | 2.90 | ★◇◆—2AB | NeuNAcα2-3Galβ1-3 GalNAc | 70.6 | | | |
| * | 3.58 | | | 0.6 | 0.7 | 0.6 | |
| 6 | 3.22 | ★◇◆—2AB | Galβ1-3[NeuNAcα2-6] GalNAc | 0.9 | 2.3 | | |
| 7 | 4.42 | ★◇◆—2AB | NeuNAcα2-3Galβ1-3 [NeuNAcα2-6]GalNAc | 1.8 | | | |

TABLE 8

Estimates of CTP-hGH-CTP-CTP Pharmacokinetic Parameters (Mean ± SD) from Non-compartmental Analysis Following A Single Subcutaneous Injection in Rhesus Monkeys

| Parameter | 1.8 mg/kg | 90 mg/kg |
|---|---|---|
| Cmax (μg/mL) | 2.073 ± 0.417 | 108.7 ± 46.0 |
| Tmax (hr) | 4 ± 0 | 11 ± 7 |
| $AUC_{0-t}$ (μg-hr/mL) | 38.7 ± 7.4 | 2,444 ± 394 |
| $AUC_{0-\infty}$ (μg-hr/mL) | 39.0 ± 7.3 | 2,472 ± 388 |
| CL/F (mL/hr/kg) | 47.5 ± 9.0 | 37.04 ± 4.78 |
| $T_{1/2}$ (hr) | 10.00 ± 1.47 | 9.85 ± 1.07 |
| Vz/F (mL/kg) | 701 ± 236 | 529 ± 104 |

The monosaccharide profiles indicate that the CTP-hGH-CTP-CTP glycoprotein samples contain predominantly O-link type glycans. The major O-glycan peak is sialylated core 1 (Neu5Acα2-3Galβ1-3GalNAc). The major sialic acid is Neu5Ac and there are some minor peaks suggesting the presence of 3-4% of di-acetylated sialic acid N-acetyl-9-O-acetylneuraminic acid (Neu5, 9Ac2) and less than 1% N-glycolylneuraminic acid. There are also small amounts of Neu5Acα2-6(Galβ1-3)GalNAc.

Example 8

*Pharmacokinetic/Toxicokinetic Analysis of CTP-modified GH in Rhesus monkeys*

Serum concentrations versus time curves were generated for each animal. Non-compartmental analysis was performed with WinNonlin professional version 5.2.1 (Pharsight Corporation, Mt View CA). The estimated pharmacokinetic parameters are shown in Table 8 below:

The $AUC_{0-t}$ and the $AUC_{0-\infty}$ were very similar suggesting the duration of sampling was adequate to characterize the pharmacokinetic profiles. Cmax was proportional to dose. Tmax was later at the higher dose. Tmax was at 4 hours for all animals in the low dose group and was at 8 or 24 hours in the high dose group. Terminal half-lives are similar for the two dose groups.

AUC was approximately proportional to dose with a slightly larger than proportional AUC at the higher dose producing a slightly lower estimate for CL/F and Vz/F compared to the lower dose. It is not possible to say if CL and Vz are lower at the higher dose or if F is lower at the lower dose. There was overlap between the groups so it is questionable that this represents a meaningful difference in CL/F and Vz/F.

Pharmacokinetic parameters estimated by the model were very similar to those from non-compartment analysis. Absorption and elimination half-lives are shown in Table 9 below:

TABLE 9

Estimates of CTP-hGH-CTP-CTP Absorption and Elimination
Half-lives (Mean ± SD) Following Subcutaneous Injection
Derived From Pharmacokinetic Modeling in Rhesus Monkeys

| Dose | $T_{1/2\ abs}$ (hr) | $T_{1/2\ el}$ (hr) |
|---|---|---|
| 1.8 mg/kg | 1.17 ± 0.40 | 10.41 ± 2.36 |
| 90 mg/kg | 6.49 ± 1.87 | 7.26 ± 1.85 |

The data indicate that the elimination rates are fairly similar between the groups with a slightly longer T1/2 el in the lower dose group. The absorption, however, is more than 5-fold slower following subcutaneous administration of 90 mg/kg compared to that following 1.8 mg/kg. As in the case of the non-compartmental analysis, modeling indicated a later Tmax at the high dose.

Although GH supplementation is effective in the treatment of GH deficiency in children and adults, the disadvantages of daily injections over extended periods of time limit its use by physicians in certain patient populations as well as increase the risk of dosing error, the number of care givers, the cost of treatment and/noncompliance. Especially important in certain populations, such as children of short stature who may not understand the implications of not following the prescribed GH dosing regimen, is the necessity of compliance to achieve the optimal benefit from GH therapy. The issue of finding a more suitable alternative to daily GH injections and subsequent compliance gains further importance as GH-deficient children transition into adults with a continuing need for GH treatment. The requirement of daily therapy is largely due to recombinant GH's short plasma half-life and has led to the development of a sustained release form of GH (Reiter E O. Attire K M., Mashing T J. Silverman B L. Kemp S F. Neolith R B. Ford K M. and Sanger P. A multimember study of the efficacy and safety of sustained release GH in the treatment of naive pediatric patients with GH deficiency. J. Clin. Endocrinol. Metab. 86 (2001), pp. 4700-4706.).

GH-CTP, a recombinant human growth hormone-CTP fusion protein, as described herein, has a pharmacokinetic profile in the rat that is longer in duration than that of GH. This unique pharmacokinetic profile allows for intermittent administration of GH-CTP to achieve pharmacodynamic effects in growth-hormone-deficient rat as evidenced by growth and elevations in plasma IGF-1 levels, respectively.

GH-CTP offers a superior pharmacokinetic profile compared with that of GH when administered s.c. in the rat. There are substantial differences in plasma clearance of GH-CTP compared to GH. Specifically, plasma is cleared of GH-CTP at more than 6 times more slowly than GH following s.c. dosing. The terminal half-life and mean residence time of GH-CTP were approximately six times longer than that of GH in rats following s.c. administration. In addition, the Cl/F following s.c. dosing is 10 times lower for GH-CTP than for GH.

In an effort to examine whether the pharmacokinetic advantages in the rat translated to a pharmacodynamic benefit, the possibility that GH-CTP might stimulate growth in GH-deficient hypophysectomized rats with dosing regimens less frequent than daily was tested at equimolar CTP-hGH-CTP-CTP and GH dose levels. Single SC injection of GH-CTP promoted incremental weight gain which was equal to 4 daily consecutive injections of GH. In addition, the every fourth day administration schedule for GH-CTP shows enhanced body weight gain over GH.

Pharmacodynamically, the long circulation time of GH-CTP relative to GH in the hypophysectomized rats resulted in a prolonged IGF-1 response measured in blood plasma following a single s.c. injection. Subcutaneous administration of a single dose of GH-CTP increased circulating IGF-1 concentrations in a dose-dependent manner in the hypophysectomized rats. At the highest albutropin dose, IGF-1 concentrations were elevated above baseline for as long as 75 hours after a single administration. Thus, the enhanced circulation time of a single dose of GH-CTP resulted in substantial pharmacodynamic improvement over a single dose of GH, raising the possibility that GH-CTP could offer similar growth enhancement with reduced dosing frequency compared with standard GH treatment regimens.

Single CTPs modified hGH-dose of 90 mg/kg in Rhesus and 180 mg/kg in rats were well tolerated in both species. The allometric factor between rats and primates is approximately X2 which is based on the anticipated clearance of proteins in these animals. In-line with industry-accepted extrapolation models for therapeutic proteins' half-life increase between species (FDA Guidance). 90 mg/kg in Primates has a PK profile slightly better than 180 mg/kg of CTPs modified hGH in Rat. Thus, allometric extrapolation to humans supports weekly or once/2 w injection.

The present concept utilizing a CTP-GH construct, reduced dosing frequency compared to the commercial GH recombinant product. Nutropin Depot® is a sustained release formulation of GH approved for use in pediatric populations; however, comparisons to historical controls have revealed that 1- and 2-year growth rates are significantly (p<0.001) lower in children given Nutropin Depot® (1-year growth rate 8.2±1.8 cm/year) than in children treated with GH (one-year growth rate 10.1±2.8 cm/year) (Silverman B L, et al. J. Pediatr. Endocrinol. Metab. 15 (2002), pp. 715-722.). The local effects of subcutaneously administered Nutropin Depot® include nodules, erythema, pain at the injection site, headache and vomiting. Preclinical toxicology studies in both rat and monkey have shown that s.c. administration of CTP-hGH-CTP-CTP produces no local reactions compared to vehicle. Given the medical need for a less frequently administered form of GH, the pharmacologic properties of CTP-hGH-CTP-CTP in this study in rats suggest that this product is favorable also in terms of toxicology and patient compliance. The sustained activity of CTP-hGH-CTP-CTP in the rat support its potential utility as an agent that requires only intermittent administration to attain a therapeutic benefit that is currently achieved with daily dosing.

Example 9

*Long-acting CTP-modified version of human growth hormone (hGH-CTP) was highly effective in growth hormone deficient adults - Phase II Clinical Trial*

A randomized, open-label, Phase II Clinical Trial was conducted to evaluate the safety, tolerability, pharmacokinetics and pharmacodynamic properties of hGH-CTP injected either weekly or twice-monthly in patients who currently receive daily injections of growth hormone. The trial was conducted at multiple sites in six countries. The three main cohorts in the trial received a single weekly dose of hGH-CTP, containing 30%, 45% or 100% of the equivalent cumulative commercial hGH dose that growth hormone-deficient adult patients receive over the course of seven days in the form of daily injections (referred to as the "30%", "45%" and "100%" cohorts, respectively). The data reflect results from 39 patients, 13 in each cohort. 2 females were included in each cohort.

In addition to the three main cohorts, growth hormone deficient adults were enrolled in an experimental fourth cohort, which is conducted outside of the formal Phase II trial. The patients in the experimental fourth cohort receive a single injection of hGH-CTP once every two weeks that contains 50% of the cumulative commercial dose of that growth hormone-deficient adult patients receive over a two-week period in the form of daily injections.

Efficacy for the three main cohorts receiving a single weekly injection of hGH-CTP is defined by measuring daily insulin-like growth factor 1 (IGF-1) levels within the desired therapeutic range over a period of seven days (during the last week of treatment in the study). The desired therapeutic range is defined as between +2 standard deviations through −2 standard deviations from the average IGF-1 levels expected in a normal population, stratified by age group and gender. In addition, the trial measured IGF-1 levels within a narrower range of +/−1.5 standard deviations for the purpose of observing the variance of the patients within the normal range.

Results:

Table 10 contains the average percent of days within the normal therapeutic range (+/−2 SD), average percent of days within a narrower normal therapeutic range (+/−1.5 SD), and average Cmax (highest concentration level) of IGF-1 for males, measured during the last treatment week, expressed in standard deviations from the normal population mean IGF-1 levels.

TABLE 10

Human Phase II Clinical Trial Results.

| Cohort | % Days Within Narrow Normal Range of IGF-1 (+/−1.5 SD) | % Days Within Normal Range of IGF-1 (+/−2 SD) | Avg. Cmax of IGF-1 (preferred below +2 SD) |
|---|---|---|---|
| 30% | 57% | 100% | −0.9 |
| 45% | 100% | 100% | 0.1 |
| 100% | 86% | 100% | 0.4 |

Two mg per week of hGH-CTP, containing 50% of the cumulative weekly hGH dose that an adult patient would usually be prescribed as the initial treatment dose, has a high likelihood of being defined as the starting dose for males and females in the adult Phase III.

There was no evidence of safety and/or tolerability issues, and no indication that hGH-CTP, when used in high doses, induced excessive levels of IGF-1 in patients or even levels above the normal range.

Phase II—IGF-1 Summary and Perspectives

Figure 10:
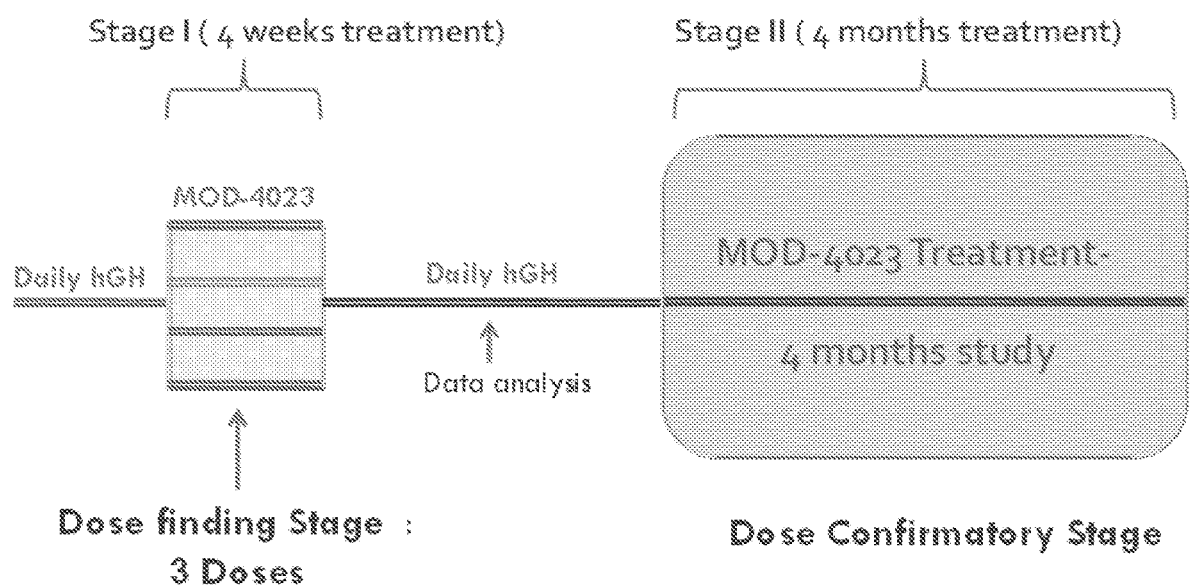
FIG. 10 shows an illustration of the phase II study design.

MOD-4023 Phase II Study Design and Objectives:

A two stage Phase II study confirming CTP-hGH-CTP-CTP (MOD-4023) weekly administration regimen was completed (see FIG. 10). The trial was a switch over study performed in growth hormone deficient (GHD) patients currently on a daily hGH treatment that were considered normalized on their daily treatment prior to MOD-4023 administration, as reflected by IGF-1 SDS levels within the normal range (±2SDS). Stage I of the study was a 4 week dose-finding study (4 injections) supported by a full pharmacokinetics-pharmacodynamics (PK-PD) analysis during the week following the 4$^{th}$ dose of MOD-4023. The major objective of this part was to identify a therapeutic dose range in which the IGF-1 level is kept within a defined range. Another objective was to evaluate the PK-PD profile of MOD-4023 at 3 different doses/multipliers, and confirming a dose-dependent response. The second stage of the study (Stage II) was a 16-week MOD-4023 treatment and dose titration period. All patients who continued to Stage II began with the same MOD-4023 dose level (61.7% of their personal, optimized, weekly cumulative r-hGH dose), but could have their dose modified based on their monitored IGF-1 levels.

In the first part of the study the doses were administered based on percentage of the weekly accumulated hGH in order to evaluate the initial response following a weekly regimen of MOD-4023. For example: A patient receiving 1 mg/day of hGH who was randomized to the 55% cohort was injected with a MOD-4023 dose of $1_{mg}*7_{days}*0.55$ on weekly basis.

Results

Figure 11:
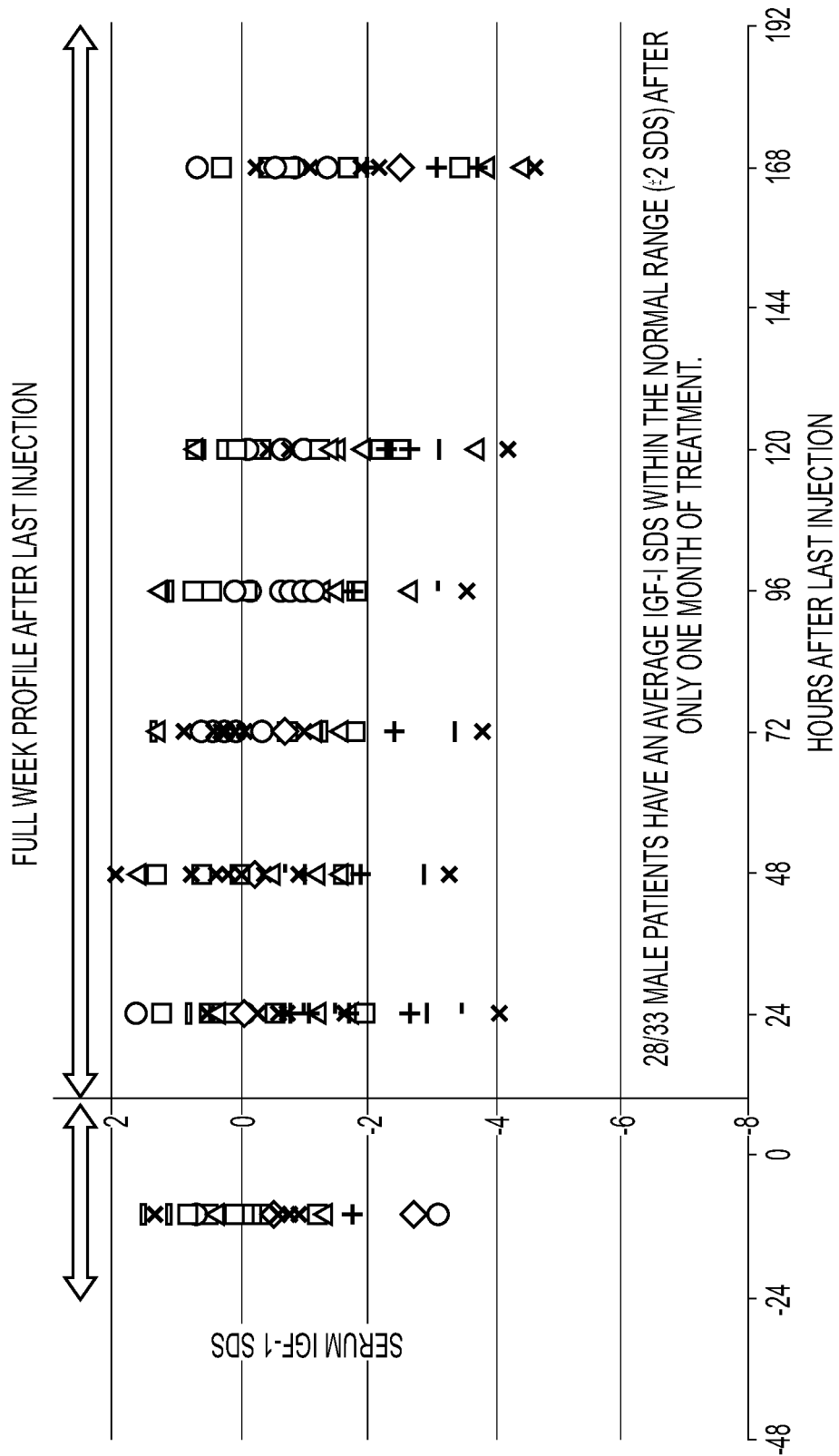
FIG. 11 shows IGF-1 SDS following 4th weekly dose—All Cohorts.

The primary efficacy endpoint of this study was the mean time interval of IGF-1 levels that lay within normal range after the last dose administration during Stage I, expressed in hours. In the final analysis the IGF-1 levels of most of the patients during that week were within the normal range for the entire week (Table 11). Patients who were within the specified SDS range at the final time point were assigned a time interval of 168 hours. None of the patients exceeded +2 SDS at Cmax, indicating that there are no excessive IGF-1 levels. Eighty-five percent of males (28/33 males) had an average IGF-1 SDS within the normal range (±2 SDS) (FIG. 11). The mean time interval of IGF-1 levels that lay within ± the normal range of all three cohorts did not show a significant change as all mean time intervals were within 1 standard deviation of one another.

TABLE 11

Time interval of IGF-1 that lay within ±2SDS after the 4th dose administration during Stage I

| Cohort 2 37% of weekly hGH | Cohort 3 55% of weekly hGH | Cohort 1a 123.4% of weekly hGH |
|---|---|---|
| 156.37 hr | 168 hr | 151.17 hr |
| 120.9 ± 66.24 (hr) | 146.49 ± 50.62 (hr) | 119.9 ± 66.51 (hr) |

As anticipated, administration of 37% of the weekly hGH led to IGF-1 SDS values at the lower part of the normal range and shorter duration within the normal range. A significant improvement in IGF-1 levels as reflected by duration within the normal range was observed when higher dose (55% of the weekly accumulated hGH dose) was administered.

Figure 12:
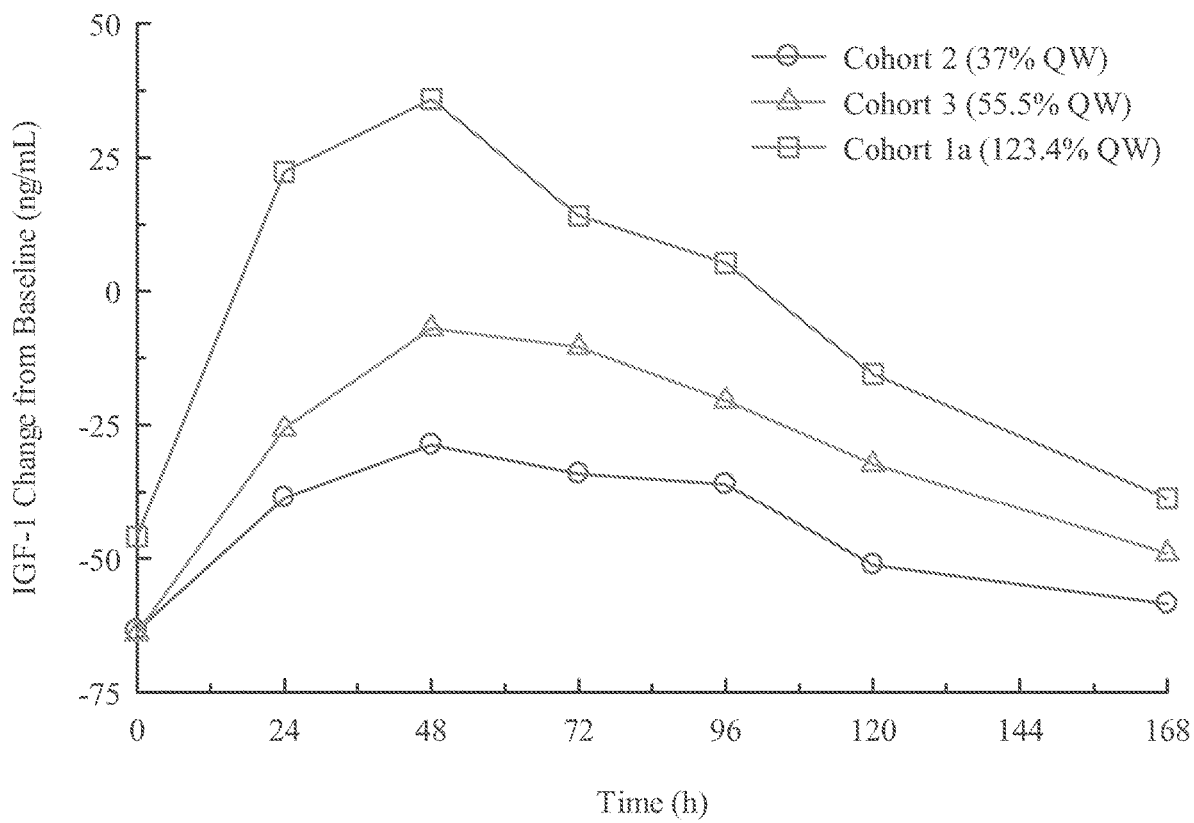
FIG. 12 shows mean change from baseline in IGF-1 plasma concentrations after subcutaneous administration of MOD-4023 to growth hormone deficient adults (Stage I; post $4^{th}$ injection).

A dose dependent IGF-1 response as compared to baseline is shown in FIG. 12. The results presented in FIG. 12, support the notion that IGF-1 levels increase in a MOD-4023 dose dependent manner enabling the adjustment of the IGF-1 weekly profile. Additionally, the mean change from baseline of IGF-1 values 120-168 hr post dosing returns to baseline values, suggesting that IGF-1 trough levels are stable with no deterioration in this normalized growth hormone deficient adults (GHDA) population (FIG. 12).

The Cavg (AUC/Time) which represents the mean IGF-1 exposure, of the daily treated normalized patients was compared to that of the weekly MOD-4023 treatment of the same patients (AUC 0-24/24 hr vs. AUC 0-168/168 hr respectively). Weekly doses of 55-123.4% of the cumulative weekly hGH dose provided comparable IGF-1 exposure as reflected by Cavg, while for patients treated with 37% of the weekly dose a reduced Cavg was observed, which was aligned with our expectations due to the relatively low weekly dose (Tables 12 & 13).

TABLE 12

Summary of pharmacodynamic parameters for IGF-1 after subcutaneous administration of r-hGH to growth hormone deficient adults prior to MOD-4023 administration (Stage 1; 4 w)

| Parameter | Cohort* (optimized hGH treatment) | | |
|---|---|---|---|
| | 2 | 3 | 1a |
| $C_{avg}$ (ng/mL) | 174 ± 57.0 (11) | 178 ± 43.1 (11) | 154 ± 28.5 (11) |

*Mean ± standard deviation (N).

TABLE 13

Summary of pharmacodynamic parameters for IGF-1 after subcutaneous administration of MOD-4023 to growth hormone deficient adults (Stage I; 4 w)

| Parameter | Cohort* (MOD-4023 treatment) | | |
|---|---|---|---|
| | 2 (37%) | 3 (55.5%) | 1a (123.4%) |
| $C_{avg}$ (ng/mL) | 117 ± 32.5 (11) | 147 ± 50.9 (11) | 50.4 (11) 132 |

Based on the PD analysis of Phase II Stage I the following was concluded: 1) Although the study objective was not to optimize patients IGF-1 levels namely, targeting IGF-1 SDS value to 0, (since IGF-1 SDS optimization requires relatively long titration period), still therapeutic dose range for weekly administration of MOD-4023 could be established: around 56%-123% of the weekly cumulative dose of daily hGH. 2) IGF-1 profile following a weekly MOD-4023 administration is relatively flat, as reflected by fairly small difference between Cmax and Ctrough. 3) The Cavg (AUC 0-168/168 hr) which represents the mean weekly IGF-1 exposure correlated to Day 4 values. Therefore, day 4 post MOD-4023 administration was chosen as the monitoring day for IGF-1 levels.

Phase II Stage II (4 Months Extension) Results and Perspectives:

The ability of weekly administration of MOD-4023 to maintain IGF-1 within the normal range at an optimal dose and for a longer period of time was addressed during the second part of the study (Stage II—4 months extension period; FIG. 10). In this study, the same patient population from the first stage was administered with 61.7% of their hGH weekly dose and IGF-1 was monitored every two weeks. The majority of the patients maintain the IGF-1 SDS value within the normal range throughout the study as measured on day 4 post injection. Patients who demonstrated IGF-1 levels below the normal range were further titrated and their MOD-4023 dose was increased (aligned with the clinical practice).

Figure 13:
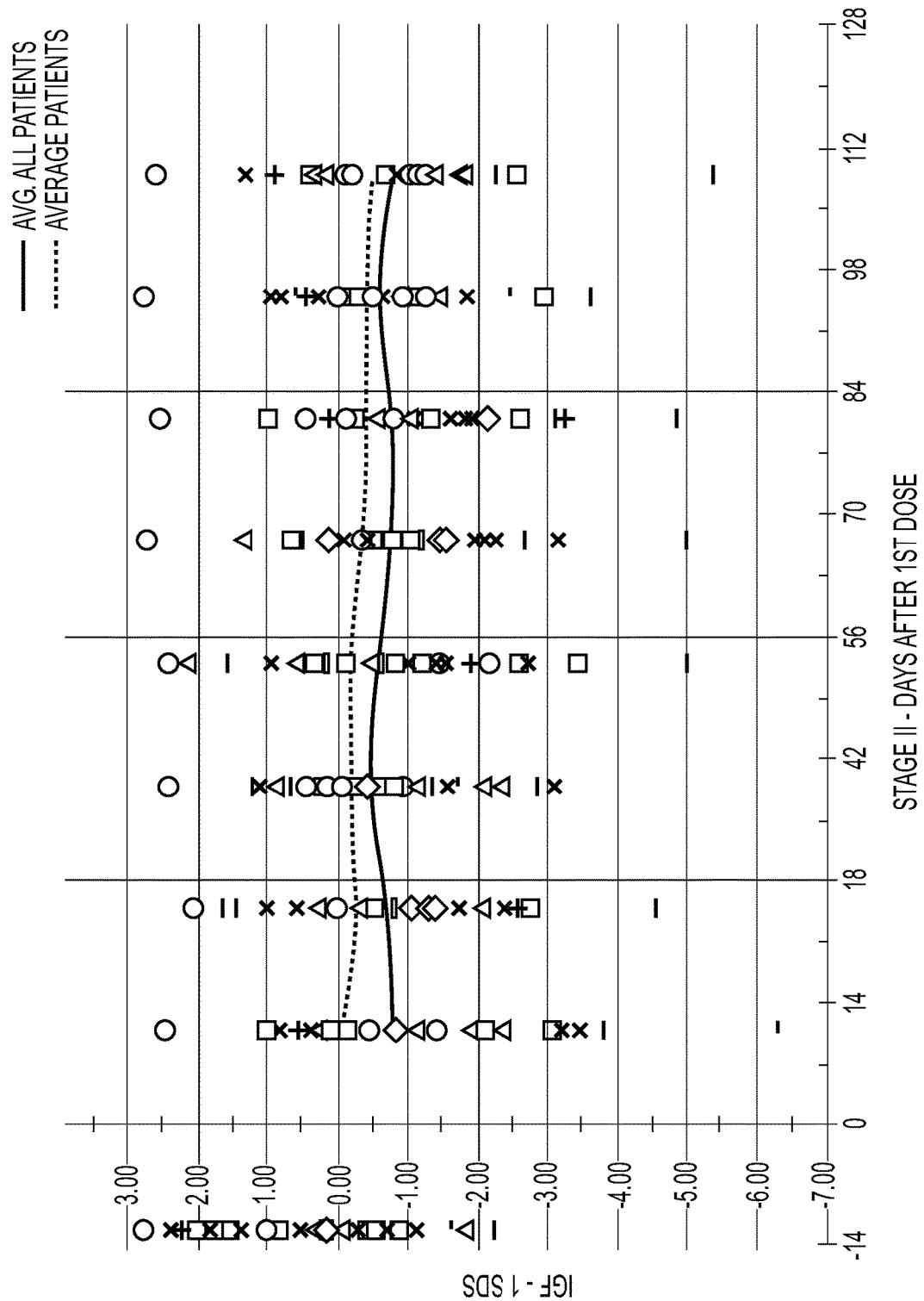
FIG. 13 shows mean IGF-1 levels (determined on day 4 post dosing) during 4 month extension study (52 patients).

Minority of patients with IGF-1 SDS values below the normal range required further titration but demonstrated remarkable improvement in IGF-1 SDS, indicating that IGF-1 profile can be optimized by MOD-4023 dose increment/decrement. Excellent responsiveness and minimal dose modification were needed as presented in FIG. 13 and summarized in Table 14 hereunder.

TABLE 14

Summary of required dose modifications during Stage II.

| Number of Dose Modifications | Males | Females |
|---|---|---|
| No dose modifications | 22 (out of 34) | 3 (of 8) |
| 1 dose modification | 6 (out of 34) | 1 (out of 8) |
| 2 dose modifications | 3 (out of 34) | 3 (out of 8) |
| 3 dose modifications | 3 (out of 34) | 1 (out of 8) |

Based on day 4 IGF-1 SDS values (correlated to Cavg), a significant improvement in IGF-1 levels, as compared to Stage I of the study was observed for the individual patients. This observation further supported the notion that an adjustment period is necessary to reach optimal IGF-1 levels and profile. Females are known to be less sensitive to hGH replacement treatment (MOD-4023 as well) and usually require higher doses and longer period of titration. In addition, IGF-1 SDS levels as measured on day 4 were maintained constantly at a similar values within the normal range during the 4 month extension period, indicating that MOD-4023 can be administered in a weekly regimen. Following consecutive administrations of MOD-4023 no major decrease in IGF-1 levels at day 4 has been observed indicating that the Cmax and Ctrough of the "sinusoidal" behavior of IGF-1 are maintained along the study, confirming again weekly regimen of MOD-4023.

In conclusion, MOD-4023 should obviate the need for the numerous injections now required for the treatment of GHD. The results of this study have demonstrated that MOD-4023 can be injected once per week and achieve the clinical efficacy endpoints assessed, while maintaining a favorable safety profile. A GH treatment regimen that requires less frequent injections may improve compliance and potentially overall outcomes.

Hence, based on the achieved IGF-1 profile and the Phase II safety and tolerability results, the recommended injection frequency and dosing for the Phase III study are: a single weekly injection of MOD-4023 containing 61.7% of the cumulative weekly hGH dose, personalized for each patient.

Example 10

Administration of a CTP-modified version of human growth hormone (hGH-CTP) improved pharmacokinetics in pre-pubertal growth hormone deficient (GHD) children

Figure 14:
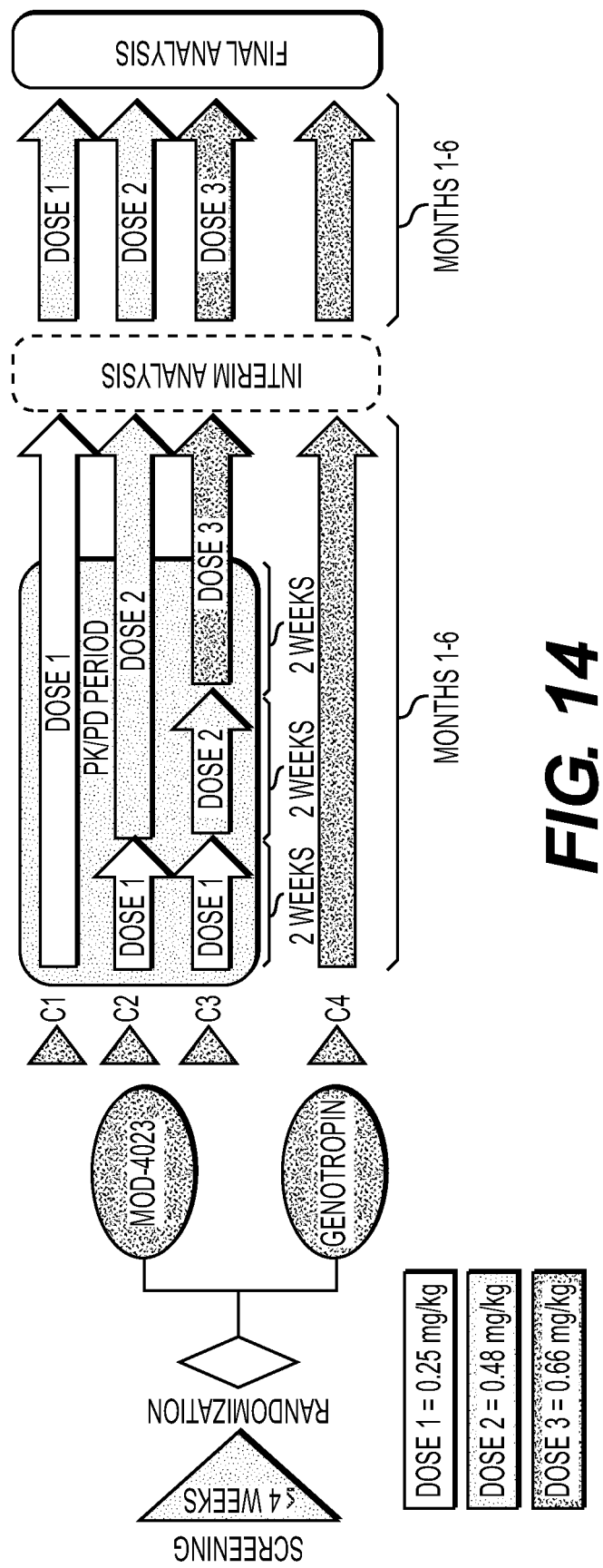
FIG. 14 is schematic representation of phase II clinical study of MOD-4023.

A randomized, open-label, Phase II Clinical Trial was conducted to evaluate the safety, tolerability pharmacokinetics and pharmacodynamics properties of three MOD-4023 doses to that of a commercially available standard daily recombinant human growth hormone. The study consisted of a 6 month screening and two active treatment periods: a 6 month treatment including PK/PD sampling followed by an additional 6 month continuous repeated dosing period as outlined in FIG. 14. The secondary objectives were to evaluate the pharmacokinetics (PK) and pharmacodynamics (PD) profiles of three different doses of MOD-4023 in pre-pubertal growth hormone deficient (GHD) children and to select the optimal dose of MOD-4023 for the subsequent phase 3 study on the basis of safety and efficacy.

In order to introduce naïve patients to the allocated MOD-4023 dose (see Table 15) in a gradual manner, a stepwise dose increase was implemented. All patients randomized to receive one of the three MOD-4023 doses started treatment for 2 weeks with the low MOD-4023 dose (0.25 mg/kg). Based on the patient's dose allocation, this was followed by a dose increase to the next dose level every two weeks until the final allocated dose has been reached.

TABLE 15

Dose Cohorts

| Cohort | MOD-4023/Genotropin Dose |
|---|---|
| 1 | 0.25 mg MOD-4023 protein/kg/week equivalent to 0.18 mg hGH/kg weekly injection. |
| 2 | 0.48 mg MOD-4023 protein/kg/week equivalent to 0.35 mg hGH/kg weekly injection. |
| 3 | 0.66 mg MOD-4023 protein/kg/week equivalent to 0.48 mg hGH/kg weekly injection. |
| 4 | Genotropin: 0.034 mg/kg/day. |

Subsequent to the second dose administration of the targeted dose, limited (population based) PK and PD sampling was performed as described in Table 16.

TABLE 16

Dose Increase Scheme for MOD-4023 Cohorts

| | Dosing Scheme | | | | | |
|---|---|---|---|---|---|---|
| Cohort | Week 1 | Week 2 | Week 3 | Week 4 | Week 5 | Week 6 |
| Cohort 1 | 0.25 mg protein/kg/week PK/PD sampling | | | | | |
| Cohort 2 | 0.25 mg protein/kg/week | | 0.48 mg protein/kg/week PK/PD sampling | | | |
| Cohort 3 | 0.25 mg protein/kg/week | | 0.48 mg protein/kg/week | | 0.66 mg protein/kg/week PK/PD sampling | |

Patients allocated to a MOD-4023 dose cohort were randomized within the cohort into one of three blocks and undergone limited PK/PD sampling (4 samples per patient over a period of one week), according to Table 17 below.

TABLE 17

MOD-4023 Population PK and PD Sampling Scheme

| | Visit (V2, V3, V4) | | | | | | |
|---|---|---|---|---|---|---|---|
| | a | b | c | d | e | f | g |
| Block | Time after dosing(h)/ | | | | | | |
| number | 0 h | 6 h | 12 h | 24 h | 48 h | 72 h | 96 h | 120 h | 168 h |
| Block 1 | X | | | X | X | | X | | |
| Block 2 | | X | | | X | X | | X | |
| Block 3 | | | X | X | | X | | | X |

Patients allocated to Cohort 1 underwent limited PK/PD sampling following the 2nd dose of MOD-4023 (V2a-g—week 2) and returned to the medical centers for a single visit 4 days after dosing during week 6 (V4h).

Patients allocated to Cohort 2 came to the medical centers for a single visit 4 days after dosing during week 2 (V2h), underwent limited PK/PD sampling following the 4th dose of MOD-4023 (week 4: the second dose at the allocated dose level; V3a-g) and returned to the medical centers for a single visit 4 days after dosing during week 6 (V4h).

Patients allocated to Cohort 3 came to the medical centers for a single visit 4 days after dosing during weeks 2 and 4 (V2h and V3h) and underwent limited sampling following the 6th dose of MOD-4023 (week 6: the second dose at the allocated dose level, V4a-g).

At visits 2a and 2h, 3a and 3h, and 4a and 4h the patients underwent physical examination, vital signs, AEs, local tolerability, concomitant medications, parameters of glucose metabolism (fasting glucose and insulin; HbA1C only at V4), other hormonal levels (TSH, fT4, T3, cortisol), routine safety biochemistry and hematology (visits 2a and 2h, 4a and 4h), patient's height and weight, parameters of lipid metabolism, and IGF-1 and IGFBP-3 serum levels.

Figure 17:
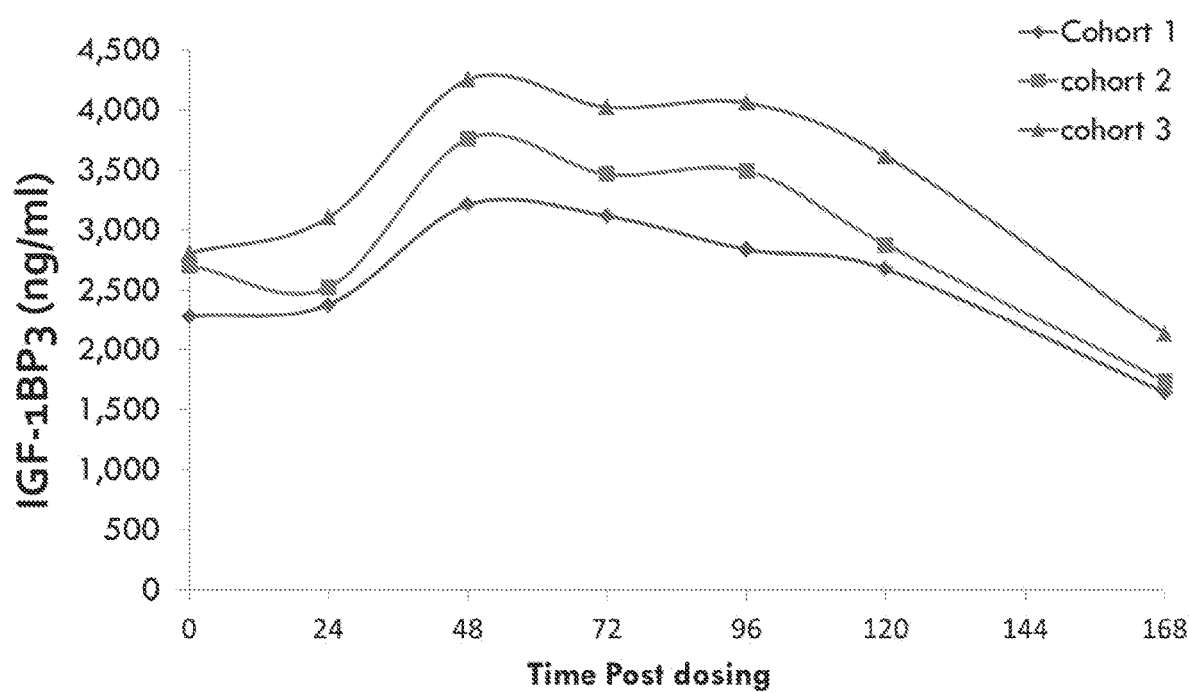
FIG. 17 is a graph showing MOD-4023 Pediatric Phase 2, IGF-1 BP-3 profile during the 2nd week at each final dose.

Patients allocated to the Genotropin cohort (cohort 4) returned to the medical centers for visits 2 and 4, during the 2nd and 6th week of treatment. The following procedures were performed: physical examination, vital signs, AEs, local tolerability, concomitant medications, parameters of glucose metabolism (fasting glucose and insulin; HbA1C only at V4), other hormonal levels (TSH, fT4, T3, cortisol), routine safety biochemistry and hematology, patient's height and weight, parameters of lipid metabolism, IGF-1 and IGF-1 BP-3 serum levels (FIG. 17).

In addition, after the 8th Genotropin dose (start of week 2 of dosing), the patients allocated to the Genotropin cohort were randomized into one of three blocks and underwent limited PK/PD sampling (4 samples per patient over a period of 24 hours), according to Table 18 below:

TABLE 18

Genotropin Population PK and PD Sampling Scheme (Visit 2)

| Block | Time after dosing(h)/ | | | | | | | | |
|---|---|---|---|---|---|---|---|---|---|
| number | 0 h | 1 h | 2 h | 4 h | 6 h | 12 h | 16 h | 20 h | 24 h |
| Block 1 | X | | X | X | | | X | | |
| Block 2 | | X | | X | X | | | X | |
| Block 3 | | | X | | X | X | | | X |

Following the first 6 weeks of the study, all patients visited the hospital on a monthly basis (weeks 10, 14, 18, 22 and 26). Patients allocated to the MOD-4023 dose cohorts (cohorts 1-3) were asked to return 4 days after MOD-4023 dosing in order to obtain MOD-4023, IGF-1 and IGFBP-3 levels and conduct routine safety assessments. In addition, after 5 months of dosing, patients allocated to MOD-4023 dosing were asked to return to the medical center in the morning hours prior to dosing in order to obtain a trough level MOD-4023 and PD (IGF-1 and IGF-1BP-3) samples. Patients allocated to the Genotropin dose cohort (cohort 4) were asked to return on any day during the relevant dosing week.

Results:
Study demographic is presented of all patients in Table 19 below:

TABLE 19

Phase 2 trial baseline demographic:

| | Cohort 1 | | Cohort 2 | | Cohort 3 | | Cohort 4 | |
|---|---|---|---|---|---|---|---|---|
| | Dose | | | | | | | |
| | 0.25 mg/kg/w MOD-4023 | | 0.48 mg/kg/w MOD-4023 | | 0.66 mg/kg/w MOD-4023 | | 0.034 µg/kg/d Genotropin | |
| | N | | | | | | | |
| | 9 | | 9 | | 10 | | 7 | |
| | Mean | SD | Mean | SD | Mean | SD | Mean | SD |
| Age (y) | 6.44 | 2.3 | 6.33 | 2.1 | 6.10 | 2.2 | 5.43 | 1.9 |
| Peak GH (ng/ml)* | 2.84 | 2.9 | 3.58 | 1.7 | 4.41 | 3.2 | 2.92 | 2.4 |
| HV SDS | −3.05 | 2.0 | −2.82 | 1.1 | −3.11 | 1.8 | −3.36 | 2.0 |
| HT SDS | −3.99 | 0.9 | −3.82 | 0.8 | −3.91 | 1.1 | −4.79 | 1.7 |
| Ht SDS-TH SDS | −3.47 | 0.9 | −3.23 | 0.7 | −3.25 | 1.3 | −4.20 | 1.8 |
| Screening $IGF_{-1}$ SDS | −2.48 | 0.8 | −2.28 | 0.7 | −1.81 | 0.7 | −2.34 | 1.2 |
| Gender (%) | F | M | F | M | F | M | F | M |
| | 1 (11.1) | 8 (88.8) | 4 (44.4) | 5 (55.6) | 3 (30) | 7 (70) | 3 (42.9) | 4 (57.1) |

Figure 15:
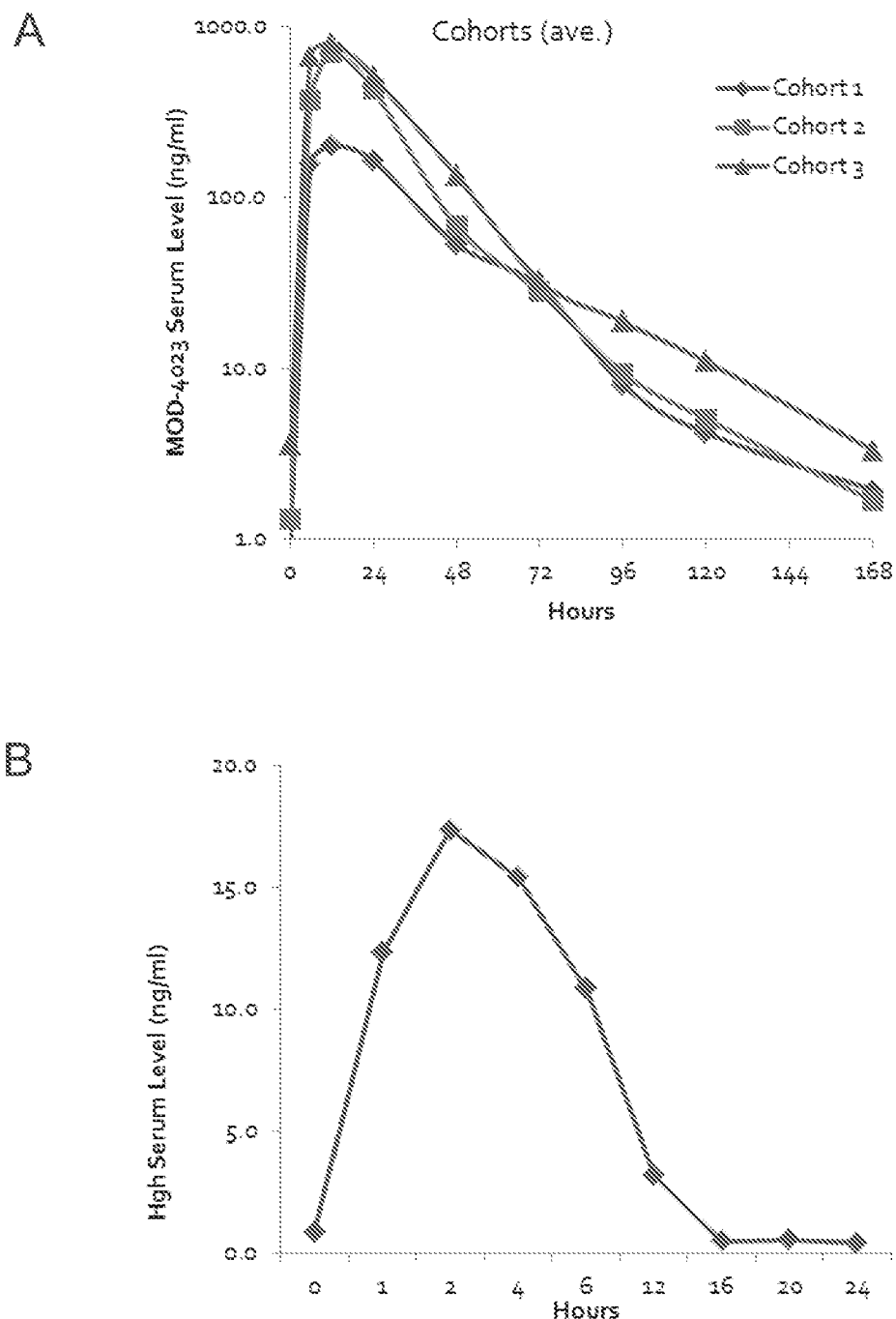
FIG. 15 is a graph showing (A); average MOD-4023 weekly PK profile, and (B); average hGH Daily PK Profile.

The average PK profile of MOD-4023 administrated to naïve GHD at their final administered dose is provided in FIG. 15 while the PK parameters are provided on Table 20 below:

TABLE 20

Comparative Average PK Parameters

| | | MOD-4023 | | | hGH |
|---|---|---|---|---|---|
| | Units | C1 (n = 13) | C2 (n = 12) | C3 (n = 13) | C4 (n = 11) |
| $T_{1/2}$ | hr | 36.1 | 29.2 | 29.1 | 3.6 |
| $T_{max}$ | hr | 12 | 12 | 12 | 2 |
| $C_{max}$ | ng/ml | 459.9 | 810.2 | 795.5 | 17.3 |
| AUC 0-inf_obs | ng/ml * hr | 10943.4 | 20050.3 | 25503.1 | 135.7 |
| Cl/F_obs | (mg/kg)/(ng/ml)/hr | 2.28E−05 | 2.39E−05 | 2.59E−05 | 2.51E−04 |

As anticipated MOD-4023 administered once a week demonstrated an extended half-life which was shown to be 8 fold higher compared to daily hGH. In addition a dose dependent response was observed as reflected by the AUC values of each MOD-4023 dose.

The Dose dependent response was maintained throughout the first 6 months of weekly administration of MOD-4023 (data not shown).

Figure 16:
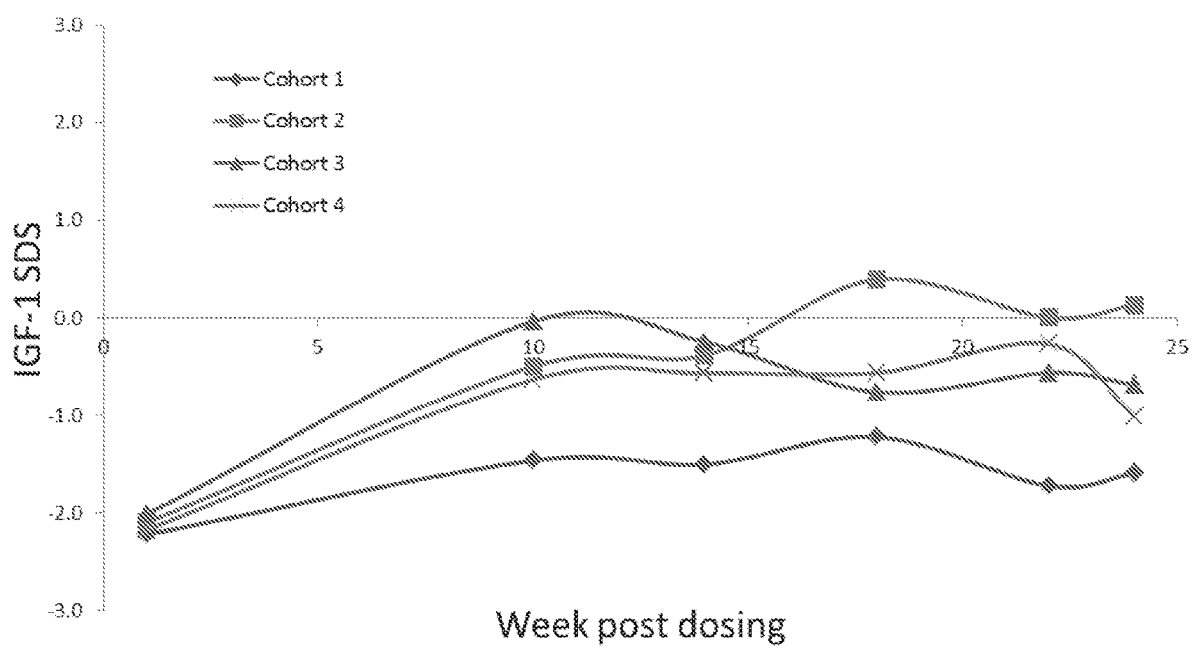
FIG. 16 is a graph showing MOD-4023 Pediatric Phase II, 6 months average IGF-1 SDS profile.
Figure 21:
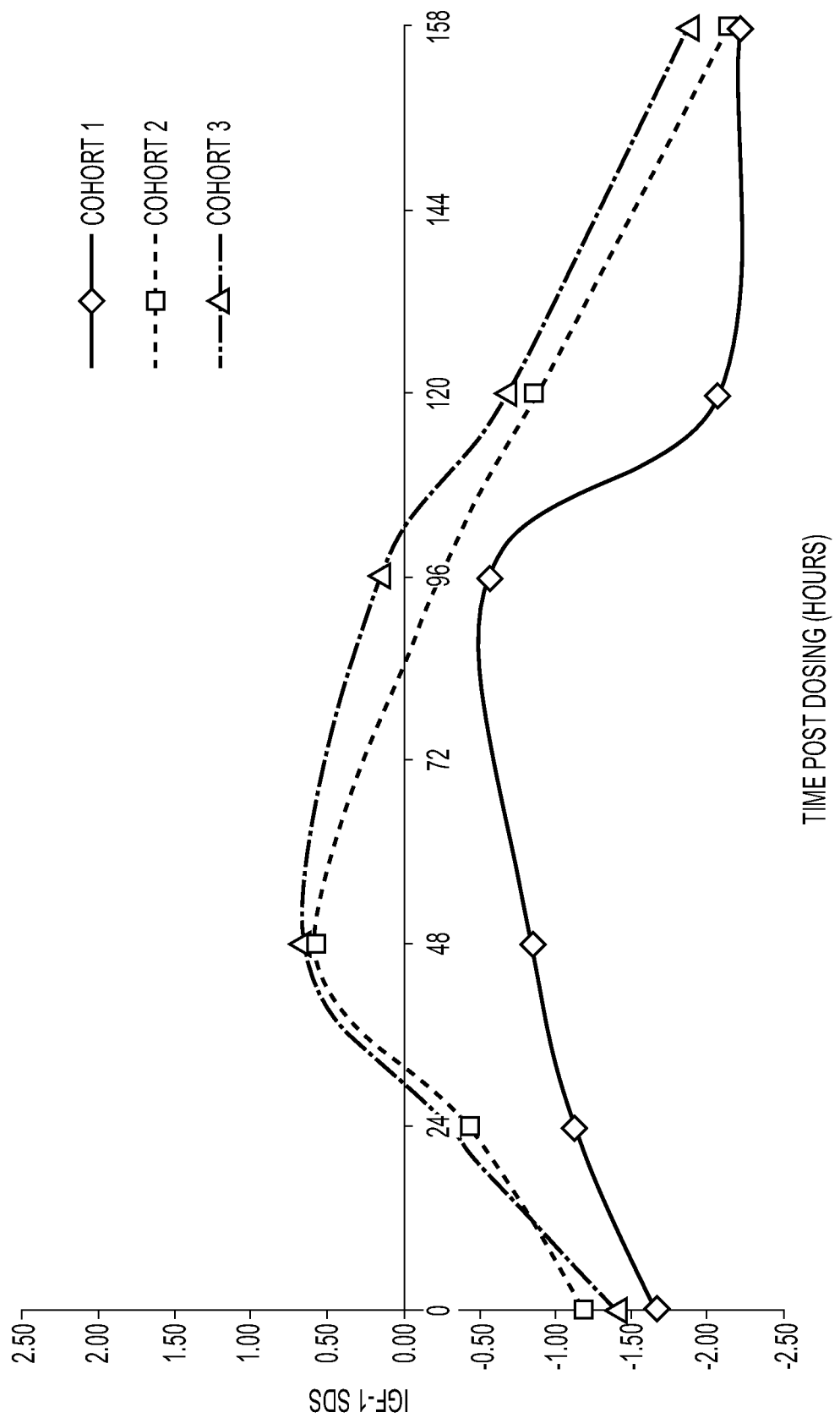
FIG. 21 is a graph showing MOD-4023 Pediatric Phase II-PD (IGF-1 SDS) Profile at each final dose.
Figure 23:
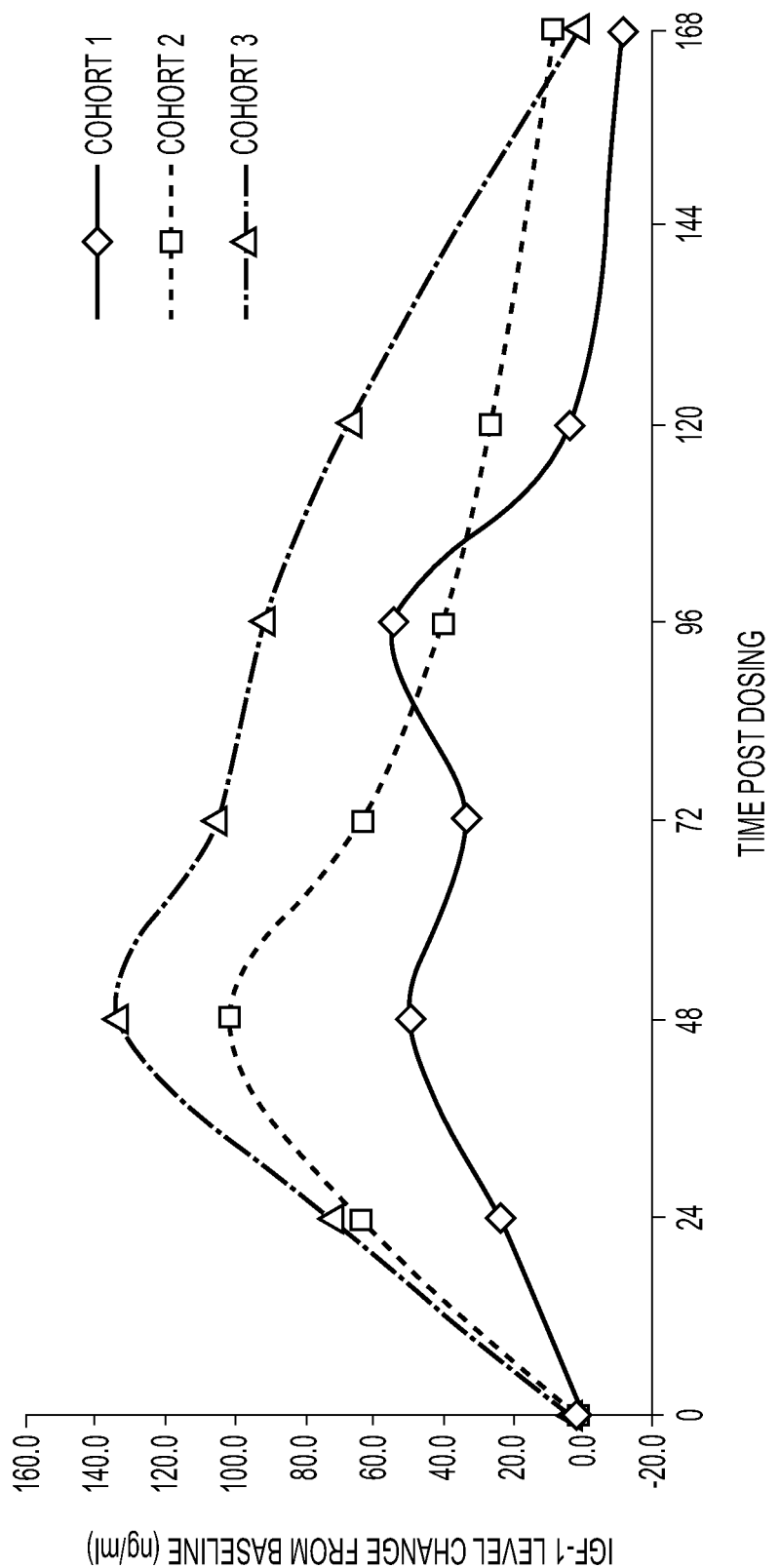
FIG. 23 is a graph showing MOD-4023 Pediatric Phase II-IGF-1 Change from Baseline at the Final Dose.

IGF-1 which is a validated surrogate marker for hGH activity was also increased at a dose dependent level (FIG. 23) maintaining the target values (above −2 height SD score [SDS]) for the majority of the week without excessive levels (>2SDS, FIG. 21). The IGF-1 SDS levels continued to moderately elevate at a dose dependent manner during the first 6 month of the study, without reaching excessive levels which are above 2SDS (FIG. 16).

Figure 18:
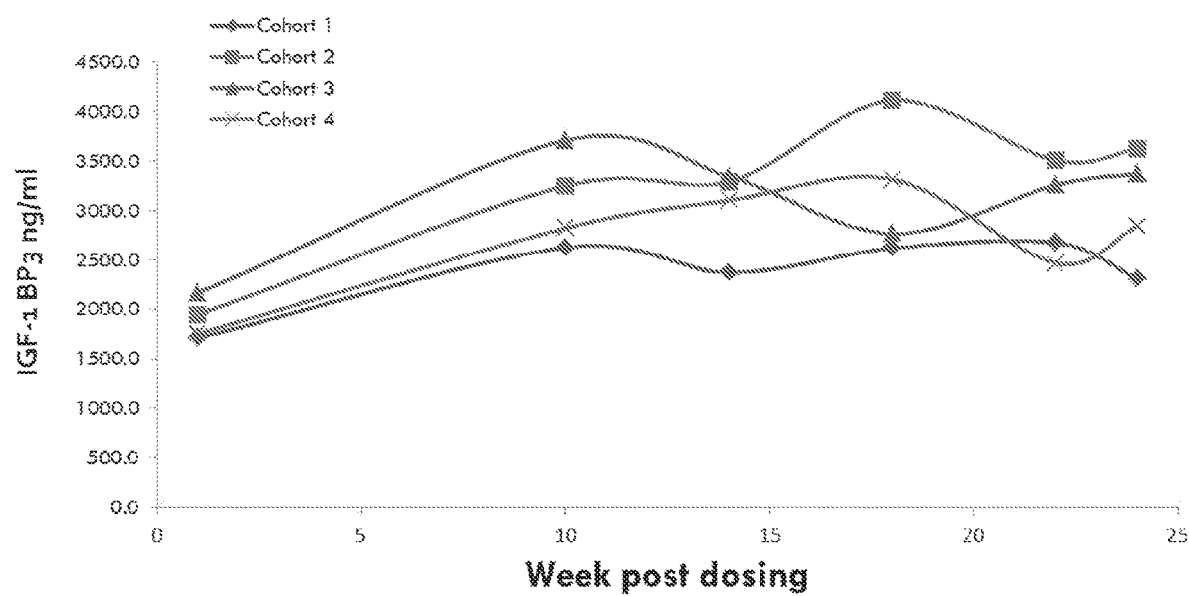
FIG. 18 is a graph showing MOD-4023 Pediatric Phase II-6 months average IGF-1 BP-3 Profile.
Figure 19:
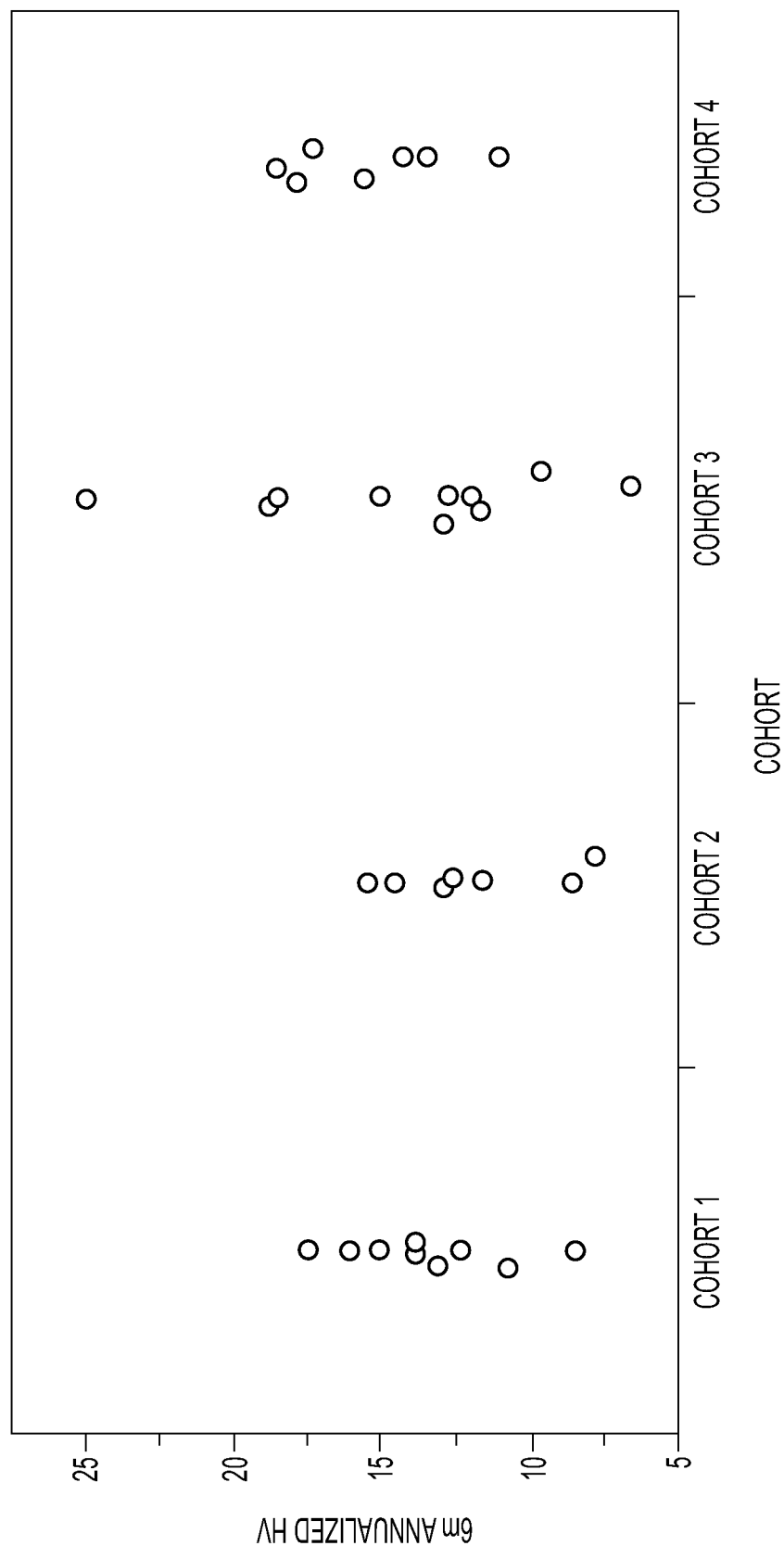
FIG. 19 is a graph showing MOD-4023 Pediatric Phase II HV Results 6 months Annualized Height Velocity for all patients completing 6 m treatment.

The hGH treated arm (cohort 4) also demonstrated an elevation in IGF-1 SDS values that were very similar to the trend observed with two highest cohorts of MOD-4023. Furthermore IGF-1 BP-3 values also increased in a dose dependent manner upon MOD-4023 administration reaching steady-state values around week 15 (FIGS. 17 and 18 respectively). Altogether, the two pharmacodynamics profiles of IGF-1 and IGF1BP-3 confirm that MOD-4023 single weekly injection can replace 7 daily injections at a similar dose range Height velocity was monitored at pre dose and 6 month post weekly dosing of MOD-4023 or daily dosing of hGH. For all cohorts an excellent growth response was obtained with no statistical difference between the different cohorts (Table 21 and FIG. 19), further confirming that weekly injection of MOD-4023 can enable proper growth as daily hGH.

TABLE 21

MOD-4023 6 m Annualized Height Velocity - all patients completing 6 m treatment

| Cohort | Dose | N | Mean (CM) | Std Dev |
|---|---|---|---|---|
| Cohort 1 | 0.25 mg/kg/w MOD-4023 | 9 | 13.48 | 2.71 |
| Cohort 2 | 0.48 mg/kg/w MOD-4023 | 9 | 12.25 | 2.64 |
| Cohort 3 | 0.66 mg/kg/w MOD-4023 | 10 | 14.37 | 5.26 |
| Cohort 4 | 0.034 µg/kg/d Genotropin | 7 | 15.46 | 2.68 |
| | Historical data - daily hGH | | ~10 | |

Figure 20:
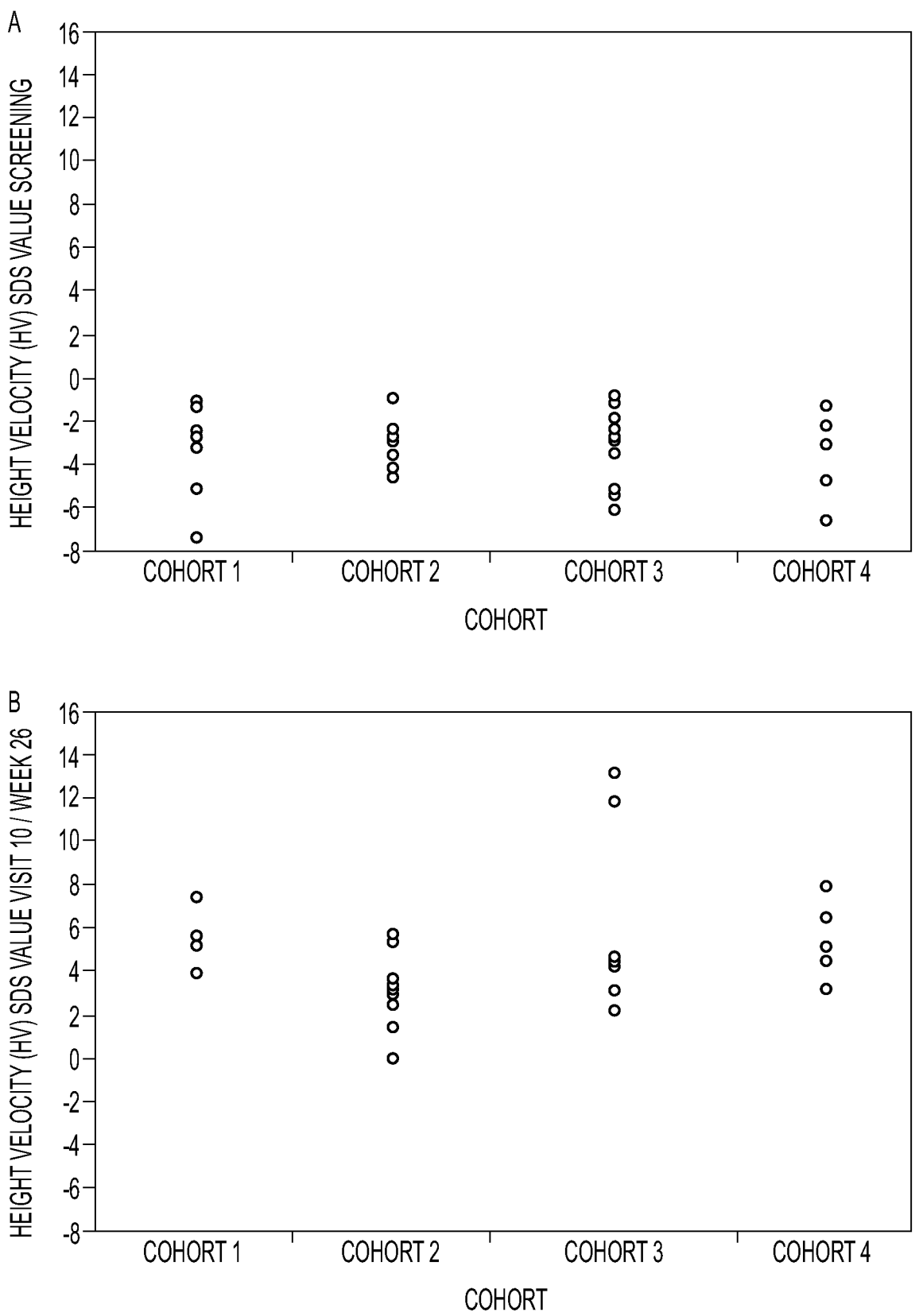
FIG. 20 is a graph showing (A); MOD-4023 Pediatric Phase II Pre-Study HV SDS Results and (B); 6 months HV SDS Results.
Figure 22:
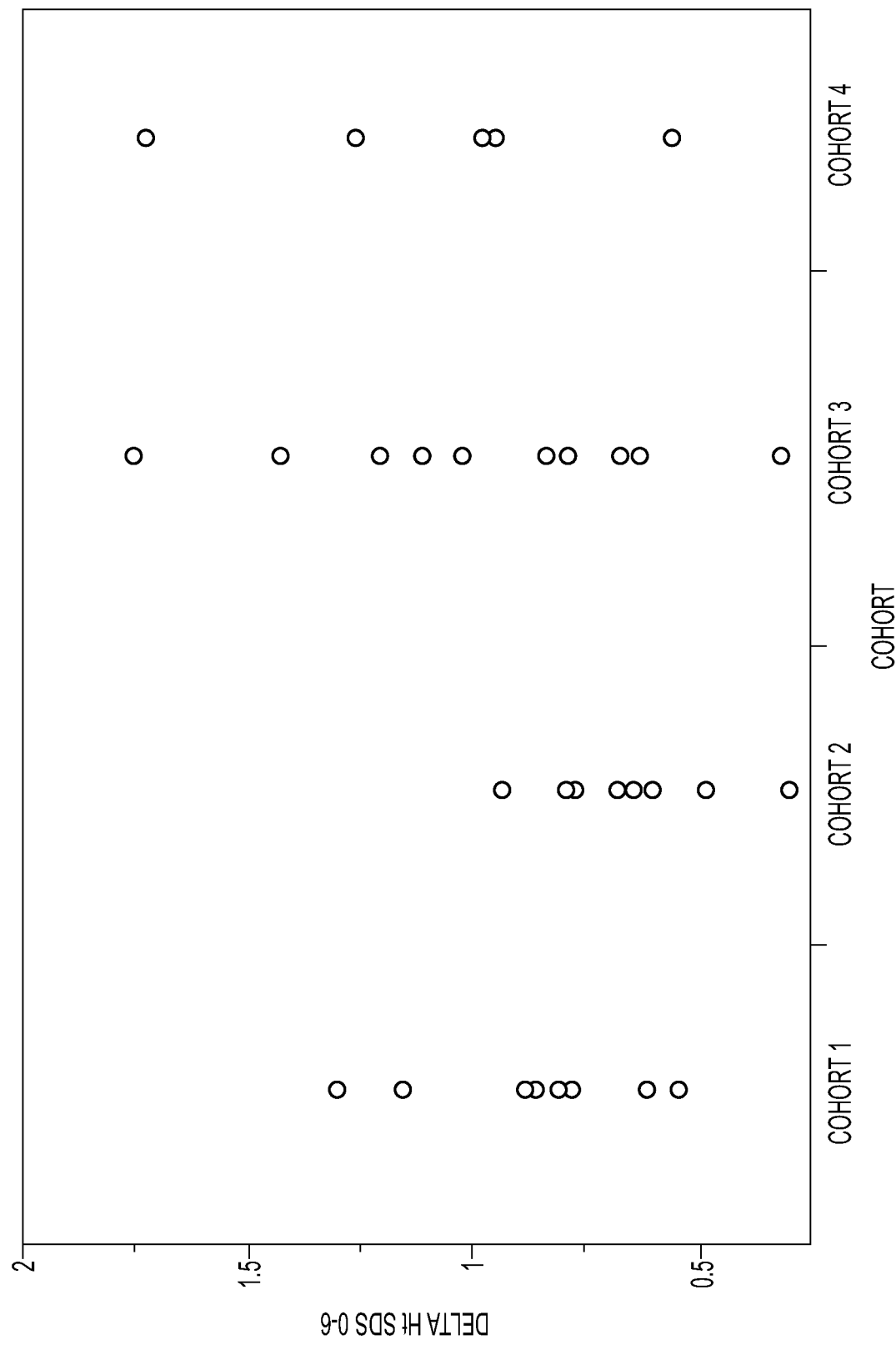
FIG. 22 is a graph showing ΔHeight SDS.

In parallel, an excellent increase in height velocity SDS was also obtained (Table 22, Table 23, and FIG. 20). Finally delta height SDS demonstrated excellent correlation to patients' catch up growth (FIG. 22).

TABLE 22

MOD-4023 Ped. Phase 2 - Pre-Study HV SDS Results

| Cohort | Dose | N | Mean | Std Dev | SE Mean |
|---|---|---|---|---|---|
| Cohort 1 | 0.25 mg/kg/w MOD-4023 | 8 | −3.21 | 2.05 | 0.72 |
| Cohort 2 | 0.48 mg/kg/w MOD-4023 | 8 | −2.94 | 1.14 | 0.40 |
| Cohort 3 | 0.66 mg/kg/w MOD-4023 | 10 | −3.11 | 1.79 | 0.56 |
| Cohort 4 | 0.034 µg/kg/d Genotropin | 7 | −3.36 | 1.98 | 0.75 |

TABLE 23

MOD-4023 Ped. Phase 2 - 6 m HV SDS Results

| Cohort | Dose | N | Mean | Std Dev | SE Mean |
|---|---|---|---|---|---|
| Cohort 1 | 0.25 mg/kg/w MOD-4023 | 8 | 5.03 | 1.23 | 0.44 |
| Cohort 2 | 0.48 mg/kg/w MOD-4023 | 8 | 3.23 | 1.88 | 0.67 |
| Cohort 3 | 0.66 mg/kg/w MOD-4023 | 10 | 5.73 | 3.72 | 1.18 |
| Cohort 4 | 0.034 µg/kg/d Genotropin | 7 | 5.67 | 1.53 | 0.58 |

Conclusion

All doses provided a good catch-up growth response. Preliminary statistical analysis indicates that there are no statistically significant differences between the cohorts but there are some limitations as to the limited number of patients per cohort and the relatively severe GHD patients.

Example 11

*Formulation development of MOD-4023*

The protein: MOD-4023 is a long-acting recombinant human Growth Hormone (hGH) for subcutaneous administration. MOD-4023 consists of hGH fused to three copies of the C-terminal peptide (CTP) of the beta chain of human Chorionic Gonadotropin (hCG); The CTP includes four O-glycosylation sites and therefore, the protein is a single chain of 275 amino acids with up to twelve O-linked carbohydrates. The protein is manufactured in CHO cells from a producing clone.

Producing Clone: Clone #2 was the original clone used for the early toxicological studies, Phase I and Phase II (adults). Stability data for the DS and DP for this clone are available for up to 2 years at −20° C. and 5° C. Conversion to a new producing clone (Clone #28) was carried out to improve productivity and clone stability. Clone #28 DP supported the long term toxicological studies and Phase II in children, and will support all further clinical activities and commercial manufacturing. Stability data for the DP for this clone are available for up to 1 year at −20° C. and 5° C.

Manufacturing CMO: The manufacturing of MOD-4023 was executed by Xcellerex (USA) at early stages and supported non-clinical studies up to Phase II. The process was transferred to Rentschler Biotechnologie (RB), (Germany). Two GMP batches were already produced at RB.

Additional Information

Physicochemical Properties—
Highly glycosylated and negatively charged with pI=3-4.5
Density: 1.0216 g/ml
Soluble in aqueous solution
Liquid formulation for both DS and DP: 10 mM Citrate, 147 mM NaCl pH 6.
Final concentration of DS: 40 mg/ml
Final concentration of DP: 5, 10, 20 and 40 mg/ml
Primary Packaging—
2R vials (Schott)
Stoppers (West)
Aluminum Seals (West)
Future Primary Packaging—PEN Device Objective of Formulation Optimization To Develop a Stable Liquid Formulation for MOD-4023:
1. First objective: 2 years stability at 5° C. in vials
2. Second objective: 2 years stability at 5° C. in cartridges
Analytical Tests Needed:
RP-HPLC (Validated method)
SEC-HPLC (Validated method)
CZE (TBD) (Established method)
Timeline:
Based on the stability data, 2 w at 25° C. can be employed to predict product stability at 5° C. to enable an initial assessment for comprehensive matrix formulation study.

Stability Data

Figure 25A:
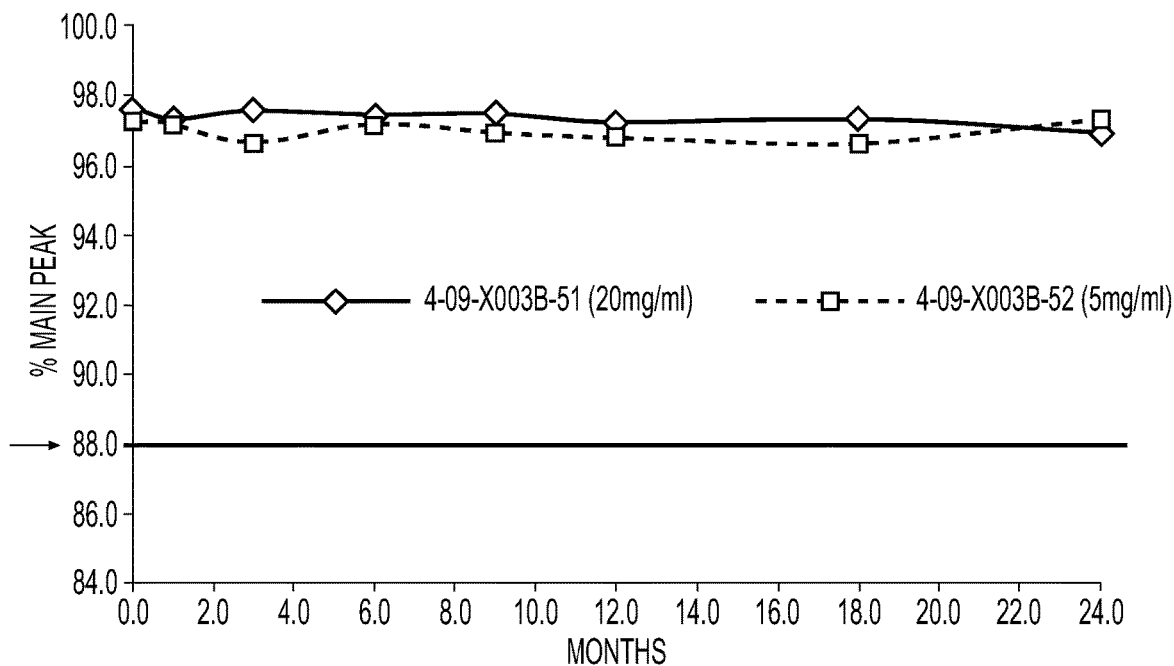
FIG. 25A is a graph showing Clone 2 MOD-4023 RP-HPLC Stability at −20° C.
Figure 25B:
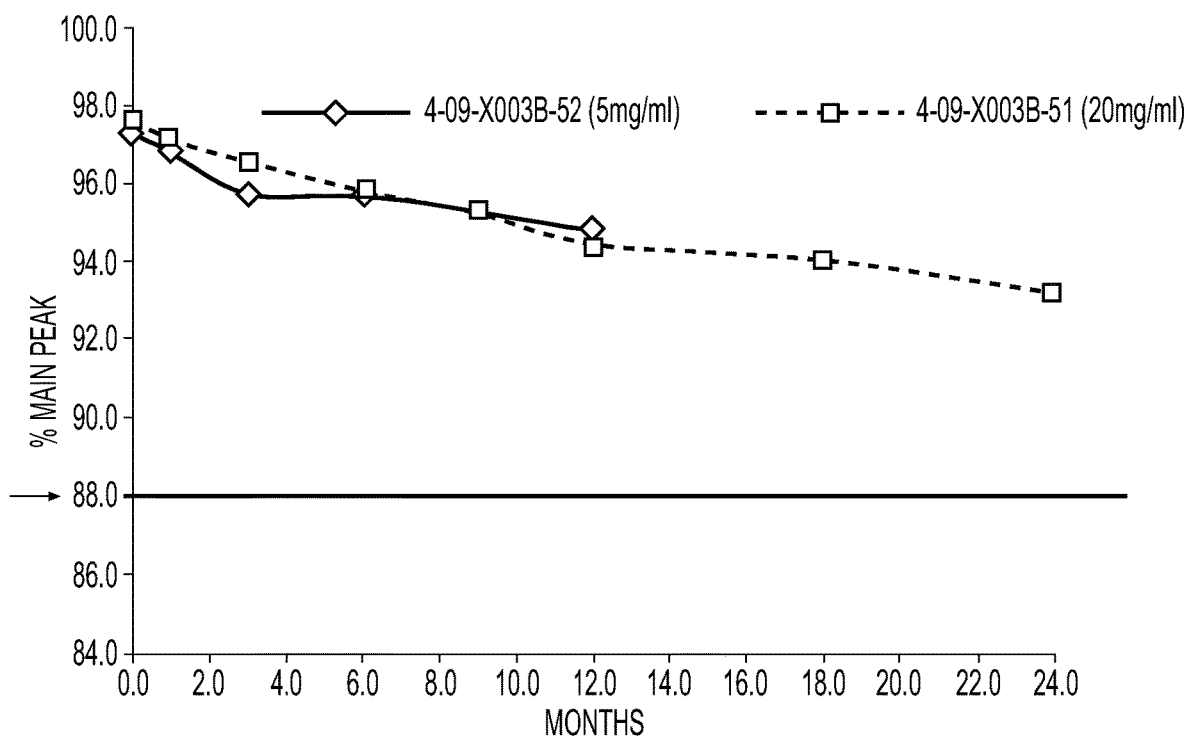
FIG. 25B is a graph showing Clone 2 MOD-4023 RP-HPLC Stability at 5° C.
Figure 26:
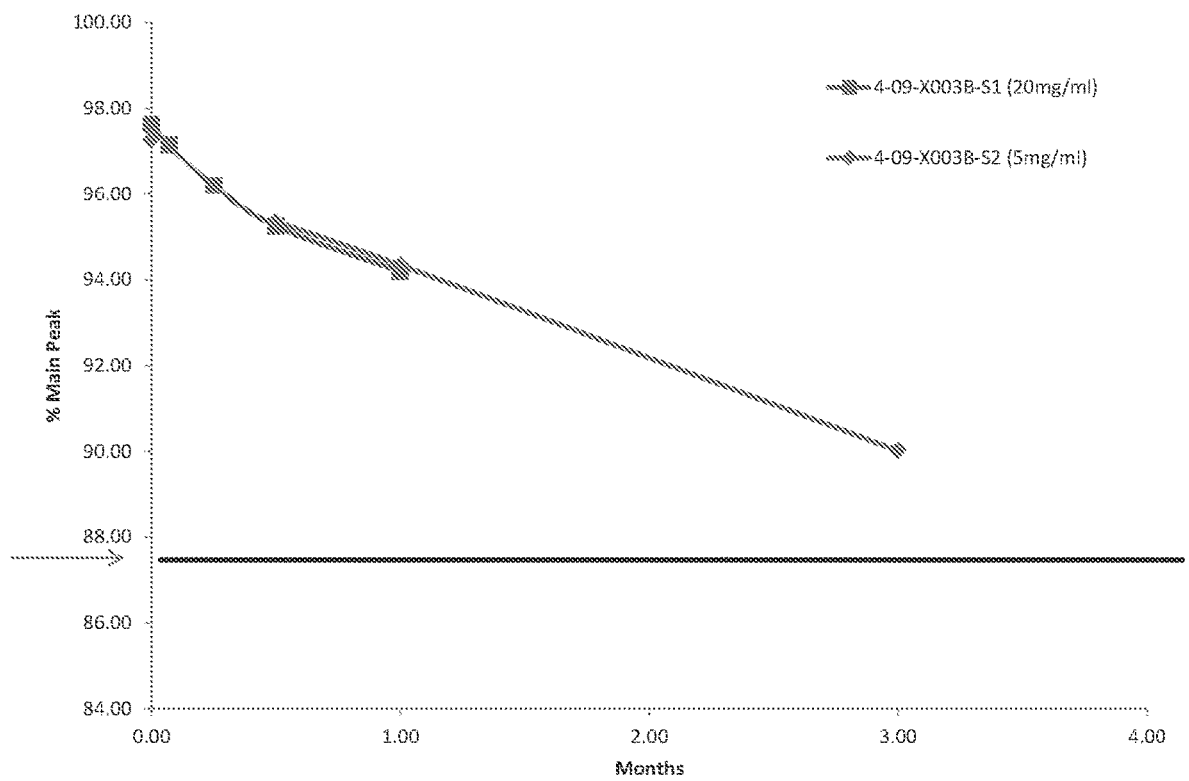
FIG. 26 is a graph showing Clone 2 MOD-4023 RP-HPLC Stability at 25° C.
Figure 27A:
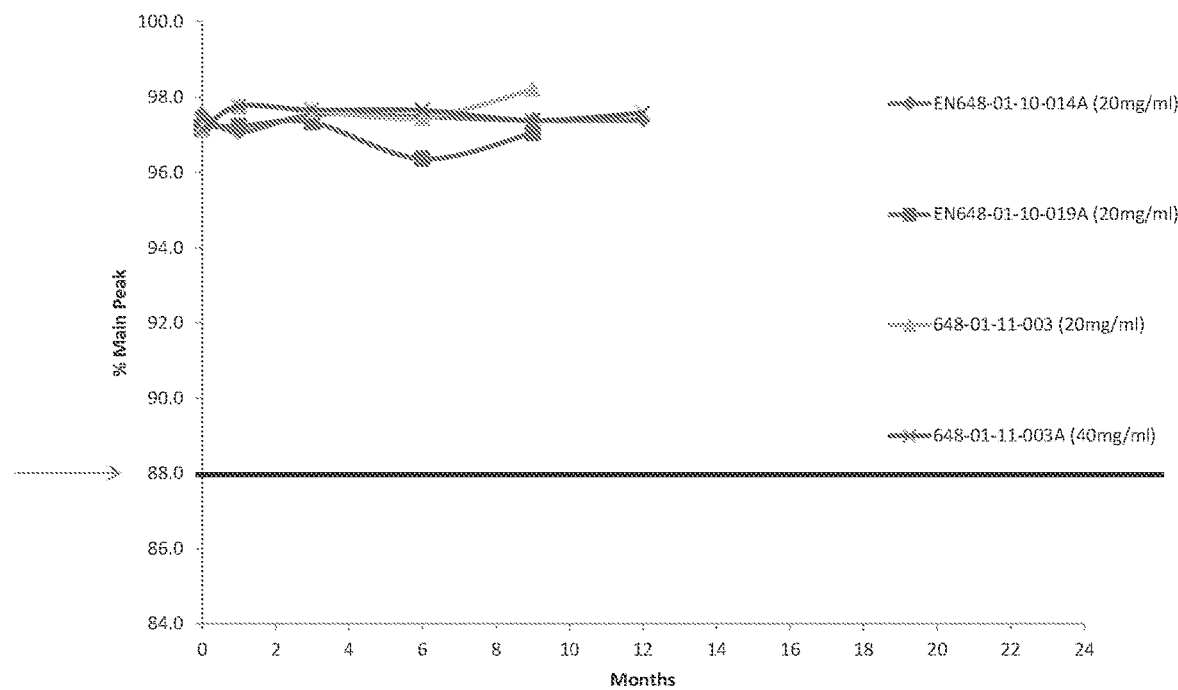
FIG. 27A is a graph showing Clone 28 (Xcellerex) Stability at −20° C. (RP-HPLC).
Figure 27B:
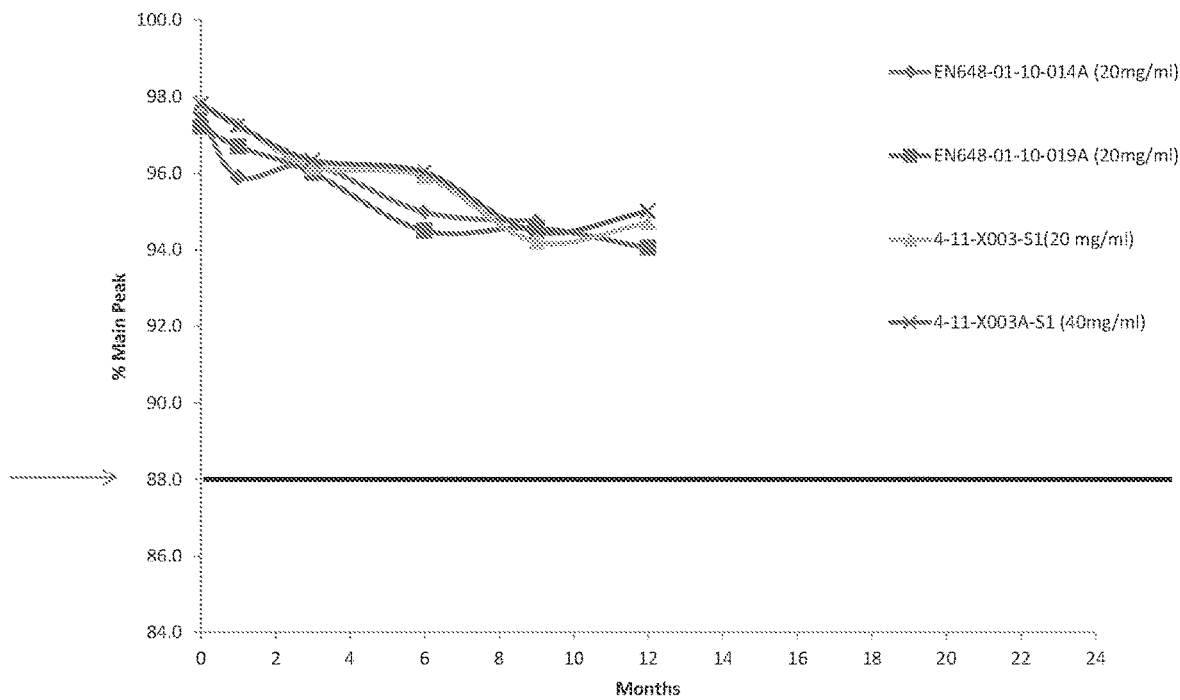
FIG. 27B is a graph showing Clone 28 (Xcellerex) Stability at 5° C. (RP-HPLC).
Figure 28A:
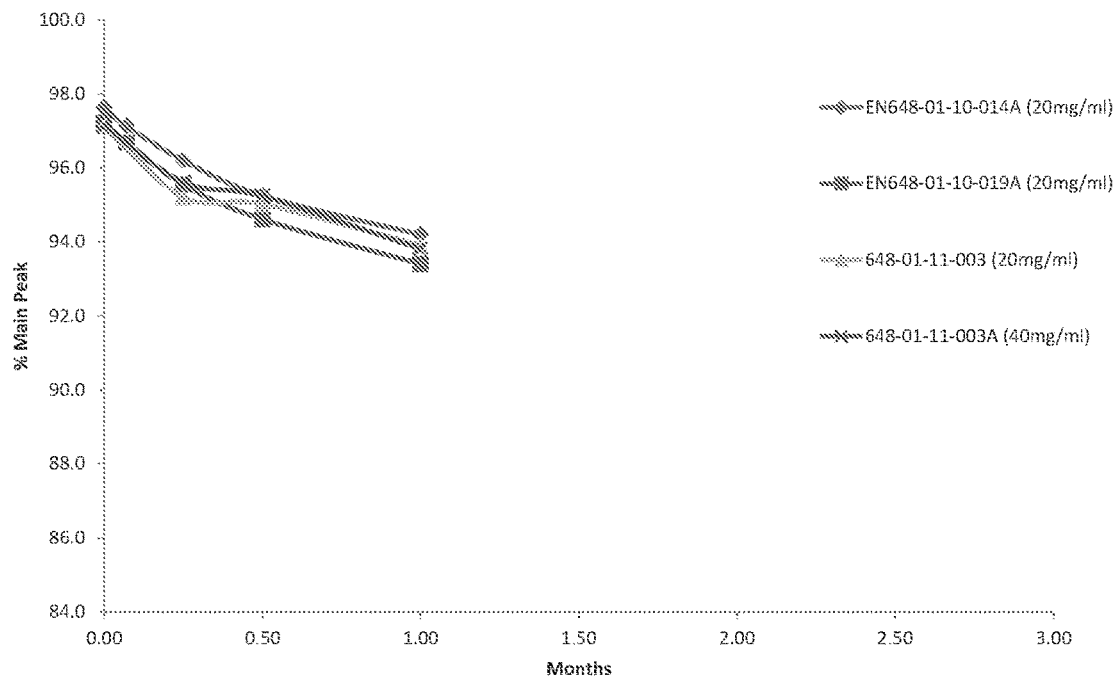
FIG. 28A is a graph showing Clone 28 (Xcellerex) Stability at 25° C. (RP-HPLC).

Data shows non-GMP and GMP batches produced in 10 mM Citrate, 147 mM NaCl pH 6 (FIG. 24). Data also shows that MOD-4023 Clone 2 is stable at 5° C. for 24 months in 20 mg/m and that there's a similar stability profile between 5 mg/ml and 20 mg/ml (see FIGS. 25A and 25B). Moreover, MOD-4023 Clone 2 is stable for 3 months at room temperature (see FIG. 26). MOD-4023 Clone 28 is stable at 5° C. for 12 months at 20 mg/ml or 40 mg/ml; DP Main Peak Specification >88% (FIG. 27A and FIG. 27B). MOD-4023 Clone 28 is stable for at least one month at room temp. (FIG. 28A).

Figure 28B:
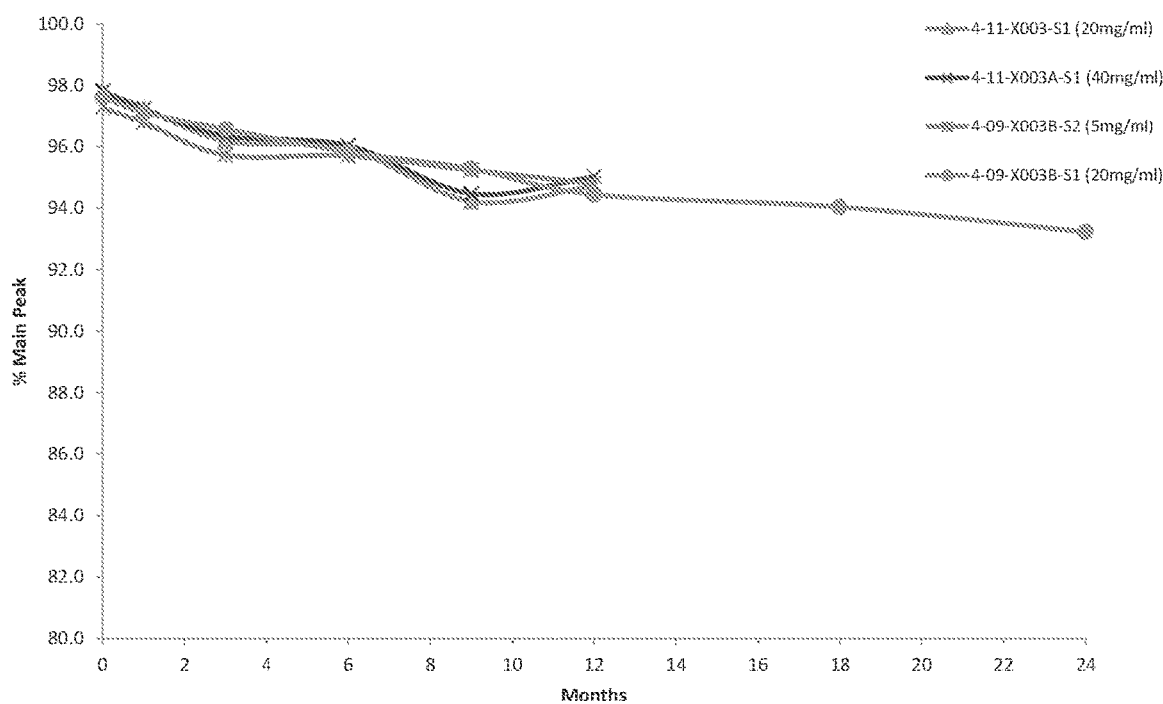
FIG. 28B is a graph showing comparison of Clones 2 and 28 Stability Profiles at 5° C. (RP-HPLC).
Figures 30A, 30B, 30C:
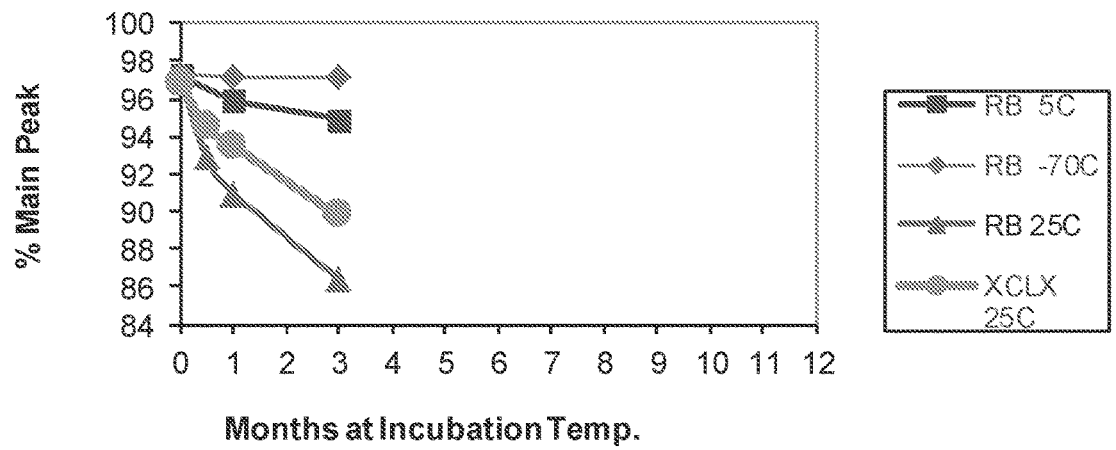
FIG. 30A is a graph showing differences in RP-HPLC Stability results between Rentschler (RB) and Xcellerex (XCLX)—Main Peak.
FIG. 30B is a table showing main Peak Stability results of GMP1 (RB).
FIG. 30C is a table showing main Peak Stability results of XCLX (tested at RB).
Figures 31A, 31B, 31C:
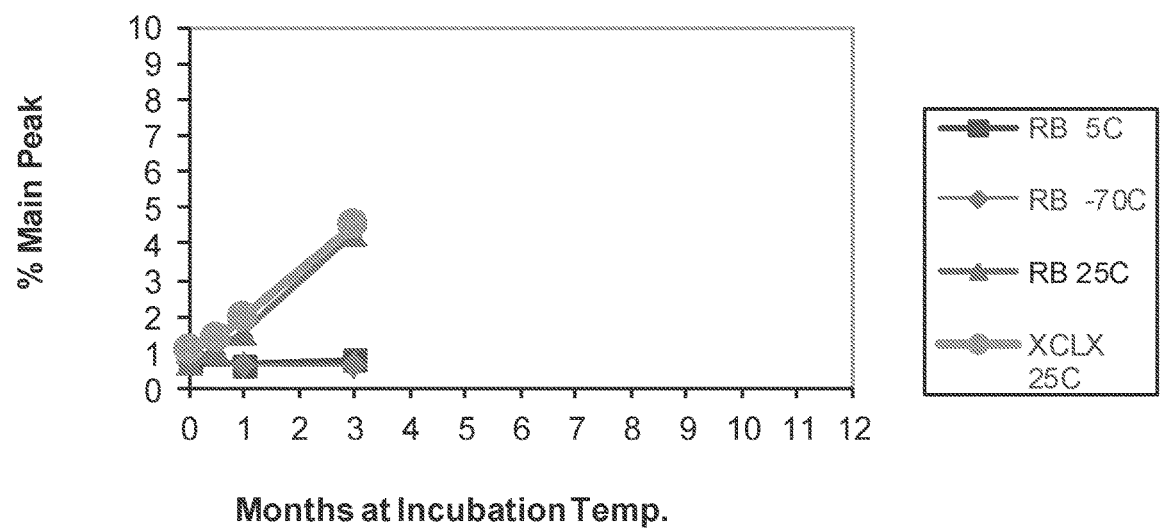
FIG. 31A is a graph showing differences in RP-HPLC Stability results between Rentschler (RB) and Xcellerex (XCLX)—Peak 3.
FIG. 31B is a table showing peak 3 Stability results of GMP1 (RB).
FIG. 31C is a table showing peak 3 Stability results of XCLX (tested at RB).
Figures 32A, 32B, 32C:
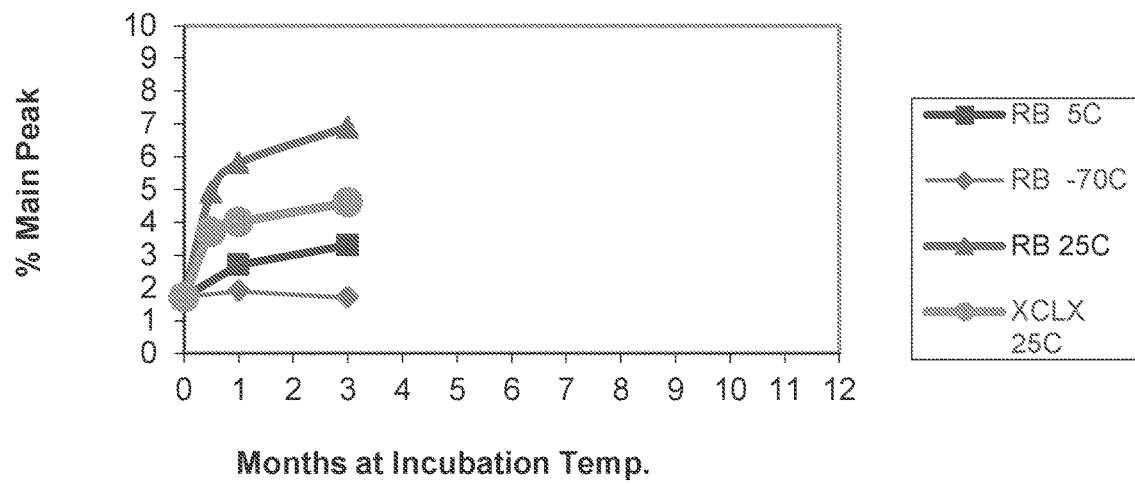
FIG. 32A is a graph showing differences in RP-HPLC Stability results between Rentschler (RB) and Xcellerex (XCLX)—Peak 5.
FIG. 32B is a table showing peak 5 stability results of GMP1 (RB).
FIG. 32C is a table showing peak 5 Stability results of XCLX (tested at RB).
Figure 33A:
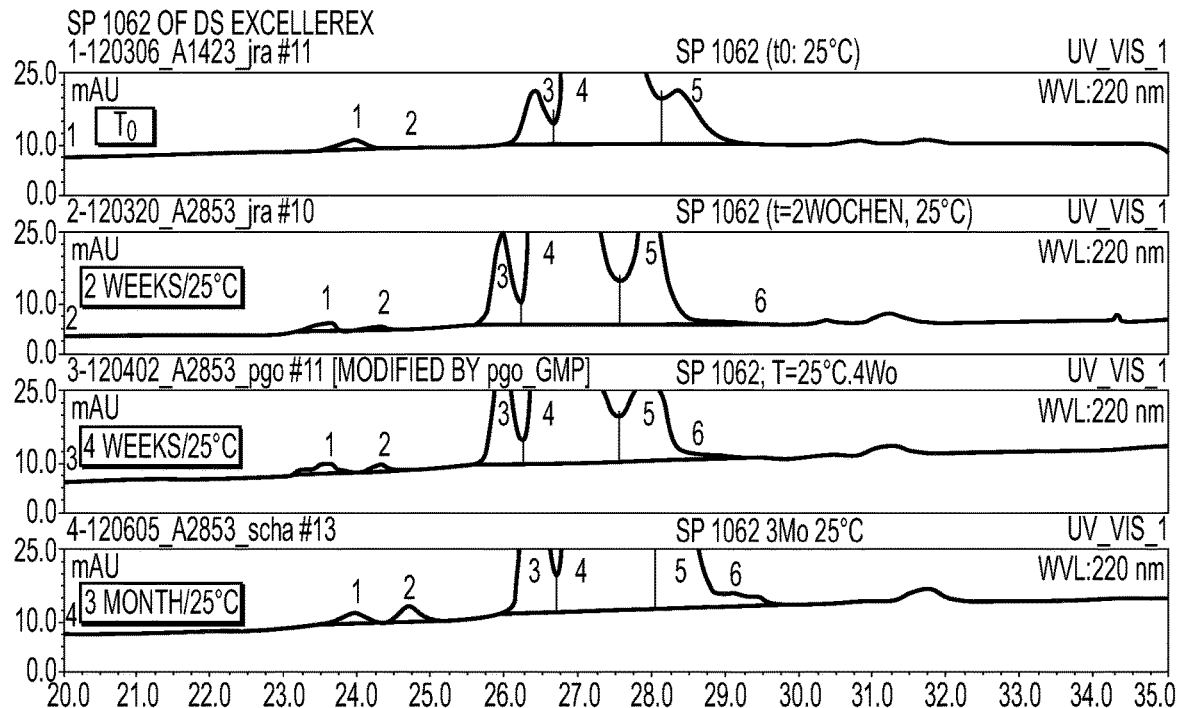
FIG. 33A is a graph showing stability results after 3 months at 25° CRP-HPLC, Batch GMP Xcellerex. Peak 7 was not observed at XC material.
Figure 33B:
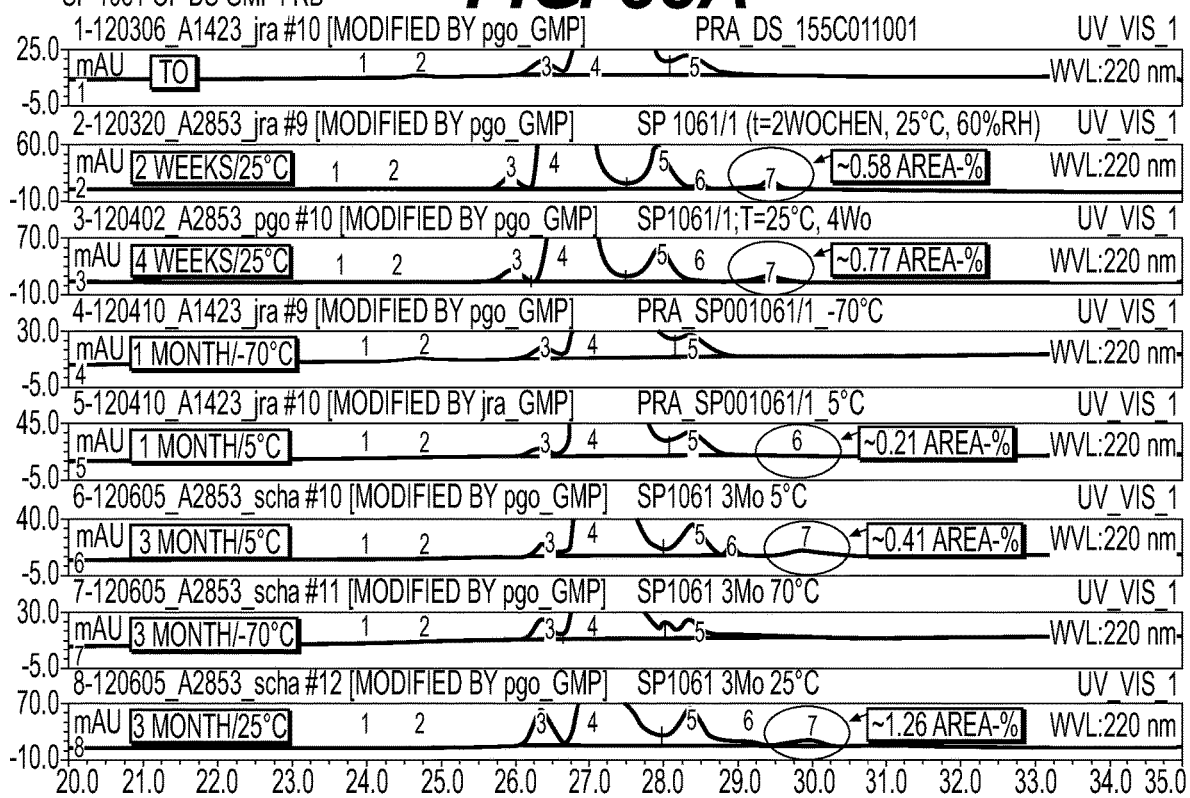
FIG. 33B is a graph showing Stability results RP-HPLC, Batch GMP-1 at Rentschler. Peak 7 which was not observed at XC material appears after 2 weeks at 25° C.
Figure 34:
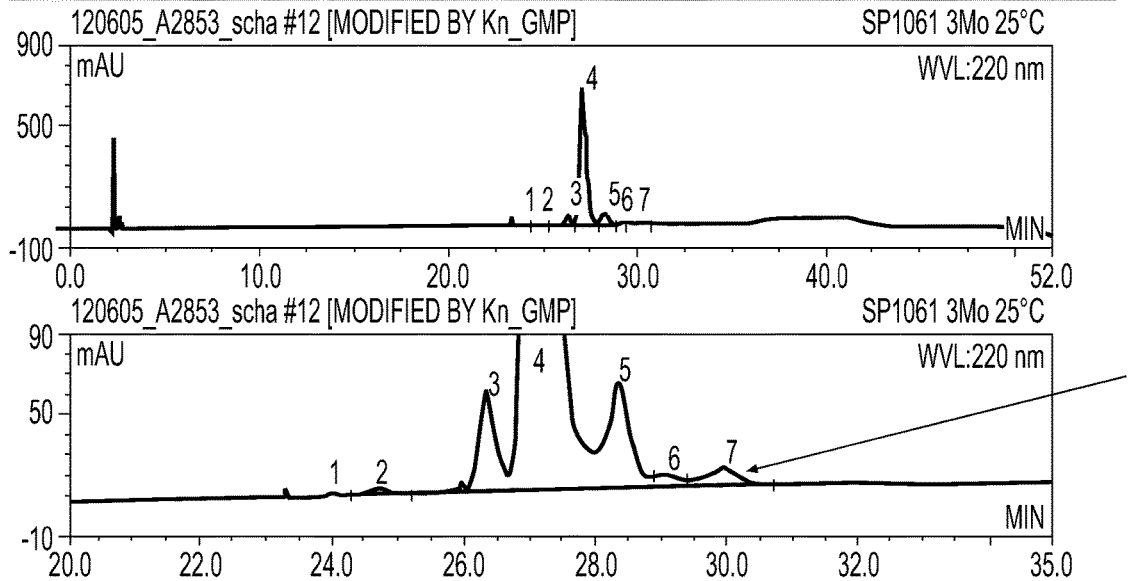
FIG. 34 is a graph showing RP-HPLC Stability GMP-1 after 3 months, 25° C. Arrow points to new Peak (7) which was not observed at XC material.

Based on the similarity between Clone 28 and Clone 2, which is stable at 5° C. for 24 m, it is expected that clone 28 produced at Xcellerex (XC) will be stable for 24 m at 5° C.; DP Main Peak Specification >88% (FIG. 28B).

Manufacturing of MOD-4023

Comparable profile at T=0 between Xcellerex (XC) to Rentschler (RB) DS (FIG. 29). FIGS. 30-34 show differences in stability between XC and RB. Isoelectric focusing (IEF) demonstrates that there's a similar band pattern in a pI-value range from 3.5 to 4.2. In one XC batch there are less faint isoforms in the high pI boundary and in an RB batch there are more faint isoforms in the low pI boundary (FIG. 35A). In addition, there are more diffuse bands in XC sample as compared to the RB sample (FIG. 35B).

Additional observations showed that the formation of both peaks (3 and 5—see below for peak definitions) is temperature dependent and accelerates at high temperature (FIG. 36A-D)). Further, there was no change in the % of peak 3 after incubation for up to 5 days at pH=4 and up to 2 h at pH=12 (FIG. 37B, 37D) and there was no change in the % of the peak after incubation for up to 6 h at pH=4.

However, following 6 h a sharp increase in the peak % was observed; at pH 12 incubation for up to 2 h—the peak disappears (FIG. 37A-D).

Forced Degradation Studies at RB (Clone 28)

A stressed sample of MOD-4023 drug substance was prepared (65° C. for about three days) for analysis of related form 5 in MOD-4023 drug substance as the peak is below the LOQ for the unstressed sample.

In order to test pH effect on RP-HPLC related forms three sample were tested:

RB—40 mg/ml, pH=5.9.
RB—10 mg/ml, pH=6.2.
XC—40 mg/ml, pH=6.2.

Figure 38:
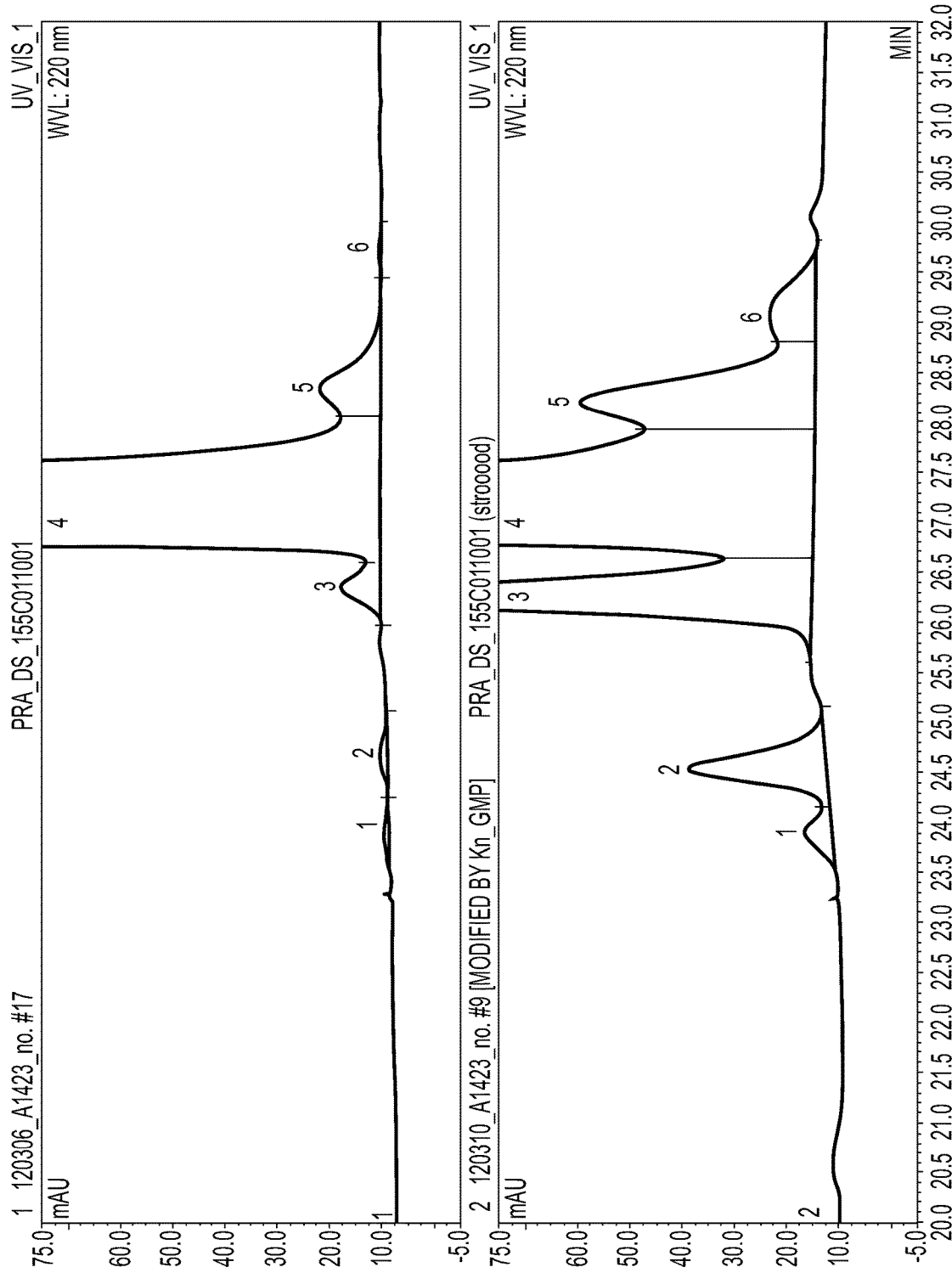
FIG. 38 shows Forced degradation studies at Rentschler (clone 28). Overlay of zooms of native (above) and stressed (below) MOD-4023 drug substance. A stressed sample of MOD-4023 (CTP-hGH-CTP-CTP) drug substance was prepared (65° C. for about three days) for analysis of related form 5 in MOD-4023 drug substance as the peak is below the LOQ for the unstressed sample.

Results are provided in FIGS. 38 and 39.

Isolation and Characterization of Related Form Peaks (1-7)—M-Scan

Peak 1—Oxidation of deamidated MOD-4023

Peak 2—Deamidation of MOD-4023

Peak 3—Partially oxidation of MOD-4023

Peak 5—Peptide bond cleavage between amino acid residues 167 and 168 and between amino acid residues 171 and 172 of MOD-4023. disulphide Peak 6 and peak 7—Truncated forms Conclusions (see FIGS. 24-39)

Stability

Clone 2 derived product is stable for up to 2 years at 5° C.

Clone 28 derived product manufactured at XC is stable for at least 1 year at 5° C. with similar profile as clone 2.

Clone 28 derived product manufactured at RB has altered stability profile with accelerated generation of related forms (mainly peak 5) and a generation of new peak (peak 7), not previously observed.

Previous studies show that Peak 3 and 5 have a similar Mw as the main peak and react with anti-hGH corresponding MOD-4023 band.

Both peaks: 3 and 5 are temperature dependent (the % of the peaks increases when the temperature is increased).

No change in the percentage of the HMW forms was observed during incubation at −20° C. and 5° C.

Stability of RB product GMP1 (after incubation of 2 weeks) at different temperatures: 5, 25, 37, 50 and 65° C. demonstrated that Peak 7 formation is accelerated at 25° C. and 37° C. but it is not observed at 50 and 65° C.

Incubation of RB samples for 10 min at 65° C. followed by incubation at 25° C. eradicated the generation of peak 7 (after 2 week at 25° C.).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims:

---

The invention claimed is:

1. A method for maintaining insulin-like growth factor (IGF-1) levels in a growth hormone deficient human prepubertal pediatric subject within a normal therapeutic range, comprising
administering to the growth hormone deficient human prepubertal pediatric subject a therapeutically effective amount of a glycosylated polypeptide comprising an amino terminal chorionic gonadotropin carboxy terminal peptide (CTP) of SEQ ID NO:18, a human growth hormone polypeptide, and two carboxy terminal chorionic gonadotropin CTPs, each of SEQ ID NO:18 and arranged in tandem (CTP-modified hGH polypeptide), the CTP-modified hGH polypeptide having the amino acid sequence as set forth in amino acids 27 to 301 of SEQ ID NO: 39,
wherein the therapeutically effective amount comprises a once a week dose of 0.66 milligrams per kilogram per week_(mg/kg/week), and
wherein the normal therapeutic range of IGF-1 levels is ±2 standard deviations (SDS) of the average IGF-1 levels in non-growth hormone deficient human prepubertal pediatric subjects.

2. The method of claim 1, wherein the IGF-1 levels comprise IGF-1 levels of samples tested four days post-administration of the CTP-modified hGH polypeptide.

3. The method of claim 1, wherein the IGF-1 levels are maintained within the normal therapeutic range of IGF-1 levels of ±2 SDS for at least 6 months.

4. The method of claim 1, wherein the normal therapeutic range of IGF-1 levels is ±1.5 SDS of the average IGF-1 levels in non-growth hormone deficient human prepubertal pediatric subject.

5. The method of claim 1, wherein the growth hormone deficient human prepubertal pediatric subject has a six month annualized height velocity increase of at least 12.25 centimeters (cm).

6. The method of claim 5, wherein the six month annualized height velocity increase is at least 13.48 cm.

7. The method of claim 6, wherein the six month annualized height velocity increase is at least 14.37 cm.

8. The method of claim 1, wherein the normal therapeutic range of IGF-1 levels is maintained in the growth hormone deficient human prepubertal pediatric subject for between about two weeks to four months.

9. The method of claim 1, wherein the normal therapeutic range of IGF-1 levels is maintained in the growth hormone deficient human prepubertal pediatric subject for four months.

10. The method of claim 1, wherein the normal therapeutic range of IGF-1 levels is maintained in the growth hormone deficient human prepubertal pediatric subject for six months.

11. The method of claim 1, wherein the growth hormone deficient human prepubertal pediatric subject is a naïve growth hormone deficient human prepubertal pediatric subject.

12. The method of claim 1, wherein a mean time interval of IGF-1 levels that are within the normal therapeutic range after the last dose administration is
(i) at least 119±66.51 hrs;
(ii) at least 120±66.24 hrs; or
(iii) at least 146±50.62 hrs.

13. The method of claim 1, wherein the CTP-modified hGH polypeptide is encoded by the nucleic acid sequence set forth in nucleotides 89 to 913 of SEQ ID NO: 45.

* * * * *